US007109332B2

(12) United States Patent
Scarborough et al.

(10) Patent No.: US 7,109,332 B2
(45) Date of Patent: *Sep. 19, 2006

(54) 2,4-DIOXO-3-QUINAZOLINYLARYL SULFONYLUREAS

(75) Inventors: Robert M. Scarborough, Half Moon Bay, CA (US); Wolin Huang, Foster City, CA (US); Anjali Pandey, Fremont, CA (US); Shawn M. Bauer, Pacifica, CA (US); Xiaoming Zhang, Sunnyvale, CA (US); Zhaozhong J. Jia, San Mateo, CA (US)

(73) Assignee: Portola Pharmaceuticals, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/956,004

(22) Filed: Sep. 29, 2004

(65) Prior Publication Data

US 2005/0107357 A1     May 19, 2005

Related U.S. Application Data

(60) Provisional application No. 60/508,564, filed on Oct. 3, 2003.

(51) Int. Cl.
*C07D 409/12* (2006.01)
*C07D 409/14* (2006.01)
*A61K 31/517* (2006.01)
*A61P 7/02* (2006.01)

(52) U.S. Cl. .................. 544/285; 514/266.24

(58) Field of Classification Search ........... 514/266.24; 544/285

See application file for complete search history.

(56) References Cited

U.S. PATENT DOCUMENTS

2002/0077486 A1    6/2002   Scarborough et al.

FOREIGN PATENT DOCUMENTS

| WO | WO 99/05144 A1 | 2/1999 |
| WO | WO 99/36425 A1 | 7/1999 |
| WO | WO 01/57037 A1 | 8/2001 |

OTHER PUBLICATIONS

Berge, S.M., et al, "Pharmaceutical salts." *J. Pharmaceut. Sci.*, vol. 66, No. 1., pp. 1-19 (1977).
Fratantoni J.C. and B.J. Poindexter, "Measuring platelet aggregation with microplate reader. A new technical approach to platelet aggregation studies." *Am. J. Clin. Pathol.*, vol. 94, No. 5; pp. 613-617 (1990).
Fredholm, B.B. et al., "Towards a revised nomenclature for P1 and P2 receptors." *Trends Pharmacol. Sci.*, vol. 18, No. 3; pp. 79-82 (1997).
Hechler, B. et al., "The P2Y1 receptor is necessary for adenosine 5'-diphosphate-Induced platelet aggregation." *Blood*, vol. 92, No. 1; pp. 152-159 (1998).
Hollopeter, G. et. al., "Identification of the platelet ADP receptor targeted by antithrombotic drugs." *Nature*, vol. 409, No. 6817; pp. 202-207 (2001).
Humphries et al., "A novel series of P2T purinoceptor antagonists: definition of the role of ADP in arterial thrombosis." *Trends Pharmacol. Sci.*, vol. 16, No. 6; pp. 179-181 (1995).
Ingall, A.H. et al., "Antagonists of the platelet P2T receptor: a novel approach to antithrombotic therapy." *J. Med. Chem.*, vol. 42, No. 2, pp. 213-220 (1999).
Jantzen, H.M. et al., "Evidence for two distince G-protein-coupled ADP receptors mediating platelet activation." *Thromb. Haemost.*, vol. 81, No. 1; pp. 111-117 (1999).
King, B.F. et al., "Metabotropic receptors for ATP and UTP: exploring the correspondence between native and recombinant nucleotide receptors." *Trends Pharmacol. Sci.* vol. 19, No. 12; pp. 506-514 (1998).
Kunapuli, S.P. and J.L. Daniel, "P2 receptor subtypes in the cardiovascular system." *Biochem. J.*, vol. 336, No. 3; pp. 513-523 (1998).

Kunapuli, S.P., "Multiple P2 receptor subtypes on platelets: a new interpretation of their function." *Trends Pharmacol. Sci.*, vol. 19, No. 10; pp. 391-394 (1998).

Mills, D.C.B. "ADP receptors on platelets." *Thromb. Haemost.*, vol. 76, No. 6, pp. 835-856 (1996).

Quinn, M.J. and D.J. Fitzgerald, "Ticlopidine and clopidogrel." *Circulation*, vol. 100, No. 15; pp. 1667-1672 (1999).

Urban, F.J. et al., "Novel synthesis of 1-(1,2,3,5,6,7-hexahydro-s-indacen-4-yl)-3-[4-(1-hydroxy-1-methyl-ethyl)-furan-2-sulfonyl]urea, an anti-inflammatory agent." *Synth. Comm.*, vol. 33, No. 12, pp. 2029-2043 (2003).

*Primary Examiner*—Thomas C. McKenzie
(74) *Attorney, Agent, or Firm*—Townsend and Townsend and Crew LLP

(57) ABSTRACT

2,4-Dioxo-3-quinazolinylaryl sulfonylurea compounds having the formula:

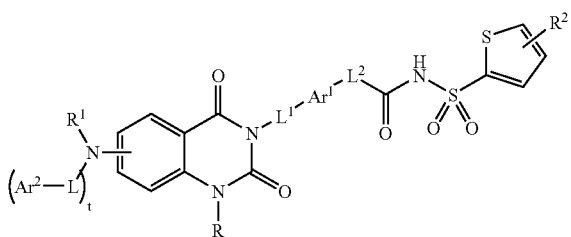

wherein

R is a member selected from the group consisting of H and $C_{1-6}$ alkyl;

$R^1$ is a member selected from the group consisting of H, $C_{1-6}$ alkyl, $C_{1-6}$ haloalkyl, $C_{3-5}$ cycloalkyl and $C_{3-5}$ cycloalkyl-alkyl;

$R^2$ is a member selected from the group consisting of H, halogen, $C_{1-6}$ alkyl, $C_{2-6}$ alkenyl, $C_{2-6}$ alkynyl, $C_{1-6}$ haloalkyl, $C_{1-6}$ alkoxy, cyano and —C(O)$R^{2a}$, wherein $R^{2a}$ is a member selected from the group consisting of $C_{1-6}$ alkoxy and $(C_{1-6}$ alkyl$)_{0-2}$ amino;

L is a 1 to 3 carbon linking group selected from the group consisting of —CH$_2$—, —CH(CH$_3$)—, —CH$_2$CH$_2$—, —CH$_2$CH(CH$_3$)— and —CH$_2$CH$_2$CH$_2$—;

$L^1$ is a linking group selected from the group consisting of a bond and —CH$_2$—;

$L^2$ is a linking group selected from the group consisting of a bond, —NH— and —CH$_2$—; and $Ar^1$ is an aromatic ring selected from the group consisting of benzene, pyridine and pyrimidine;

are provided. The compounds are useful for the inhibition of ADP-platelet aggregation, particularly in the treatment of thrombosis and thrombosis related conditions or disorders.

46 Claims, 3 Drawing Sheets

2,4-DIOXO-3-QUINAZOLINYLARYL SULFONYLUREAS

CROSS-REFERENCES TO RELATED APPLICATIONS

This application claims the benefit of Provisional Application Ser. No. 60/508,564, filed Oct. 3, 2003, the disclosure of which is incorporated herein by reference.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Thrombotic complications are a major cause of death in the industrialized world. Examples of these complications include acute myocardial infarction, unstable angina, chronic stable angina, transient ischemic attacks, strokes, peripheral vascular disease, preeclampsia/eclampsia, deep venous thrombosis, embolism, disseminated intravascular coagulation and thrombotic cytopenic purpura. Thrombotic and restenotic complications also occur following invasive procedures, e.g., angioplasty, carotid endarterectomy, post CABG (coronary artery bypass graft) surgery, vascular graft surgery, stent placements and insertion of endovascular devices and protheses. It is generally thought that platelet aggregates play a critical role in these events. Blood platelets, which normally circulate freely in the vasculature, become activated and aggregate to form a thrombus with disturbed blood flow caused by ruptured atherosclerotic lesions or by invasive treatments such as angioplasty, resulting in vascular occlusion. Platelet activation can be initiated by a variety of agents, e.g., exposed subendothelial matrix molecules such as collagen, or by thrombin which is formed in the coagulation cascade.

An important mediator of platelet activation and aggregation is ADP (adenosine 5'-diphosphate) which is released from blood platelets in the vasculature upon activation by various agents, such as collagen and thrombin, and from damaged blood cells, endothelium or tissues. Activation by ADP results in the recruitment of more platelets and stabilization of existing platelet aggregates. Platelet ADP receptors mediating aggregation are activated by ADP and some of its derivatives and antagonized by ATP (adenosine 5'-triphosphate) and some of its derivatives (Mills, D. C. B. (1996) Thromb. Hemost. 76:835–856). Therefore, platelet ADP receptors are members of the family of P2 receptors activated by purine and/or pyrimidine nucleotides (King, B. F., Townsend-Nicholson, A. & Burnstock, G. (1998) Trends Pharmacol. Sci. 19:506–514).

Recent pharmacological data using selective antagonists suggests that ADP-dependent platelet aggregation requires activation of at least two ADP receptors (Kunapuli, S. P. (1998), Trends Pharmacol. Sci. 19:391–394; Kunapuli, S. P. & Daniel, J. L. (1998) Biochem. J. 336:513–523; Jantzen, H. M. et al. (1999) Thromb. Hemost. 81:111–117). One receptor appears to be identical to the cloned P2Y$_1$ receptor, mediates phospholipase C activation and intracellular calcium mobilization and is required for platelet shape change. The second platelet ADP receptor important for aggregation mediates inhibition of adenylyl cyclase. Molecular cloning of the gene or cDNA for this receptor (P2Y$_{12}$) has recently been reported (Hollopeter, G. et. al. (2001) Nature 409: 202–207). Based on its pharmacological and signaling properties this receptor has been previously termed P2Y$_{ADP}$ (Fredholm, B. B. et al. (1997) TIPS 18:79–82), P2T$_{AC}$ (Kunapuli, S. P. (1998), Trends Pharmacol. Sci. 19:391–394) or P2Y$_{cyc}$ (Hechler, B. et al. (1998) Blood 92, 152–159).

Various directly or indirectly acting synthetic inhibitors of ADP-dependent platelet aggregation with antithrombotic activity have been reported. The orally active antithrombotic thienopyridines ticlopidine and clopidogrel inhibit ADP-induced platelet aggregation, binding of radiolabeled ADP receptor agonist 2-methylthioadenosine 5'-diphosphate to platelets, and other ADP-dependent events indirectly, probably via formation of an unstable and irreversible acting metabolite (Quinn, M. J. & Fitzgerald, D. J. (1999) Circulation 100:1667–1667). Some purine derivatives of the endogenous antagonist ATP, e.g., AR-C (formerly FPL or ARL) 67085MX and AR-C69931MX, are selective platelet ADP receptor antagonists which inhibit ADP-dependent platelet aggregation and are effective in animal thrombosis models (Humphries et al. (1995), Trends Pharmacol. Sci. 16, 179; Ingall, A. H. et al. (1999) J. Med. Chem. 42, 213–230). Novel triazolo[4,5-d]pyrimidine compounds have been disclosed as P$_{2T}$-antagonists (WO 99/05144). Tricyclic compounds as platelet ADP receptor inhibitors have also been disclosed in WO 99/36425. The target of these antithrombotic compounds appears to be the platelet ADP receptor mediating inhibition of adenylyl cyclase.

Despite these compounds, there exists a need for more effective platelet ADP receptor inhibitors. In particular, there is a need for platelet ADP receptor inhibitors having antithrombotic activity that are useful in the prevention and/or treatment of cardiovascular diseases, particularly those related to thrombosis.

BRIEF SUMMARY OF THE INVENTION

In one aspect, the present invention provides compounds having the formula:

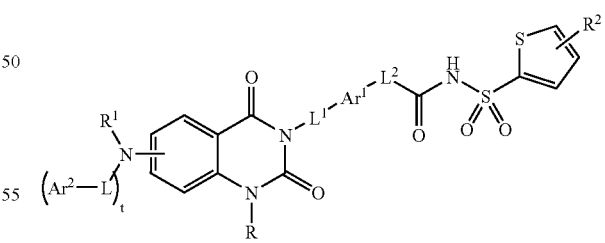

or a pharmaceutically acceptable salt thereof, wherein R represents H or C$_{1-6}$ alkyl; R$^1$ represents a member selected from H, C$_{1-6}$ alkyl, C$_{1-6}$ haloalkyl, C$_{3-5}$ cycloalkyl and C$_{3-5}$ cycloalkyl-alkyl; R$^2$ represents a member selected from H, halogen, C$_{1-6}$ alkyl, C$_{2-6}$ alkenyl, C$_{2-6}$ alkynyl, C$_{1-6}$ haloalkyl, C$_{1-6}$ alkoxy, cyano and —C(O)R$^{2a}$, wherein R$^{2a}$ is selected from C$_{1-6}$ alkoxy and (C$_{1-6}$ alkyl)$_{0-2}$ amino.

The letter L represents a 1 to 3 carbon linking group selected from —CH$_2$—, —CH(CH$_3$)—, —CH$_2$CH$_2$—, —CH$_2$CH(CH$_3$)— and —CH$_2$CH$_2$CH$_2$—. The symbol L$^1$ represents a bond or —CH$_2$—. The symbol L$^2$ represents a bond, —NH— or —CH$_2$—.

The subscript t is an integer of from 0 to 1 when L$^2$ is a bond, and is 1 when L$^2$ is —NH— or —CH$_2$—.

Ar$^1$ is an aromatic ring selected from benzene, pyridine and pyrimidine, each of which is optionally substituted with from 1–2 R$^3$ substituents, wherein each R$^3$ is independently selected from halogen, cyano, hydroxy, C$_{1-6}$ alkyl, C$_{2-6}$ alkenyl, C$_{2-6}$ alkynyl, C$_{1-6}$ alkoxy, C$_{1-6}$ haloalkyl, C$_{1-6}$ haloalkoxy, C$_{3-5}$ cycloalkyl, C$_{3-5}$ cycloalkyl-alkyl, C$_{3-5}$ cycloalkyl-alkoxy, (C$_{1-6}$ alkyl)$_{0-2}$ amino, —C(O)R$^{3a}$, —O(CH$_2$)$_m$OR$^{3b}$, —(CH$_2$)$_m$OR$^{3b}$, —O(CH$_2$)$_m$N(R$^{3b}$)$_2$ and —(CH$_2$)$_m$N(R$^{3b}$)$_2$, wherein the subscript m is an integer of from 1 to 3, each R$^{3a}$ is independently selected from H, hydroxy, C$_{1-6}$ alkyl, C$_{1-6}$ alkoxy, (C$_{1-6}$ alkyl)$_{0-2}$ amino, and each R$^{3b}$ is independently selected from H, C$_{1-4}$ alkyl and C$_{1-4}$ alkanoyl, and optionally, two R$^{3b}$ groups attached to nitrogen are combined with the nitrogen atom to form an azetidine, pyrrolidine or piperidine ring.

Ar$^2$ is a 5–6 membered monocyclic or 9–10 membered fused-bicyclic aromatic ring system, optionally having from 1 to 3 heteroatoms selected from N, O and S as ring vertices, the ring system being optionally substituted with from 1 to 3 R$^4$ substituents, wherein each of the R$^4$ substituents is independently selected from halogen, cyano, hydroxy, C$_{1-6}$ alkyl, C$_{2-6}$ alkenyl, C$_{2-6}$ alkynyl, C$_{1-6}$ alkoxy, C$_{1-6}$ haloalkyl, C$_{1-6}$ haloalkoxy, C$_{3-5}$ cycloalkyl, C$_{3-5}$ cycloalkyl-alkyl, C$_{3-5}$ cycloalkyl-alkoxy, (C$_{1-6}$ alkyl)$_{0-2}$ amino and —C(O)R$^{4a}$, and each R$^{4a}$ is independently selected from H, hydroxy, C$_{1-6}$ alkyl, C$_{1-6}$ alkoxy and (C$_{1-6}$ alkyl)$_{0-2}$ amino.

The present invention further provides pharmaceutical compositions containing one or more of the above compounds in admixture with a pharmaceutically acceptable excipient.

In other aspects, the present invention provides methods of treating thrombosis and thrombosis related conditions or disorders wherein a compound having the formula above is administered to a patient in need of such treatment.

DETAILED DESCRIPTION OF THE INVENTION

Definitions

Figure 1:
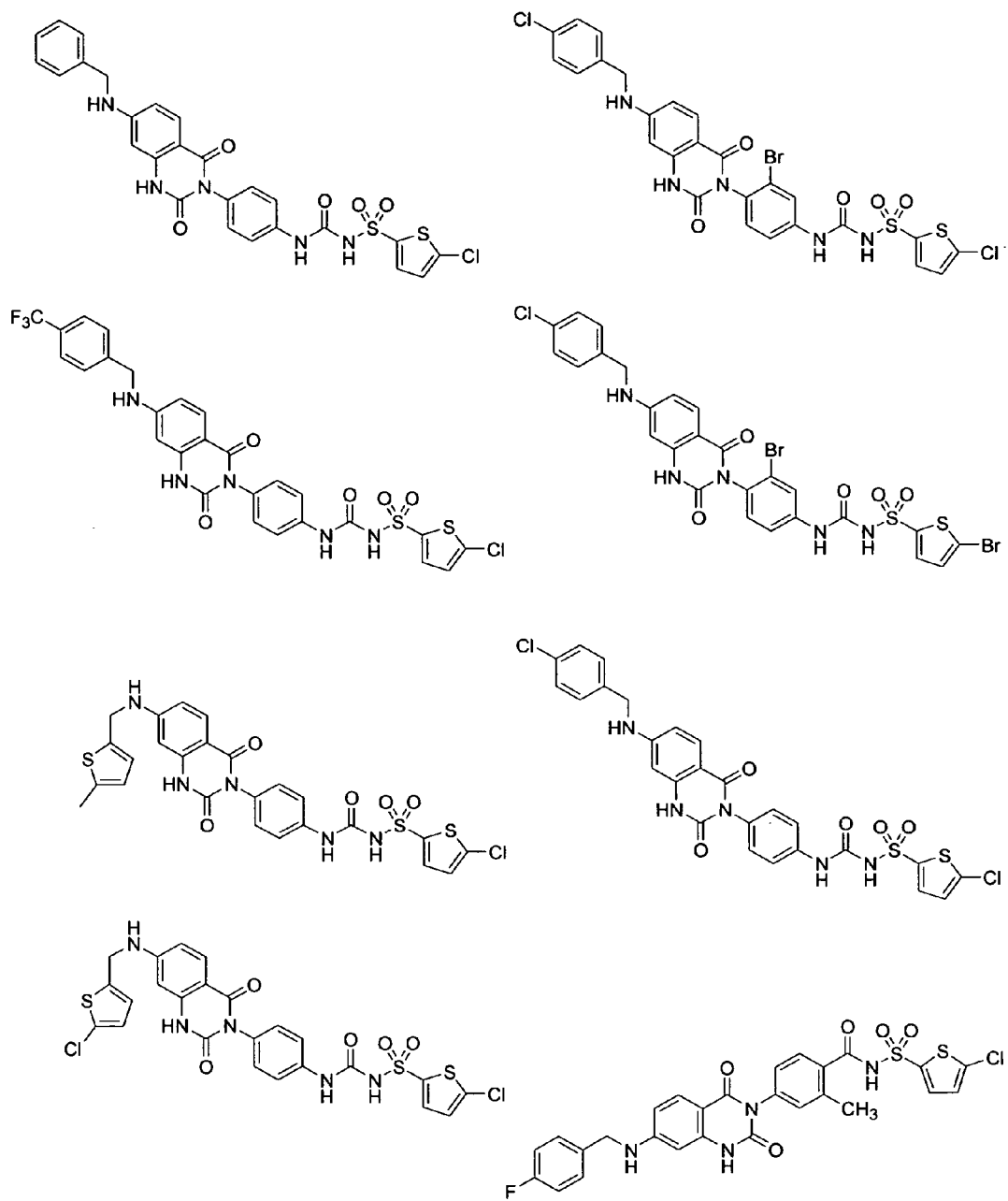
FIGS. 1–3 provide structures of selected and preferred compounds of the invention.

The term "alkyl", by itself or as part of another substituent, means, unless otherwise stated, a straight or branched chain hydrocarbon radical, having the number of carbon atoms designated (i.e. C$_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "alkenyl" refers to an unsaturated alkyl group is one having one or more double bonds. Similarly, the term "alkynyl" refers to an unsaturated alkyl group having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl" refers to hydrocarbon rings having the indicated number of ring atoms (e.g., C$_{3-6}$cycloalkyl) and being fully saturated or having no more than one double bond between ring vertices. When "cycloalkyl" is used in combination with "alkyl", as in C$_{3-5}$ cycloalkyl-alkyl, the cycloalkyl portion is meant to have from three to five carbon atoms, while the alkyl portion is an alkylene moiety having from one to three carbon atoms (e.g., —CH$_2$—, —CH$_2$CH$_2$— or —CH$_2$CH$_2$CH$_2$—).

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. For brevity, the term C$_{1-6}$alkylamino is meant to include straight chain, branched or cyclic alkyl groups or combinations thereof, such as methyl, ethyl, 2-methylpropyl, cyclobutyl and cyclopropylmethyl.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "C$_{1-4}$ haloalkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. Exemplary aryl groups are phenyl, naphthyl, biphenyl and the like. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of heteroaryl groups include 1-pyrrolyl, 2-pyrrolyl, 3-pyrrolyl, 1-pyrazolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, benzopyrazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science,* 1977, 66, 1–19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers (e.g., separate enantiomers) are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

DESCRIPTION OF THE EMBODIMENTS

Compounds

In view of the above, the present invention provides, in one aspect, compounds having the formula:

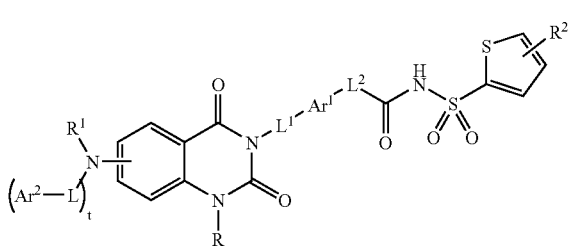

I or a pharmaceutically acceptable salt thereof, wherein R represents H or $C_{1-6}$ alkyl, preferably H or $CH_3$, and more preferably H. The symbol $R^1$ represents a member selected from H, $C_{1-6}$ alkyl, $C_{1-6}$ haloalkyl, $C_{3-5}$ cycloalkyl and $C_{3-5}$ cycloalkyl-alkyl, more preferably H or $C_{1-4}$ alkyl, still more preferably H or $CH_3$, and most preferably H. The symbol $R^2$ represents a member selected from H, halogen, $C_{1-6}$ alkyl, $C_{2-6}$ alkenyl, $C_{2-6}$ alkynyl, $C_{1-6}$ haloalkyl, $C_{1-6}$ alkoxy, cyano and —C(O)$R^{2a}$, wherein $R^{2a}$ is selected from $C_{1-6}$ alkoxy and $(C_{1-6}$ alkyl$)_{0-2}$ amino. More preferably $R^2$ is selected from halogen, $C_{1-4}$ alkyl, $C_{1-4}$ alkoxy, $C_{1-4}$ haloalkyl, —CN, —C≡CH and —CONH$_2$. Still more preferably, $R^2$ is halogen and is attached to the 5-position of the thienyl ring.

The letter L represents a 1 to 3 carbon linking group selected from —CH$_2$—, —CH(CH$_3$)—, —CH$_2$CH$_2$—, —CH$_2$CH(CH$_3$)— and —CH$_2$CH$_2$CH$_2$—. Preferably, L is selected from —CH$_2$—, —CH(CH$_3$)— and —CH$_2$CH$_2$—. More preferably, L is selected from —CH$_2$— and —CH (CH$_3$)—. The symbol $L^1$ represents a bond or —CH$_2$—, preferably a bond. The symbol $L^2$ represents a bond, —NH— or —CH$_2$—, preferably a bond or —NH—. In further preferred embodiments, $L^2$ is —NH—.

The subscript t is an integer of from 0 to 1 when $L^2$ is a bond, and is 1 when $L^2$ is —NH— or —CH$_2$—.

$Ar^1$ is an aromatic ring selected from benzene, pyridine and pyrimidine, each of which is optionally substituted with from 1–2 $R^3$ substituents, wherein each $R^3$ is independently selected from halogen, cyano, hydroxy, $C_{1-6}$ alkyl, $C_{2-6}$ alkenyl, $C_{2-6}$ alkynyl, $C_{1-6}$ alkoxy, $C_{1-6}$ haloalkyl, $C_{1-6}$ haloalkoxy, $C_{3-5}$ cycloalkyl, $C_{3-5}$ cycloalkyl-alkyl, $C_{3-5}$ cycloalkyl-alkoxy, $(C_{1-6}$ alkyl$)_{0-2}$ amino, —C(O)$R^{3a}$, —O(CH$_2$)$_m$OR$^{3b}$, —(CH$_2$)$_m$OR$^{3b}$, —O(CH$_2$)$_m$N(R$^{3b}$)$_2$ and —(CH$_2$)$_m$N(R$^{3b}$)$_2$, wherein the subscript m is an integer of from 1 to 3, each $R^{3a}$ is independently selected from H, hydroxy, $C_{1-6}$ alkyl, $C_{1-6}$ alkoxy, $(C_{1-6}$ alkyl$)_{0-2}$ amino, and each $R^{3b}$ is independently selected from H, $C_{1-4}$ alkyl and $C_{1-4}$ alkanoyl, and optionally, two $R^{3b}$ groups attached to nitrogen are combined with the nitrogen atom to form an azetidine, pyrrolidine or piperidine ring. Preferably, each $R^3$ is independently selected from $C_{1-4}$ alkyl, $C_{1-4}$ alkoxy, $C_{3-5}$ cycloalkyl-alkoxy, —O(CH$_2$)$_m$OR$^{3b}$ and —O(CH$_2$)$_m$N (R$^{3b}$)$_2$ wherein the subscript m is 1 or 2 and each $R^{3b}$ is independently selected from H, $C_{1-4}$ alkyl and $C_{1-4}$ alkanoyl.

$Ar^2$ is a 5–6 membered monocyclic or 9–10 membered fused-bicyclic aromatic ring system, optionally having from 1 to 3 heteroatoms selected from N, O and S as ring vertices, the ring system being optionally substituted with from 1 to 3 $R^4$ substituents, wherein each of the $R^4$ substituents is independently selected from halogen, cyano, hydroxy, $C_{1-6}$ alkyl, $C_{2-6}$ alkenyl, $C_{2-6}$ alkynyl, $C_{1-6}$ alkoxy, $C_{1-6}$ haloalkyl, $C_{1-6}$ haloalkoxy, $C_{3-5}$ cycloalkyl, $C_{3-5}$ cycloalkyl-alkyl, $C_{3-5}$ cycloalkyl-alkoxy, $(C_{1-6}$ alkyl$)_{0-2}$ amino and —C(O)$R^{4a}$, and each $R^{4a}$ is independently selected from H, hydroxy, $C_{1-6}$ alkyl, $C_{1-6}$ alkoxy and $(C_{1-6}$ alkyl$)_{0-2}$ amino. In one group of preferred embodiments, $Ar^2$ is benzene or naphthalene, each of which is optionally substituted with from 1 to 3 $R^4$ substituents. In another group of preferred embodiments, $Ar^2$ is furan, thiophene, thiazole, oxazole, thiadiazole, imidazole, pyrazole, pyridine or pyrimidine, each of which is optionally substituted with from 1 to 3, or more preferably 1 to 2 $R^4$ substituents. In still another group of preferred embodiments, $Ar^2$ is benzothiophene, indole, quinoline, isoquinoline, benzofuran, benzimidazole, benzoxazole or benzothiazole, each of which is optionally substituted with from 1 to 3, or more preferably 1 to 2 $R^4$ substituents.

In Formula I above, the group Ar²-L-N(R¹)— is preferably attached to the 6- or 7-position of the 2,4-dioxo-quinazoline ring system, numbered as shown below:

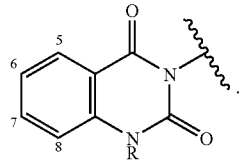

More preferably, the group Ar²-L-N(R¹)— is attached to the 7-position of the 2,4-dioxo-quinazoline ring system.

Within the descriptions above are a number of preferred embodiments. In one group of preferred embodiments, R¹ is H or $C_{1-4}$ alkyl; L is —$CH_2$—, —$CH(CH_3)$— or —$CH_2CH_2$—; $L^1$ is a bond and R² is halogen, $C_{1-4}$ alkyl, $C_{1-4}$ alkoxy, $C_{1-4}$ haloalkyl, —CN, —C≡CH or —$CONH_2$.

In another group of preferred embodiments, Ar¹ is a benzene ring, optionally substituted with 1–2 R³ substituents. In yet another group of preferred embodiments, Ar¹ is a pyridine ring, optionally substituted with 1–2 R³ substituents. In still another group of preferred embodiments, Ar¹ is a pyrimidine ring, optionally substituted with 1–2 R³ substituents. Within each of these groups of embodiments, one group of further preferred compounds are those in which Ar² is benzene or naphthalene, each of which is optionally substituted with from 1 to 3 R⁴ substituents. Still further preferred in this group of embodiments are those compounds in which R¹ is H or $C_{1-4}$ alkyl; L is —$CH_2$—, —$CH(CH_3)$— or —$CH_2CH_2$—; $L^1$ is a bond and R² is halogen, $C_{1-4}$ alkyl, $C_{1-4}$ alkoxy, $C_{1-4}$ haloalkyl, —CN, —C≡CH or —$CONH_2$.

In a related group of preferred embodiments, Ar¹ is a benzene ring, optionally substituted with 1–2 R³ substituents and Ar² is furan, thiophene, thiazole, oxazole, thiadiazole, imidazole, pyrazole, pyridine, pyrimidine, benzothiophene, indole, quinoline, isoquinoline, benzofuran, benzimidazole, benzoxazole or benzothiazole, each of which is optionally substituted with from 1 to 3 R⁴ substituents. In one group of embodiments, Ar² is a monocyclic ring selected from furan, thiophene, thiazole, oxazole, thiadiazole, imidazole, pyrazole, pyridine and pyrimidine. In another group of embodiments, Ar² is a fused bicyclic ring system selected from benzothiophene, indole, quinoline, isoquinoline, benzofuran, benzimidazole, benzoxazole and benzothiazole. One of skill in the art will appreciate that attachment to the remainder of the compound can be through any available valence site on the ring or ring system. For example, "pyridine" is meant to include 2-pyridyl, 3-pyridyl and 4-pyridyl moieties. Similarly, attachment for one of the fused ring systems can be through either of the two rings. For example, "benzothiazole" is meant to include 2-benzothiazolyl as well as 5-benzothiazolyl and the like. Preferred attachment sites are those provided in the Examples and Figures herein. Still further preferred in each of these groups of embodiments are those compounds in which R¹ is H or $C_{1-4}$ alkyl; L is —$CH_2$—, —$CH(CH_3)$— or —$CH_2CH_2$—; $L^1$ is a bond and R² is halogen, $C_{1-4}$ alkyl, $C_{1-4}$ alkoxy, $C_{1-4}$ haloalkyl, —CN, —C≡CH or —$CONH_2$.

One group of particularly preferred embodiments, compounds of the present invention are represented by formula Ia:

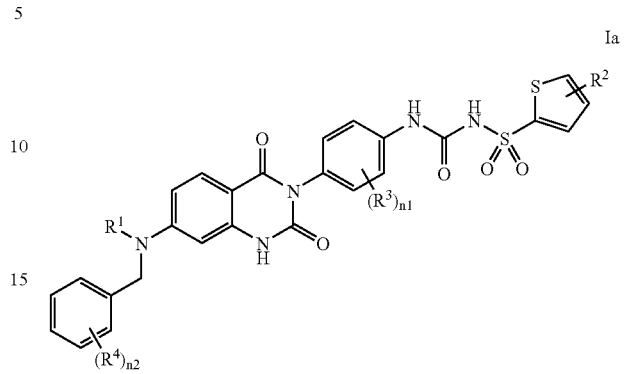

wherein the subscripts n1 and n2 each independently represent an integer of from 0 to 2. The remaining groups R¹, R², R³ and R⁴ have the meanings provided with respect to formula I above. Further preferred for the compounds of formula Ia are those in which R¹ is H; R² is selected from halogen, $C_{1-4}$ alkyl, $C_{1-4}$ alkoxy, $C_{1-4}$ haloalkyl, —CN, —C≡CH and —$CONH_2$; each R³, when present is independently selected from $C_{1-4}$ alkyl, $C_{1-4}$ alkoxy, $C_{3-5}$ cycloalkyl-alkoxy, —$O(CH_2)_mOR^{3b}$ and —$O(CH_2)_mN(R^{3b})_2$ wherein the subscript m is 1 or 2 and each $R^{3b}$ is independently selected from H, $C_{1-4}$ alkyl and $C_{1-4}$ alkanoyl; and each R⁴, when present is independently selected from halogen, cyano, hydroxy, $C_{1-6}$ alkyl, $C_{2-6}$ alkenyl, $C_{2-6}$ alkynyl, $C_{1-6}$ alkoxy, $C_{1-6}$ haloalkyl, $C_{3-5}$ cycloalkyl, $C_{3-5}$ cycloalkyl-alkyl, $C_{3-5}$ cycloalkyl-alkoxy and ($C_{1-6}$ alkyl)$_{0-2}$ amino. Still further preferred are those compounds of formula Ia wherein R² is halogen and is attached to the 5-position of the thienyl ring; and each R⁴ when present is independently selected from halogen, cyano and $C_{1-6}$ alkyl.

Another group of particularly preferred compounds of the present invention are represented by formula Ib:

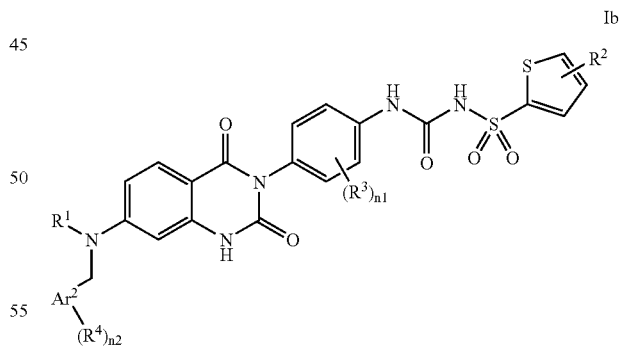

wherein the subscripts n1 and n2 each independently represent an integer of from 0 to 2. The remaining groups Ar², R¹, R², R³ and R⁴ have the meanings provided with respect to formula I above. In one group of preferred embodiments, for the compounds of formula Ib, Ar² is selected from furan, thiophene, thiazole, oxazole, thiadiazole, imidazole, pyrazole, pyridine and pyrimidine. In another group of preferred embodiments, Ar² is a fused bicyclic ring system selected from benzothiophene, indole, quinoline, isoquinoline, benzofuran, benzimidazole, benzoxazole and benzothiazole. Further preferred for each group of embodiments of formula Ib are those in which $R^1$ is H; $R^2$ is selected from halogen, $C_{1-4}$ alkyl, $C_{1-4}$ alkoxy, $C_{1-4}$ haloalkyl, —CN, —C≡CH and —CONH$_2$; each $R^3$, when present is independently selected from $C_{1-4}$ alkyl, $C_{1-4}$ alkoxy, $C_{3-5}$ cycloalkyl-alkoxy, —O(CH$_2$)$_m$OR$^{3b}$ and —O(CH$_2$)$_m$N(R$^{3b}$)$_2$ wherein the subscript m is 1 or 2 and each $R^{3b}$ is independently selected from H, $C_{1-4}$ alkyl and $C_{1-4}$ alkanoyl; and each $R^4$, when present is independently selected from halogen, cyano, hydroxy, $C_{1-6}$ alkyl, $C_{2-6}$ alkenyl, $C_{2-6}$ alkynyl, $C_{1-6}$ alkoxy, $C_{1-6}$ haloalkyl, $C_{3-5}$ cycloalkyl, $C_{3-5}$ cycloalkyl-alkyl, $C_{3-5}$ cycloalkyl-alkoxy and $(C_{1-6}$ alkyl)$_{0-2}$ amino. Still further preferred are those compounds of formula Ib wherein $R^2$ is halogen and is attached to the 5-position of the thienyl ring; and each $R^4$ when present is selected from halogen, cyano and $C_{1-6}$ alkyl.

Another group of particularly preferred compounds of the present invention are represented by formula Ic:

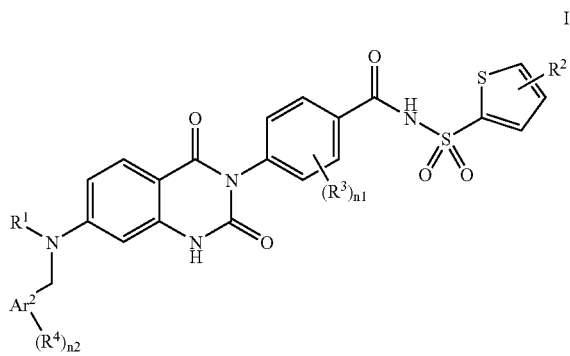

wherein the subscripts n1 and n2 each independently represent an integer of from 0 to 2. The remaining groups Ar$^2$, $R^1$, $R^2$, $R^3$ and $R^4$ have the meanings provided with respect to formula I above. In one group of preferred embodiments, for the compounds of formula Ic, Ar$^2$ is selected from furan, thiophene, thiazole, oxazole, thiadiazole, imidazole, pyrazole, pyridine and pyrimidine. In another group of preferred embodiments, Ar$^2$ is a fused bicyclic ring system selected from benzothiophene, indole, quinoline, isoquinoline, benzofuran, benzimidazole, benzoxazole and benzothiazole. Further preferred for each group of embodiments of formula Ic are those in which $R^1$ is H; $R^2$ is selected from halogen, $C_{1-4}$ alkyl, $C_{1-4}$ alkoxy, $C_{1-4}$ haloalkyl, —CN, —C≡CH and —CONH$_2$; each $R^3$, when present is independently selected from $C_{1-4}$ alkyl, $C_{1-4}$ alkoxy, $C_{3-5}$ cycloalkyl-alkoxy, —O(CH$_2$)$_m$OR$^{3b}$ and —O(CH$_2$)$_m$N(R$^{3b}$)$_2$ wherein the subscript m is 1 or 2 and each $R^{3b}$ is independently selected from H, $C_{1-4}$ alkyl and $C_{1-4}$ alkanoyl; and each $R^4$, when present is independently selected from halogen, cyano, hydroxy, $C_{1-6}$ alkyl, $C_{2-6}$ alkenyl, $C_{2-6}$ alkynyl, $C_{1-6}$ alkoxy, $C_{1-6}$ haloalkyl, $C_{3-5}$ cycloalkyl, $C_{3-5}$ cycloalkyl-alkyl, $C_{3-5}$ cycloalkyl-alkoxy and $(C_{1-6}$ alkyl)$_{0-2}$ amino. Still further preferred are those compounds of formula Ib wherein $R^2$ is halogen and is attached to the 5-position of the thienyl ring; and each $R^4$ when present is selected from halogen, cyano and $C_{1-6}$ alkyl.

Another group of particularly preferred compounds of the present invention are represented by formula Id:

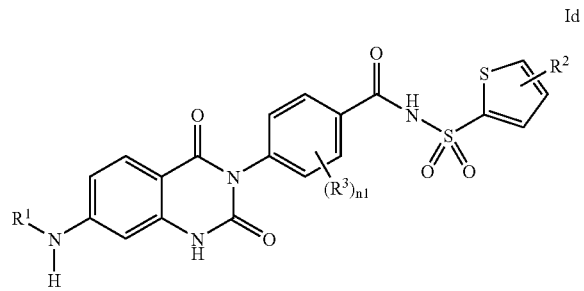

wherein the subscript n1 represents an integer of from 0 to 2, and $R^1$ is a member selected from $C_{1-6}$ alkyl, $C_{1-6}$ haloalkyl, $C_{3-5}$ cycloalkyl and $C_{3-5}$ cycloalkyl-alkyl. The remaining groups $R^2$ and $R^3$ have the meanings provided with respect to formula I above. In preferred embodiments, $R^2$ is selected from halogen, $C_{1-4}$ alkyl, $C_{1-4}$ alkoxy, $C_{1-4}$ haloalkyl, —CN, —C≡CH and —CONH$_2$; and each $R^3$, when present is independently selected from $C_{1-4}$ alkyl, $C_{1-4}$ alkoxy, $C_{3-5}$ cycloalkyl-alkoxy, —O(CH$_2$)$_m$OR$^{3b}$ and —O(CH$_2$)$_m$N(R$^{3b}$)$_2$ wherein the subscript m is 1 or 2 and each $R^{3b}$ is independently selected from the group consisting of H, $C_{1-4}$ alkyl and $C_{1-4}$ alkanoyl. Still further preferred are those compounds of formula Id wherein $R^2$ is halogen and is attached to the 5-position of the thienyl ring.

Figure 2:
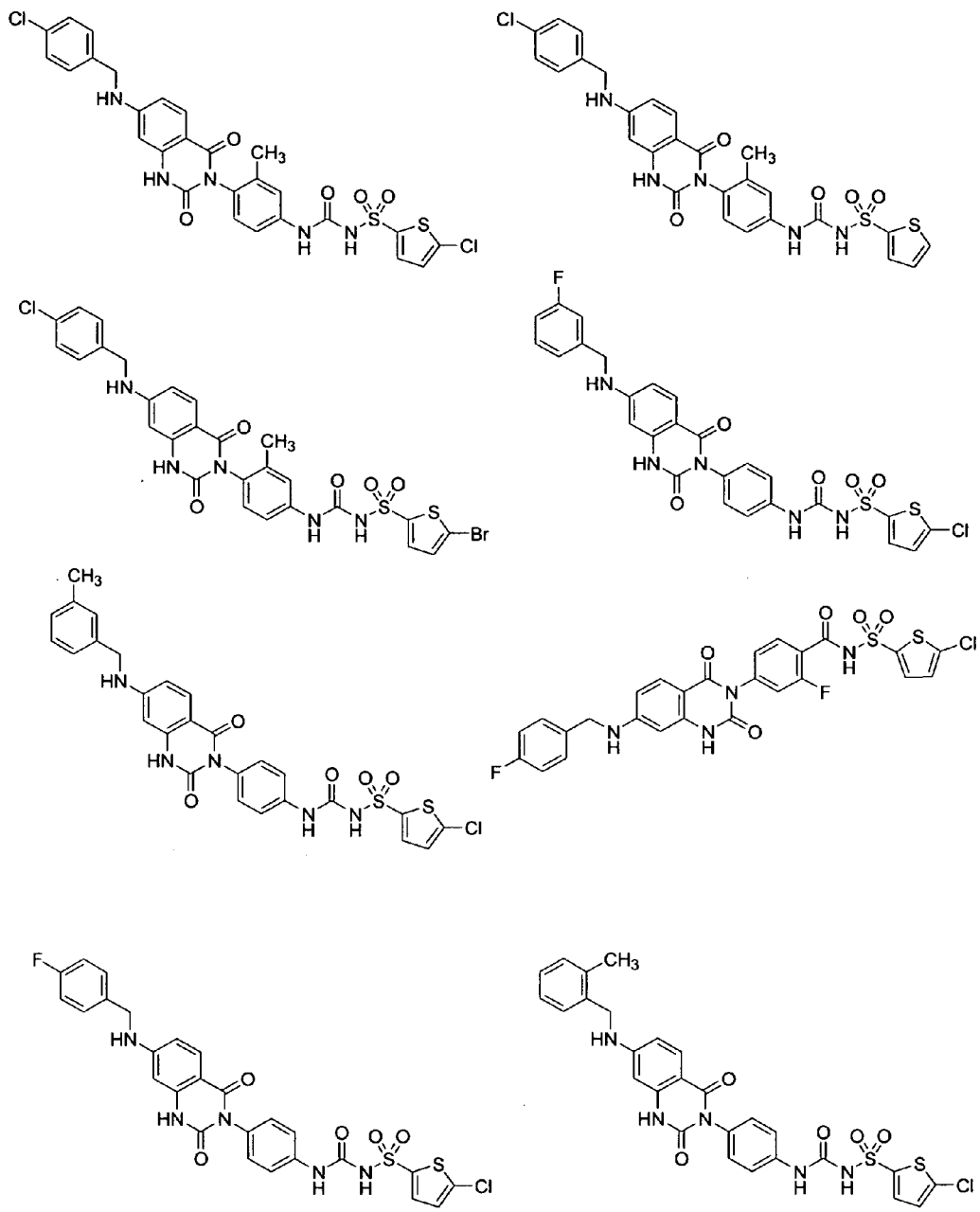
Figure 3:
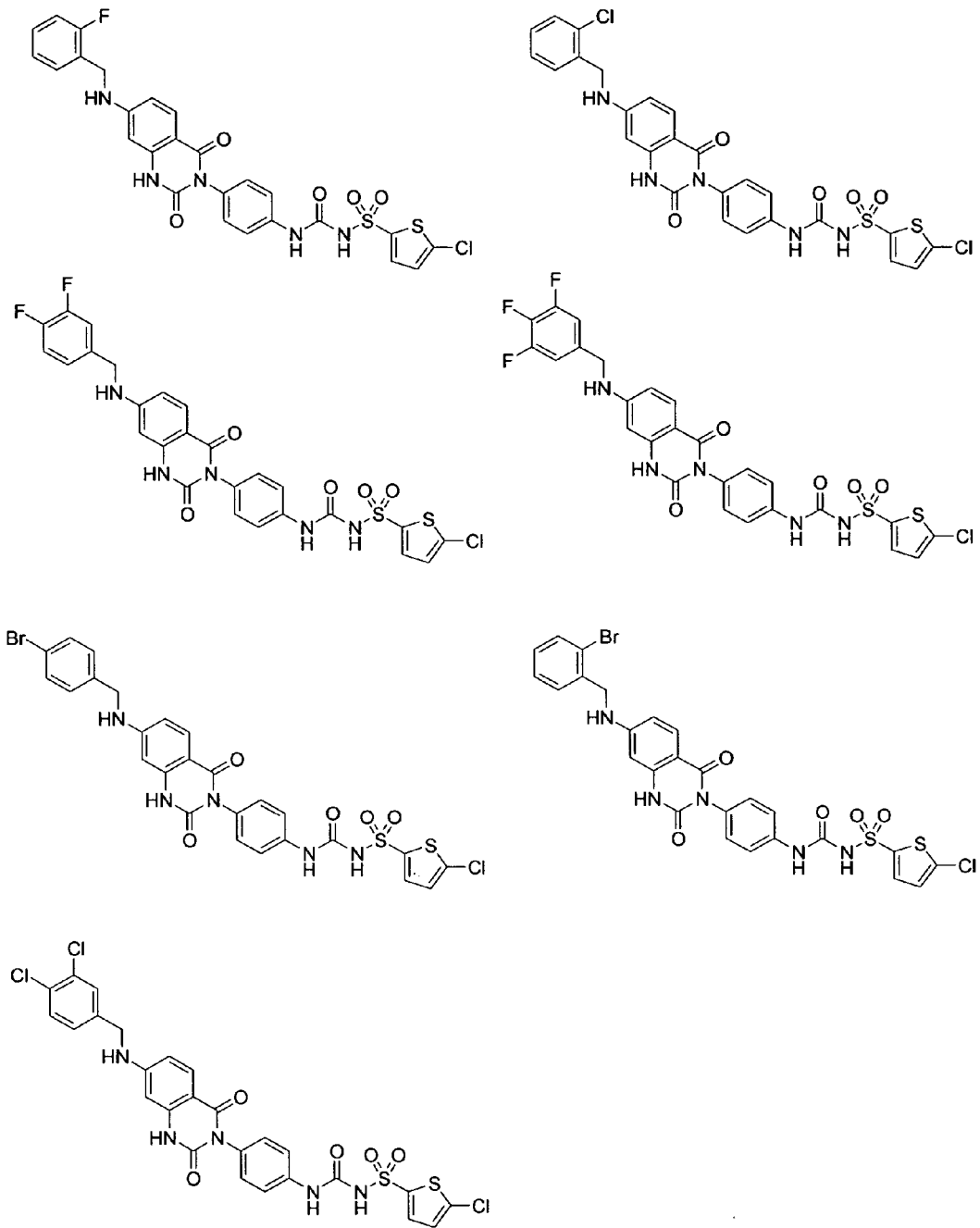

A number of specific compounds are among the most preferred embodiments for the compounds of formula I, and are provided in FIGS. 1–3.

Preparation of the Compounds of Formula I

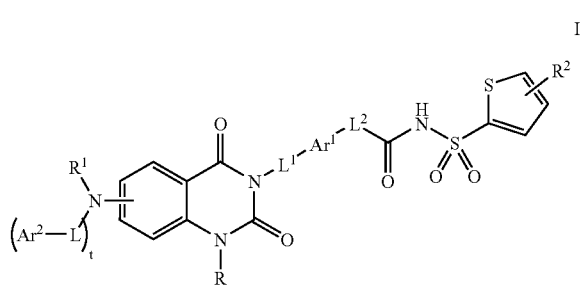

Scheme 1 illustrates a method of preparing certain compounds of Formula I wherein $R^1$, $R^2$, Ar$^1$ and Ar$^2$ are described above.

SCHEME 1

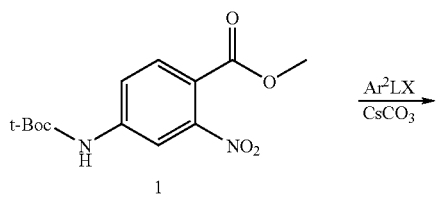

1

-continued

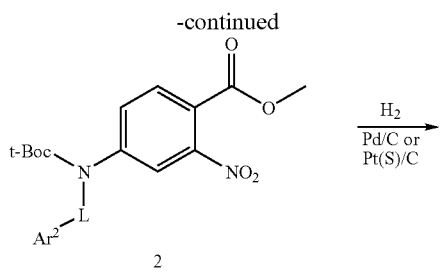

2

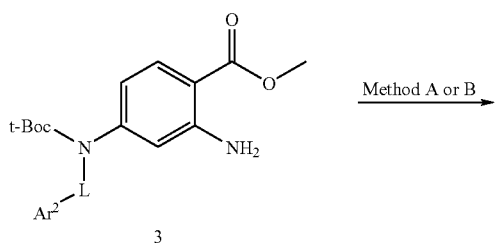

3

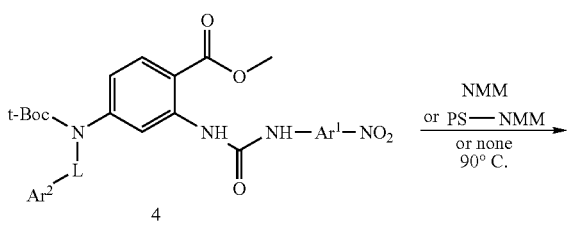

4

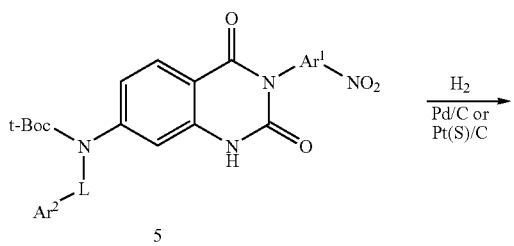

5

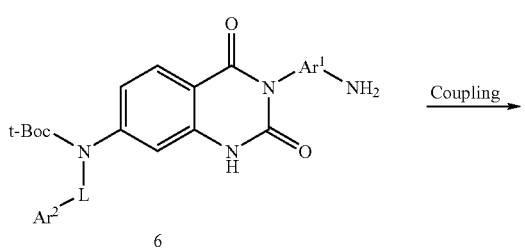

6

-continued

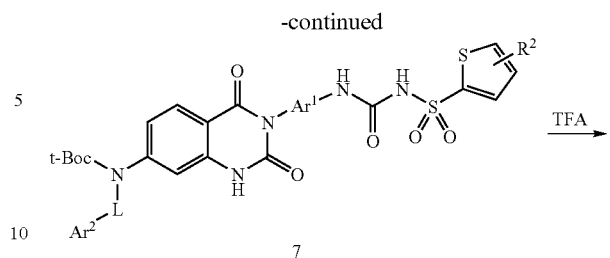

7

8

A compound of Formula I can be prepared by reacting 4-tert-butoxycarbonylamino-2-nitro-benzoic acid methyl ester, prepared by previously described methods (see published patent application US2002077486) and substituted arylalkyl halides in the presence of a base such as potassium carbonate, cesium carbonate or sodium hydride in a inert solvent such as DMF of THF to obtain a compound 2. The nitro group of compound 2 can be reduced by procedures known to one skilled in the art to yield aniline 3. For example, a method of nitro group reduction can be carried out by hydrogenation. The hydrogenation is carried out with a suitable catalyst (e.g., 10% Pd/C or Pt(s)/C) under hydrogen and in an appropriate solvent, typically in an alcohol, preferably ethanol at room temperature. Treating compound 3 with appropriately substituted aryl or heteroaryl isocyante (Method A) provides intermediate urea 4. Alternatively, urea 4 can be formed by treating compound 3 with triphosgene in the presence of a base such as triethylamine or diisopropylethylamine in an inert solvent such as THF, dichloromethane and MeCN at appropriate temperature, preferably at 20 C.°, followed by substituted aryl or heteroaryl amines (Method B). Urea 4, prepared by Method A or Method B typically without further purification can be subjected to thermal or based induced ring closure to provide quinazolindione 5. The nitro group of compound 5 can be reduced by procedures known to one skilled in the art to yield free amino group. For example, a method of reduction can be carried out by hydrogenation, with a suitable catalyst (e.g., 10% palladium on carbon) in an appropriate solvent, typically an alcohol. The formation of sulfonylurea linkage can be accomplished by treating the reduced product aniline 6 with a pre-mixed solution of substituted thiophene-2-sulfonamide, N,N'-disuccinimidyl carbonate and tetramethylguanidine in dichloromethane, followed by treatment with TFA in dichloromethane at room temperature to afford the sulfonylurea of Formula I. Alternatively, the sulfonylurea linkage can be formed by reacting the aniline 6 and 5-Chloro-thiophene-2-sulfonamide ethylcarbonate in toluene.

Scheme 2 illustrates an alternative method of preparing compounds of Formula I wherein $R^1$, $R^2$, $Ar^1$ and $Ar^2$ are described above.

SCHEME 2

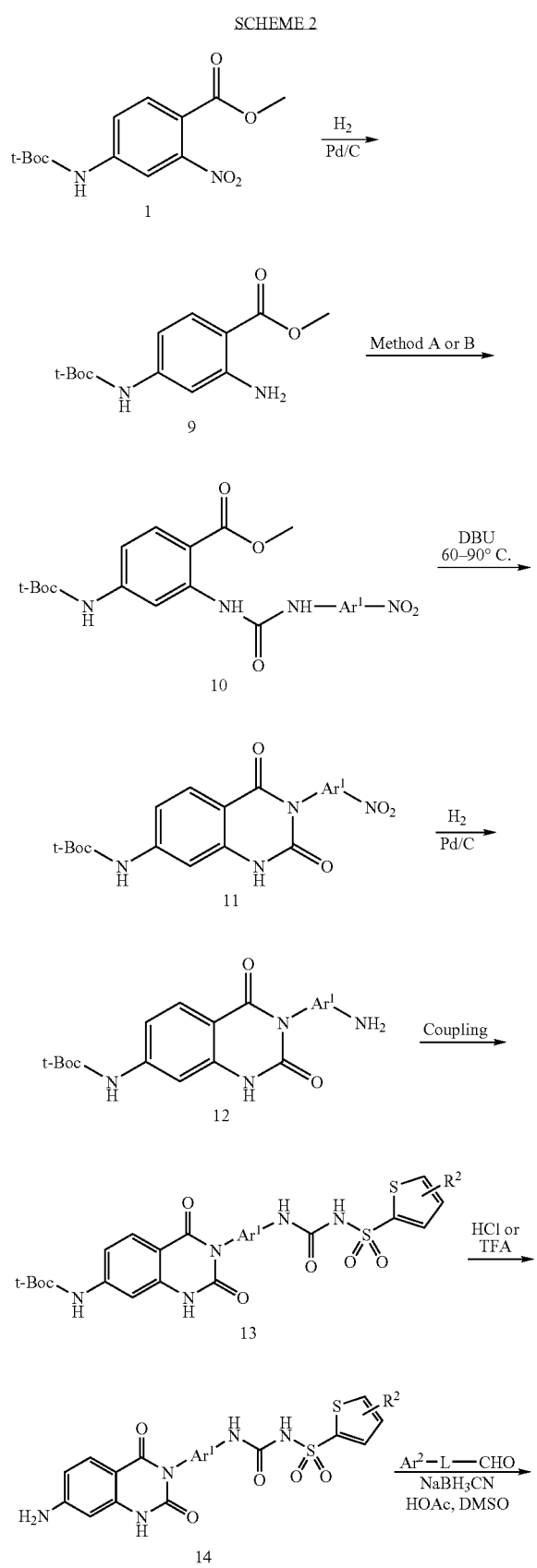

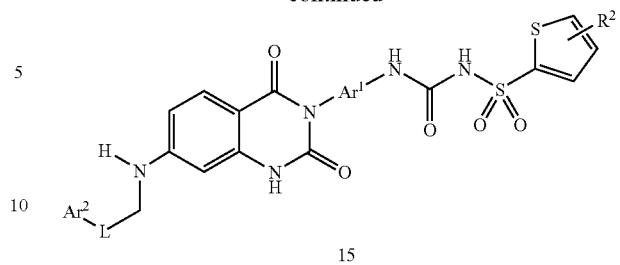

A compound of Formula I can be prepared by reducing 4-tert-butoxycarbonylamino-2-nitro-benzoic acid methyl ester to aniline 9 by standard hydrogenation with 10% Pd/C in ethyl acetate. Treating compound 9 with appropriately substituted aryl or heteroaryl isocyante (Method A) provides intermediate urea 10. Alternatively, urea 10 can be formed by treating compound 9 with triphosgene in the presence of a base such as triethylamine or diisopropylethylamine in an inert solvent such as THF, dichloromethane and MeCN at appropriate temperature, preferably at 20° C., followed by substituted aryl or heteroaryl amines (Method B). Urea 10, prepared by Method A or Method B typically without further purification can be subjected to thermal or based induced ring closure to provide quinazolindione 11. The nitro group of compound 11 can be reduced by procedures known to one skilled in the art to yield free amino group. For example, a method of reduction can be carried out by hydrogenation, with a suitable catalyst (e.g., 10% palladium on carbon) in an appropriate solvent, typically ethyl acetate, methanol, dimethylformamide or a mixture of them. The preparation of sulfonylurea 13 can be accomplished by treating aniline 12 with a pre-mixed solution of substituted thiophene-2-sulfonamide, N,N'-disuccinimidyl carbonate and tetramethylguanidine in dichloromethane, followed by treatment with TFA in dichloromethane at room temperature to afford the sulfonylurea of Formula I. Alternatively, compound 13 can be prepared by reacting the aniline 6 and 5-chloro-thiophene-2-sulfonamide ethylcarbonate in hot toluene, dioxane or acetonitrile. Treatment of compound 13 using a 1:1 mixture of dichloromethane and trifluoroacetic acid, or using the commercial 4N HCl solution in dioxane, in ice bath yields aniline 14. Reductive amination of aniline 14 with an aldehyde, sodium cyanoborohydride and acetic acid in methyl sulfoxide gives target compound 15.

SCHEME 3

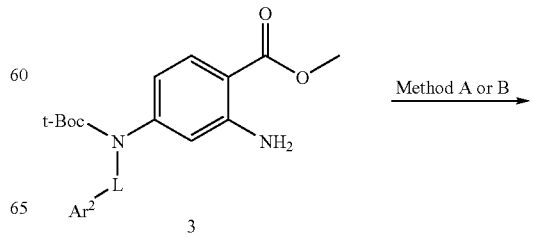

-continued

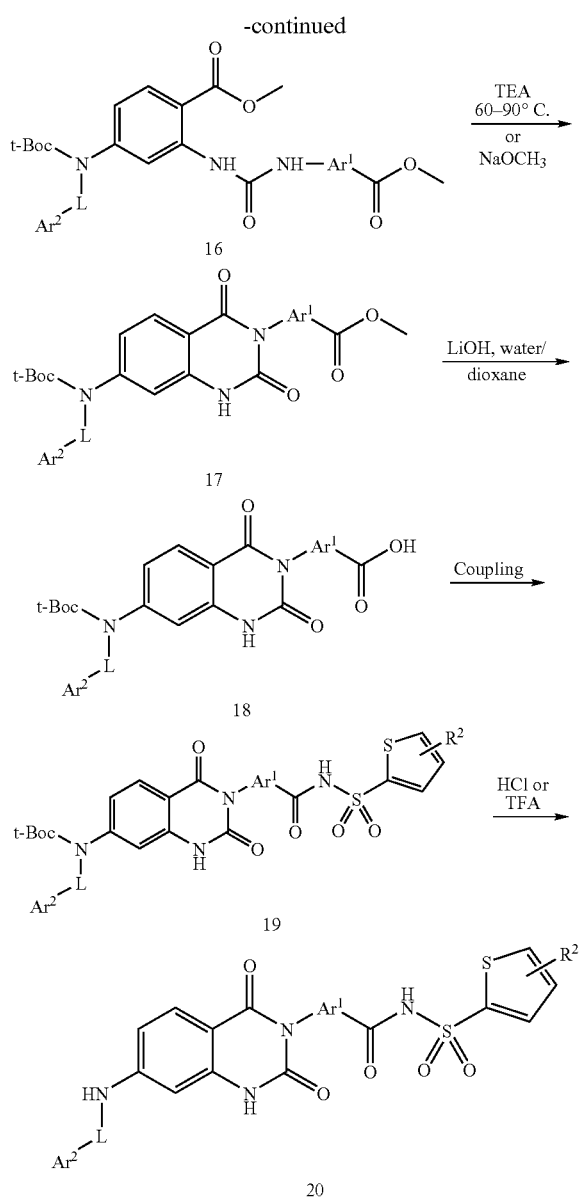

A compound of Formula I, wherein acylsulfonamide is the linker, can be prepared by treating compound 3 with appropriately substituted aryl or heteroaryl isocyante (Scheme 3, Method A) to provide intermediate urea 16. Alternatively, urea 16 can be formed by treating compound 3 with triphosgene in the presence of a base such as triethylamine or diisopropylethylamine in an inert solvent such as THF, dichloromethane and MeCN at appropriate temperature, preferably at 20° C., followed by substituted aryl or heteroaryl amines (Method B). Urea 16, prepared by Method A or Method B typically without further purification can be subjected to thermal or based induced ring closure to provide quinazolindione 17. The ester of compound 17 can be converted to the carboxylic acid by treatment with lithium hydroxide in an appropriate solvent or solvent mixture such as dioxane/water or THF/water. Conversion of the carboxylic acid to acyl sulfonamide 19 is accomplished by treatment with DIC, DMAP and a suitably substituted sulfonamide in either dichloromethane or DMF as the solvent. Treatment of the Boc protected analog with acid, either 50% TFA in dichloromethane or 4M HCl in dioxane, affords the acylsulfonamide of Formula I.

Compositions

In another aspect of the invention, pharmaceutical compositions are provided in which compounds of formulae I, Ia, Ib, Ic or Id, alone or in combination, are combined with a pharmaceutically acceptable carrier. Preferred compounds for use in the compositions of the present invention are those compounds identified above as specific or preferred embodiments.

The pharmaceutical compositions of the invention may be in the form of solutions or suspensions. In the management of thrombotic disorders the compounds or pharmaceutical compositions of the invention may also be in such forms as, for example, tablets, capsules or elixirs for oral administration, suppositories, sterile solutions or suspensions or injectable administration, and the like, or incorporated into shaped articles.

Typical adjuvants which may be incorporated into tablets, capsules and the like include, but are not limited to, binders such as acacia, corn starch or gelatin, and excipients such as microcrystalline cellulose, disintegrating agents like corn starch or alginic acid, lubricants such as magnesium stearate, sweetening agents such as sucrose or lactose, or flavoring agents. When a dosage form is a capsule, in addition to the above materials it may also contain liquid carriers such as water, saline, or a fatty oil. Other materials of various types may be used as coatings or as modifiers of the physical form of the dosage unit. Sterile compositions for injection can be formulated according to conventional pharmaceutical practice. For example, dissolution or suspension of the active compound in a vehicle such as an oil or a synthetic fatty vehicle like ethyl oleate, or into a liposome may be desired. Buffers, preservatives, antioxidants and the like can be incorporated according to accepted pharmaceutical practice.

Additionally, dosage formulations of compounds of formulae I, Ia, Ib, Ic or Id, or pharmaceutical compositions containing a compound of the invention, to be used for therapeutic administration must be sterile. Sterility can be readily accomplished by filtration through sterile membranes such as 0.2 micron membranes, or by other conventional methods. Formulations typically will be stored in a solid form, preferably in a lyophilized form. While the preferred route of administration is orally, the dosage formulations of compounds of formulae I, Ia, Ib, Ic or Id, or pharmaceutical compositions of the invention may also be administered by injection, intravenously (bolus and/or infusion), subcutaneously, intramuscularly, colonically, rectally, nasally, transdermally or intraperitoneally. A variety of dosage forms may be employed as well including, but not limited to, suppositories, implanted pellets or small cylinders, aerosols, oral dosage formulations and topical formulations such as ointments, drops and dermal patches. The compounds of formulae I, Ia, Ib, Ic or Id, and pharmaceutical compositions of the invention may also be incorporated into shapes and articles such as implants which may employ inert materials such biodegradable polymers or synthetic silicones as, for example, SILASTIC, silicone rubber or other polymers commercially available. The compounds and pharmaceutical compositions of the invention may also be provided in the form of liposome delivery systems, such as small unilamellar vesicles, large unilamellar vesicles and multilamellar vesicles. Liposomes can be formed from a variety of lipids, such as cholesterol, stearylamine or phosphatidylcholines, used methods well known to one of skill in the art.

Methods of Treatment/Administration

In yet another aspect, the present invention provides methods for preventing or treating thrombosis in a mammal by administering to the mammal a therapeutically effective amount of a compound of formulae I, Ia, Ib, Ic or Id, alone or as part of a pharmaceutical composition of the invention as described above. Compounds of formulae I, Ia, Ib, Ic or Id, and pharmaceutical compositions of the invention containing a compound of formulae I, Ia, Ib, Ic or Id, of the invention are suitable for use alone or as part of a multi-component treatment regimen for the prevention or treatment of cardiovascular diseases, particularly those related to thrombosis. For example, a compound or pharmaceutical composition of the invention may be used as a drug or therapeutic agent for any thrombosis, particularly a platelet-dependent thrombotic indication, including, but not limited to, acute myocardial infarction, unstable angina, chronic stable angina, transient ischemic attacks, strokes, peripheral vascular disease, preeclampsia/eclampsia, deep venous thrombosis, embolism, disseminated intravascular coagulation and thrombotic cytopenic purpura, thrombotic and restenotic complications following invasive procedures, e.g., angioplasty, carotid endarterectomy, post CABG (coronary artery bypass graft) surgery, vascular graft surgery, stent placements and insertion of endovascular devices and protheses.

Compounds and pharmaceutical compositions of the invention may also be used as part of a multi-component treatment regimen in combination with other therapeutic or diagnostic agents in the prevention or treatment of thrombosis in a mammal. In certain preferred embodiments, compounds or pharmaceutical compositions of the invention may be coadministered along with other compounds typically prescribed for these conditions according to generally accepted medical practice such as anticoagulant agents, thrombolytic agents, or other antithrombotics, including platelet aggregation inhibitors, tissue plasminogen activators, urokinase, prourokinase, streptokinase, heparin, aspirin, or warfarin. Still other agents that can be administered with the compounds of the present invention include anti-platelet compounds, fibrinolytics, anti-inflammatory compounds, cholesterol-lowering agents, blood-pressure-lowering agents and serotonin blockers. Suitable antiplatelet compounds include GPIIB–IIIa antagonists, aspirin, phosphodiesterase III inhibitors and thromboxane A2 receptor antagonists. Suitable anticoagulants include thrombin inhibitors, coumadin (Warfarin), heparin and Lovenox®. Suitable anti-inflammatory compounds include non-steroidal anti-inflammatory agents, cyclooxygenase-2 inhibitors and rheumatoid arthritis agents. Coadministrations of these agents with the compounds of the invention may also allow for application of reduced doses of the thrombolytic agents and therefore minimize potential hemorrhagic side-effects. Compounds and pharmaceutical compositions of the invention may also act in a synergistic fashion to prevent reocclusion following a successful thrombolytic therapy and/or reduce the time to reperfusion.

In related methods, the compounds of the invention are useful for the prevention of a secondary ischemic event. In these methods, compounds of the invention or their pharmaceutical compositions are administered to a patient who has suffered a primary ischemic event in an amount sufficient to prevent or reduce the likely occurrence of a secondary event. Generally, the primary and/or secondary ischemic event is selected from myocardial infraction, stable or unstable angina, acute reocclusion after percutaneous transluminal coronary angioplasty, restenosis, thrombotic stroke, transient ischemic attack, reversible ischemic neurological deficit and intermittent claudication.

The compounds and pharmaceutical compositions of the invention may be utilized in vivo, ordinarily in mammals such as primates, (e.g., humans), sheep, horses, cattle, pigs, dogs, cats, rats and mice, or in vitro. The biological properties, as defined above, of a compound or a pharmaceutical composition of the invention can be readily characterized by methods that are well known in the art such as, for example, by in vivo studies to evaluate antithrombotic efficacy, and effects on hemostasis and hematological parameters.

Subjects (typically mammalian) in need of treatment using the compounds or pharmaceutical compositions of the invention may be administered dosages that will provide optimal efficacy. The dose and method of administration will vary from subject to subject and be dependent upon such factors as the type of mammal being treated, its sex, weight, diet, concurrent medication, overall clinical condition, the particular compound of formulae I, Ia, Ib, Ic or Id employed, the specific use for which the compound or pharmaceutical composition is employed, and other factors which those skilled in the medical arts will recognize.

Therapeutically effective dosages may be determined by either in vitro or in vivo methods. For each particular compound or pharmaceutical composition of the invention, individual determinations may be made to determine the optimal dosage required. The range of therapeutically effective dosages will be influenced by the route of administration, the therapeutic objectives and the condition of the patient. For injection by hypodermic needle, it may be assumed the dosage is delivered into the bodily fluids. For other routes of administration, the absorption efficiency must be individually determined for each compound by methods well known in pharmacology. Accordingly, it may be necessary for the therapist to titer the dosage and modify the route of administration as required to obtain the optimal therapeutic effect.

The determination of effective dosage levels, that is, the dosage levels necessary to achieve the desired result, i.e., platelet ADP receptor inhibition, will be readily determined by one skilled in the art. Typically, applications of a compound or pharmaceutical composition of the invention are commenced at lower dosage levels, with dosage levels being increased until the desired effect is achieved. The compounds and compositions of the invention may be administered orally in an effective amount within the dosage range of about 0.01 to 1000 mg/kg in a regimen of single or several divided daily doses. If a pharmaceutically acceptable carrier is used in a pharmaceutical composition of the invention, typically, about 5 to 500 mg of a compound of formulae I, Ia, Ib, Ic or Id, is compounded with a pharmaceutically acceptable carrier as called for by accepted pharmaceutical practice including, but not limited to, a physiologically acceptable vehicle, carrier, excipient, binder, preservative, stabilizer, dye, flavor, etc. The amount of active ingredient in these compositions is such that a suitable dosage in the range indicated is obtained.

The following preparations and examples are given to enable those skilled in the art to more clearly understand and to practice the present invention. They should not be considered as limiting the scope of the invention, but merely as being illustrative and representative thereof.

EXAMPLES

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1–15; *Rodd's Chemistry of Carbon Compounds*, Elsevier Science Publishers, 1989, Volumes 1–5 and Supplementals; and *Organic Reactions*, Wiley & Sons: New York, 1991, Volumes 1–40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Example 1

2-Amino-4-(benzyl-tert-butoxycarbonyl-amino)-benzoic acid methyl ester

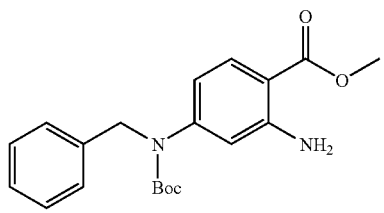

To a suspension of CsCO$_3$ (4.9 g, 15 mmoles) and (4-tert-Butoxycarbonylamino-2-nitro-benzoic acid methyl ester (2.96 g, 10 mmoles) in anhydrous DMF (100 mL) was added benzyl bromide (2.57 g, 15 mmoles) and the resulting mixture was stirred at room temperature for 12 hrs. The reaction mixture was filtered, concentrated, diluted with ethyl acetate, and washed with 5% citric acid, saturated NaHCO$_3$ solution and water. The organic phase was hydrogenated over 10% Pd/C in EtOAc. After 12 hr, the mixture was filtered through a celite pad, and the filtrate was concentrated in vacuo to give a crude oil which was purified by column chromatography to furnish the desired product as an off-white solid (2.05 g, 57% yield). ES$^+$ MS showed 357 m/z, the correct mass for the product. $^1$H NMR (400 MHz, DMSO-d$_6$) showed β=1.34 (s, 9H), 3.71 (s, 3H), 4.74 (s, 2H), 6.39 (d, J=9 Hz, 1H), 6.62 (s, 1+2H), 7.19 (d, J=7 Hz, 2H), 7.24 (d, J=7 Hz, 1H), 7.32 (dd, J$_1$=J$_2$=7 Hz, 2H),.

Example 2

[3-(4-Amino-phenyl)-2,4-dioxo-1,2,3,4-tetrahydro-quinazolin-7-yl]-benzyl-carbamic acid tert-butyl ester

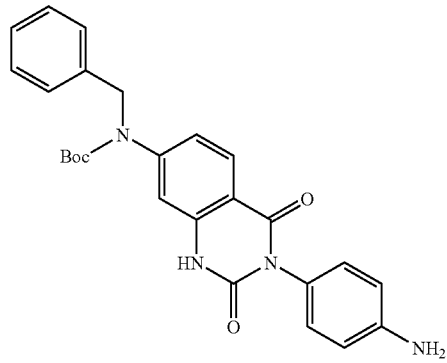

A solution of 2-Amino-4-(benzyl-tert-butoxycarbonyl-amino)-benzoic acid methyl ester (890 mg, 2.5 mmoles) and 4-nitrophenyl isocyanate (0.45 g, 2.75 mmoles) in the mixture of toluene (8 mL) and DMF (15 mL) was heated to 90° C. and stirred for 24 hrs. After filtration, the intermediate in the solution was hydrogenated over 10% Pd/C in EtOAc. When the reaction completed (12–24 hrs), the mixture was filtered through a celite pad, and the filtrate was concentrated in vacuo to give a crude solid which was purified by high pressure liquid chromatography to furnish compound 6 as a off-white solid (813 mg). ES$^+$ MS showed 459 m/z, the correct mass for the product. $^1$H NMR (400 MHz, DMSO-d$_6$) showed β=1.40 (s, 9H), 4.90 (s, 2H), 5.19 (s, 2H), 6.55 (d, J=8 Hz, 2H), 6.82 (d, J=8 Hz, 2H), 7.08 (s, 1H), 7.09 (d, J=8 Hz, 1H), 7.19 (d, J=7 Hz, 2H), 7.24 (d, J=7 Hz, 1H), 7.32 (dd, J$_1$=J$_2$=7 Hz, 2H), 11.31 (s, 1H).

Example 3

5-Chloro-N-[({4-(7-Benzylamino-2,4-dioxo-1,4-dihydro-2H-quinazolin-3-yl}-phenylamino)carbonyl]thiophene-2-sulfonamide

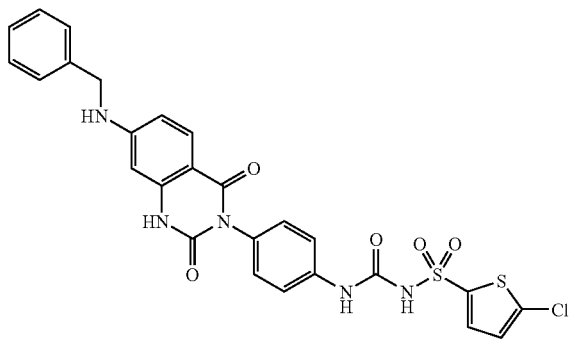

To a suspension of [3-(4-Amino-phenyl)-2,4-dioxo-1,2,3,4-tetrahydro-quinazolin-7-yl]-benzyl-carbamic acid tert-butyl ester (92 mg, 0.2 mmol) and 5-Chloro-thiophene-2-sulfonamide ethylcarbonate (60 mg, 0.22 mmol) in toluene (8 mL) was heated at reflux for 3 hours. The reaction mixture was concentrated and dried under vacuum. The residue was treated with 90% TFA with water for 20 minutes. After TFA was evaporated, purification with high pressure liquid chromatography furnished a colorless powder. ES+ MS showed 582 m/z and ES− MS 580 m/z, the correct mass for the product. $^1$H NMR (400 MHz, DMSO-$d_6$) δ (ppm): 4.31 (d, J=6 Hz, 2H), 6.18 (s, 1H), 6.48 (d, J=9 Hz, 1H), 7.08 (d, J=9 Hz, 2H), 7.22 (m, 2H), 7.32 (m, 4H), 7.41 (m, 3H), 7.55 (d, J=9 Hz, 1H), 7.60 (m, 1H), 9.06 (s, 1H), 11.05 (s, 1H).

Example 4 tert-butyl 4-fluorobenzyl(3-(4-amino-3-methylphenyl)-2,4-dioxo-1,2,3,4-tetrahydroquinazolin-7-yl)carbamate

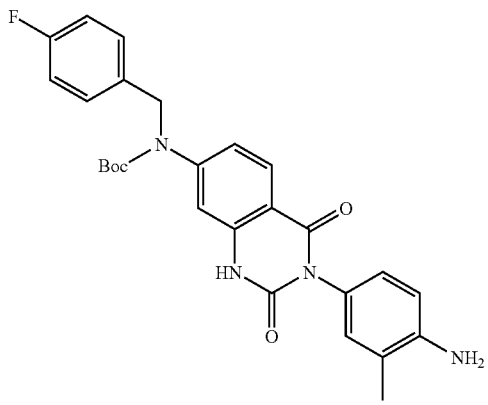

A solution of 3-methyl-4-nitroaniline (231 mg, 1.52 mmol) and triethylamine (0.42 mL, 3.04 mmol) in dichloromethane (10 mL) was added slowly to a suspension of disuccinylcarbonate (389 mg, 1.52 mmol) in dichloromethane (10 mL) during which time the suspension became homogeneous. The reaction was stirred until all starting aniline was consumed, then treated with the aniline prepared from 4-fluorobenyl bromide using procedure described in example 1 (300 mg, 1.17 mmol) and stirred at rt overnight. The reaction mixture was concentrated to dryness, then diluted with DMF and heated to 90° C. for 4 hrs at which time it was cooled to rt, diluted with water which was then extrated twice with ethyl acetate and the combined organic layers then dried over magnesium sulfate. After concentration, the crude product was purified by silica gel chromatography. The resulting yellow solid was then reduced as described in Example 2 affording 10 mg of the desired aniline (10% yield, 2 steps). ES+ MS showed 491 m/z, the correct mass for the product. $^1$H NMR (400 MHz, CDCl$_3$) showed δ=1.40 (s, 9H), 2.20 (s, 3H), 4.83 (s, 2H), 6.73 (m, 1H), 6.86 (m, 7H), 7.13 (m, 2H), 7.99 (m, 2H), 10.08 (s, 1H).

Example 5

1-(4-(7-(4-fluorobenzylamino)-2,4-dioxo-1,2-dihydroquinazolin-3(4H)-yl)-2-methylphenyl)-3-(5-chlorothiophen-2-ylsulfonyl)urea

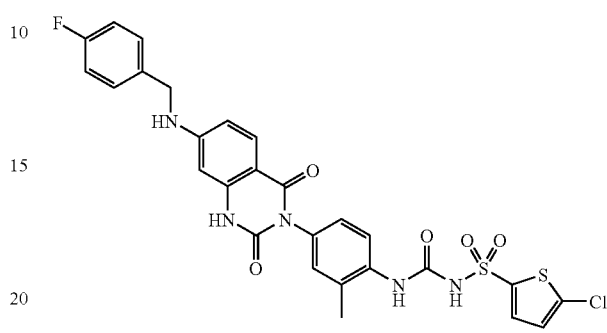

The aniline from example 4 was converted to the title compound using the experimental procedure described in example 3. ES+ MS showed 614 m/z, the correct mass for the product. $^1$H NMR (400 MHz, DMSO-$d_6$) showed δ=2.23 (s, 3H), 4.39 (s, 2H), 6.16 (s, 1H), 6.54 (d, 1H), 7.04 (m, 5H), 7.37 (m, 2H), 7.69 (m, 3H).

Example 6 tert-butyl 4-fluorobenzyl(3-(4-amino-3,5-dimethylphenyl)-2,4-dioxo-1,2,3,4-tetrahydroquinazolin-7-yl)carbamate

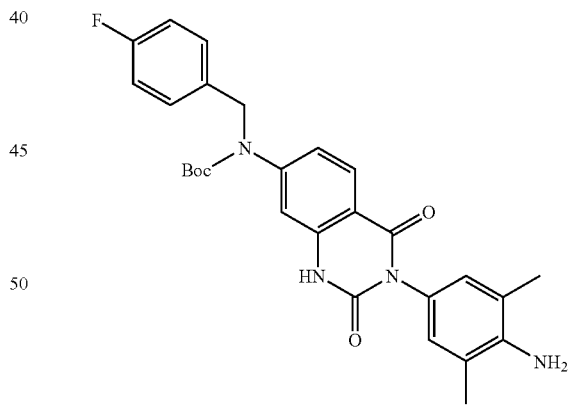

A solution of 3,5-dimethyl-4-nitroaniline (100 mg, 0.60 mmol) in THF (10 mL) was treated with 10% Palladium on carbon (Degussa, 10 mg) and stirred under an atmosphere of H$_2$ for five hours at which time it was filtered, concentrated and submitted to the conditions described for method B affording the title compound as an off-white solid (89 mg, 29% yield for 2 steps). ES+ MS showed 505 m/z, the correct mass for the product. $^1$H NMR (400 MHz, DMSO-$d_6$) showed δ=1.41 (s, 9H), 4.85 (s, 2H), 6.83 (s, 2H), 6.98 (m, 4H), 7.17 (m, 2H), 8.00 (d, 1H), 9.50 (br s, 1H).

Example 7

1-(4-(7-(4-fluorobenzylamino)-2,4-dioxo-1,2-dihydroquinazolin-3(4H)-yl)-2,6-dimethylphenyl)-3-(5-chlorothiophen-2-ylsulfonyl)urea

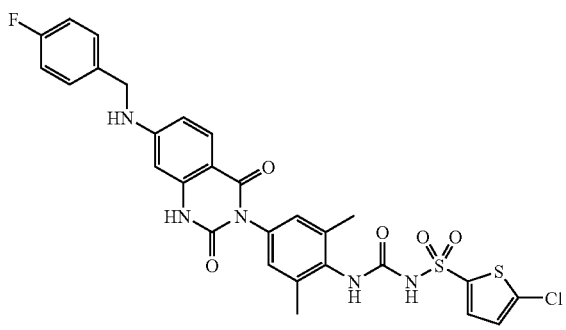

Disuccinylcarbonate (290 mg, 1.13 mmol) was suspended in dichloromethane (5 mL) and then treated with a solution of 5-chloro-2-thiophenesulfonamide (210 mg, 1.05 mmol) and tetramethylguanidine (0.22 mL, 1.74 mmol) in 5 mL dichloromethane during which time the reaction became homogeneous. The reaction mixture was stirred at rt overnight, then the solvent removed in vacuo and the residue suspended in acetonitrile and transferred to a flask containing the aniline from example 6 (440 mg, 0.87 mmol). The mixture was refluxed overnight, then cooled and diluted with aq ammonium chloride which was then extrated thrice with dichloromethane and concentrated to dryness. The crude producted was diluted with dichloromethane (10 mL) and treated with trifluoroacetic acid (10 mL) and stirred for 1 hr during which time a flocculant precipitate formed. The solvent was removed and the residue diluted with a small amount of acetonitrile and water resulting in a white ppt which was filtered and dried affording the desired product as a fluffy white solid. ES⁻ MS showed 626 m/z, the correct mass for the product. $^1$H NMR (400 MHz, DMSO-$d_6$) showed δ=2.03 (s, 6H), 4.29 (s, 2H), 6.18 (s, 1H), 6.48 (d, 1H), 6.90 (s, 2H), 7.19 (t, 2H), 7.26 (s, 1H), 7.38 (m, 3H), 7.57 (d, 1H), 7.65 (s, 1H), 8.21 (s, 1H), 11.09 (s, 1H).

Similarly, following the procedure described in Examples 1–3, but replacing benzyl bromide and 4-nitrophenyl isocyanate with other appropriate arylalkyl, heteroarylalkyl bromides and aryl isocyanates, and utilizing the modifications known to those skilled in the art, the additional compounds of the general Formula I were prepared (see Table 1):

TABLE 1

| Example | Structure | ES-MS(M − H)⁺ = |
|---------|-----------|-----------------|
| 8 | 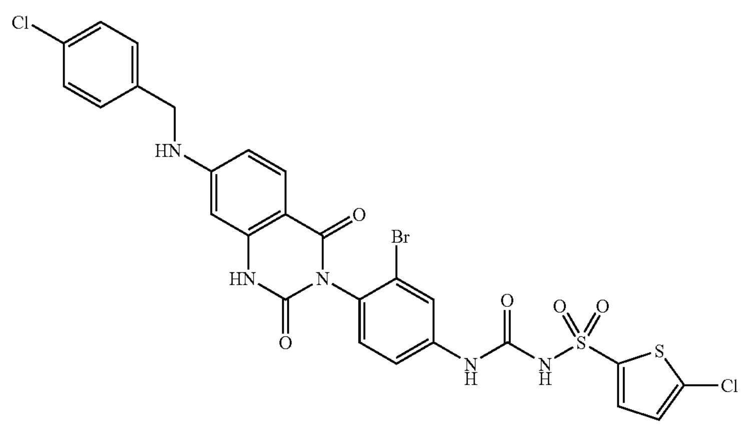 | 695 |
| 9 | 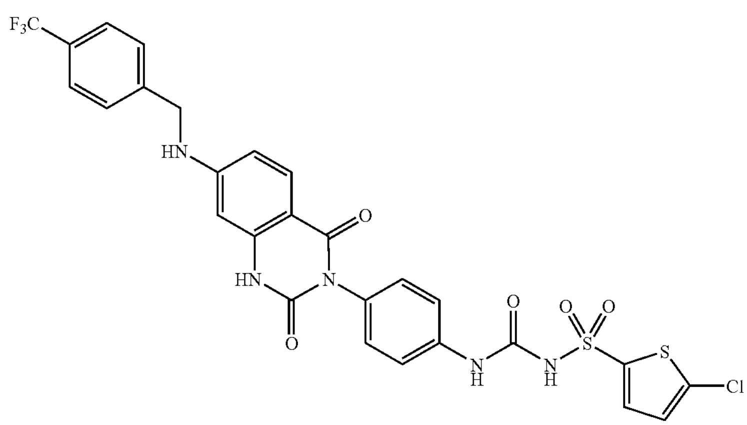 | 651 |

TABLE 1-continued
| Example | Structure | ES-MS(M − H)⁺ = |
|---|---|---|
| 10 | 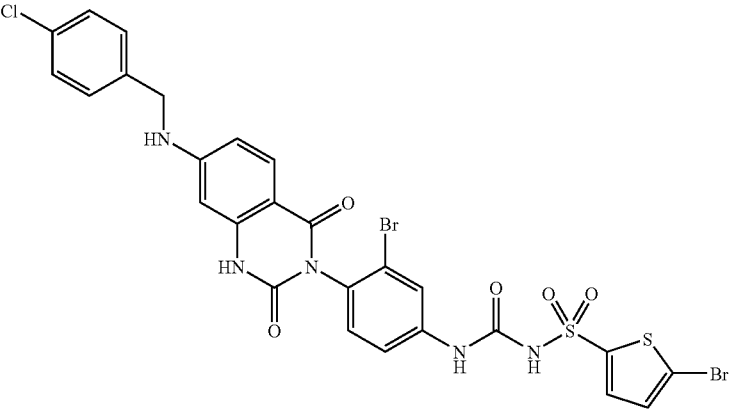 | 740 |
| 11 | 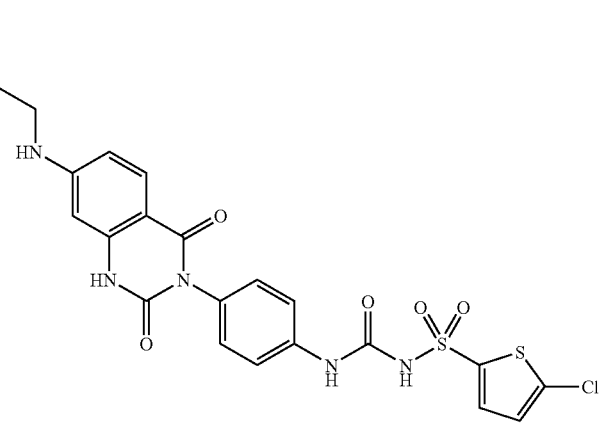 | 607 |
| 12 | 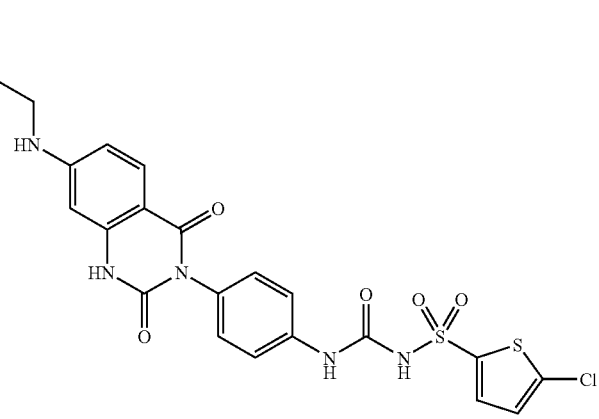 | 614 |

TABLE 1-continued

| Example | Structure | ES-MS(M − H)+ = |
|---|---|---|
| 13 | 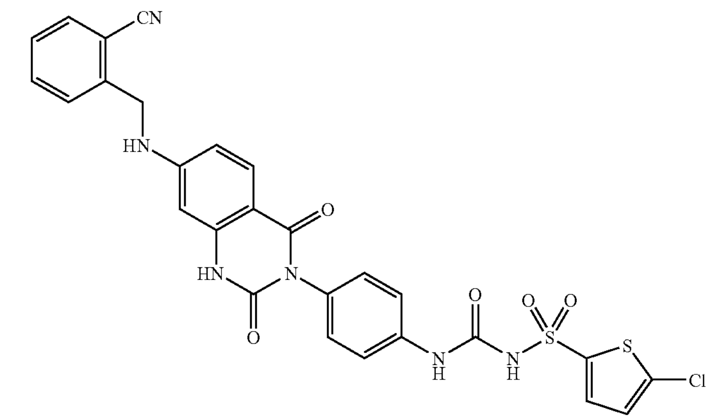 | 605 |
| 14 | 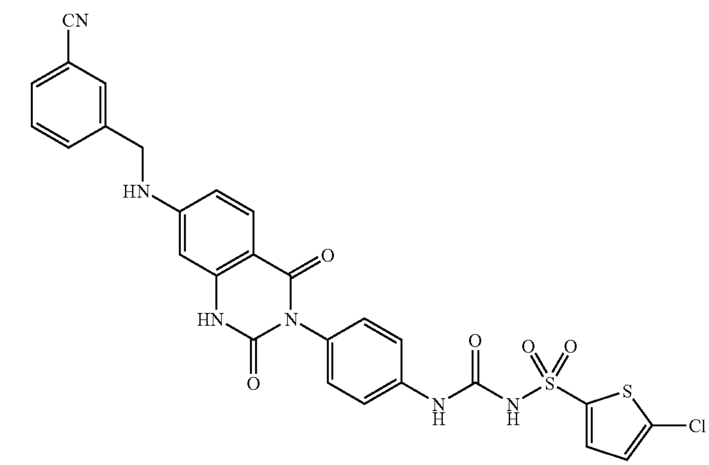 | 605 |
| 15 | 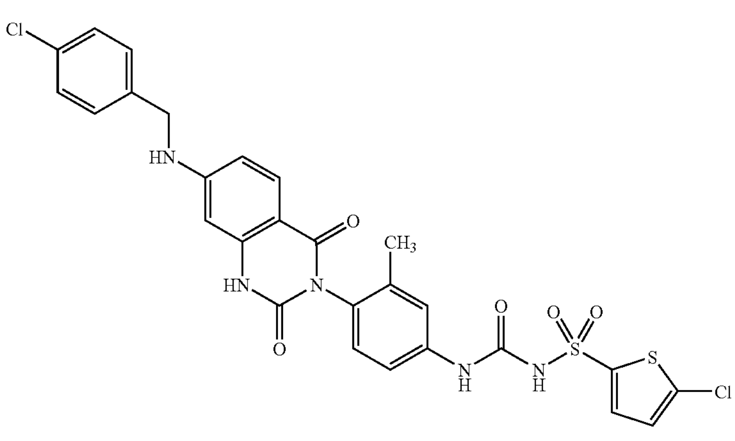 | 628 |

TABLE 1-continued

| Example | Structure | ES-MS(M − H)+ = |
|---|---|---|
| 16 | 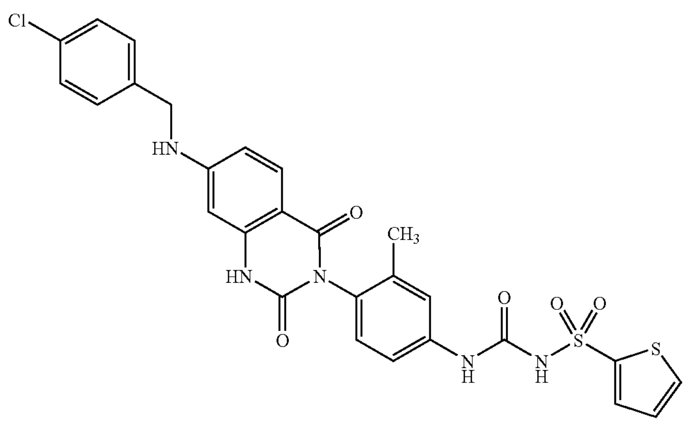 | 595 |
| 17 | 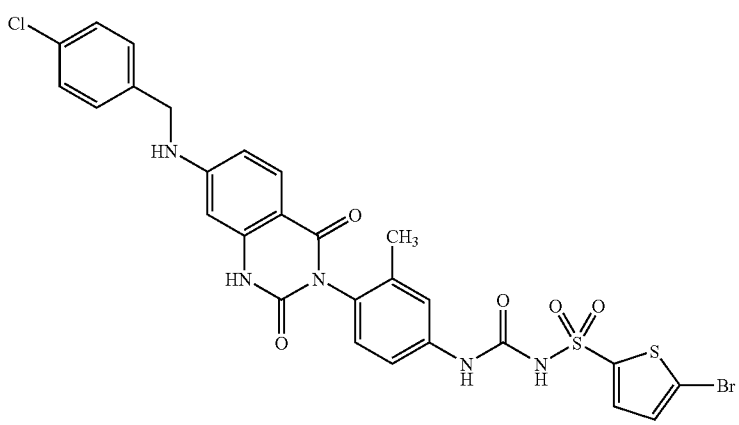 | 672 |
| 18 | 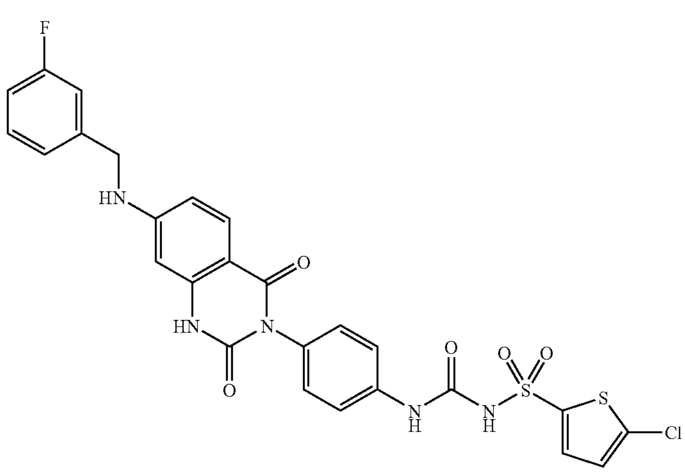 | 598 |

TABLE 1-continued

| Example | Structure | ES-MS(M − H)+ = |
|---|---|---|
| 19 | 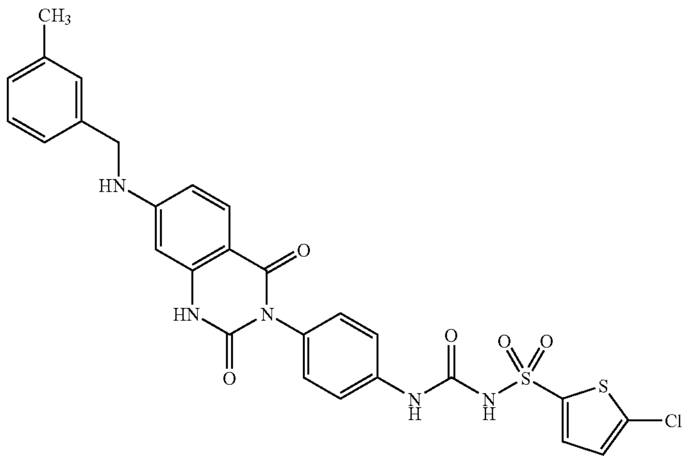 | 594 |
| 20 | 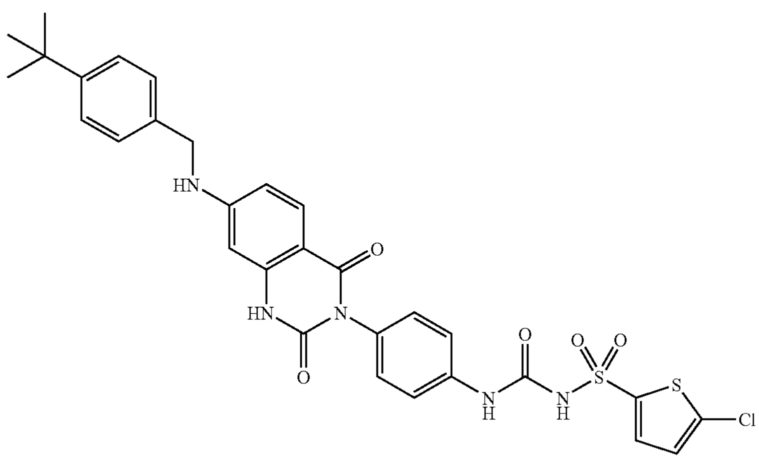 | 636 |
| 21 | 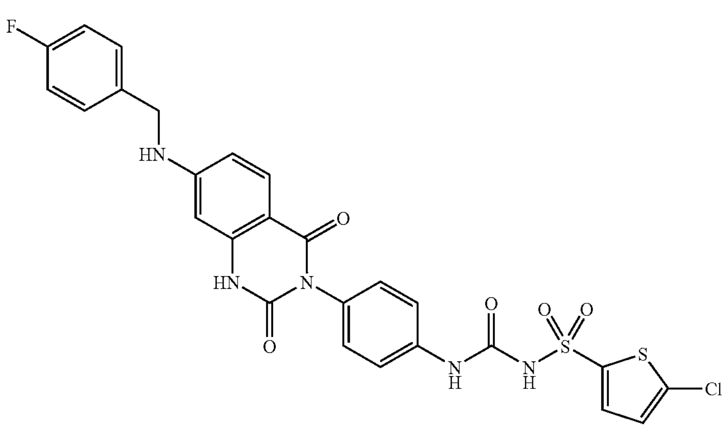 | 598 |

TABLE 1-continued

| Example | Structure | ES-MS(M − H)+ = |
|---|---|---|
| 22 | 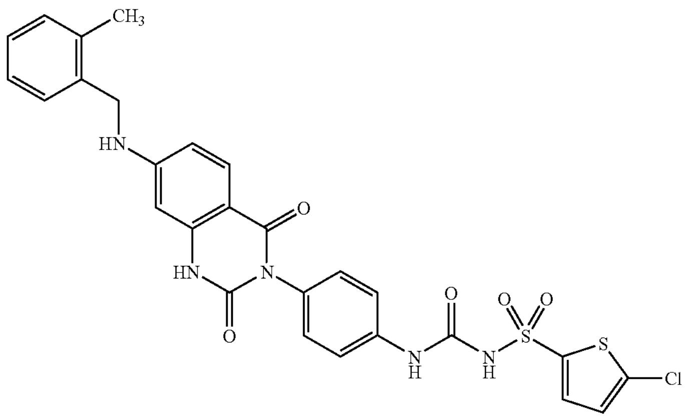 | 594 |
| 23 | 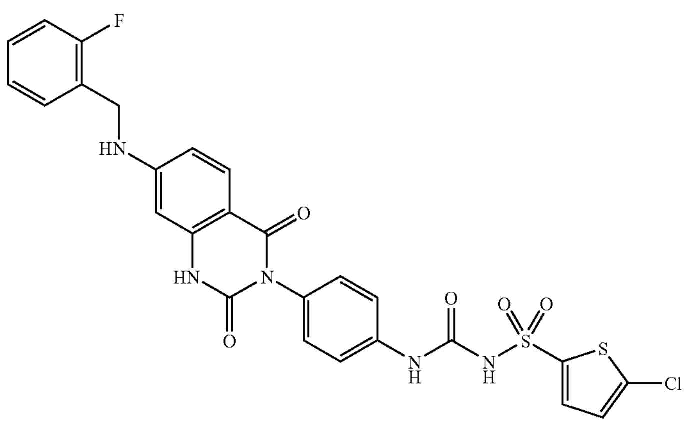 | 598 |
| 24 | 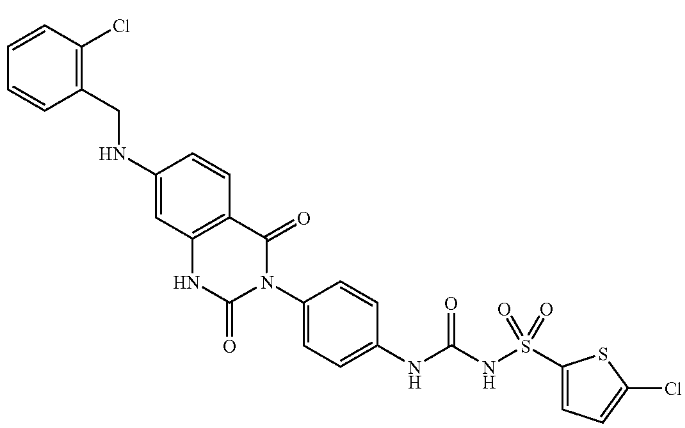 | 614 |

TABLE 1-continued

| Example | Structure | ES-MS(M − H)+ = |
| --- | --- | --- |
| 25 | 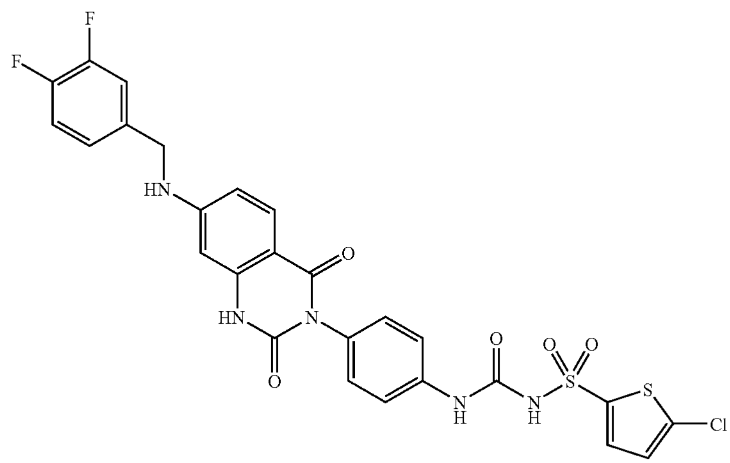 | 616 |
| 26 | 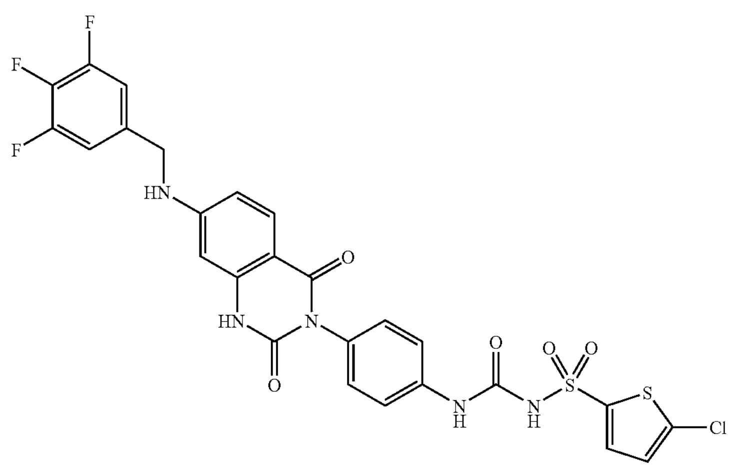 | 634 |
| 27 | 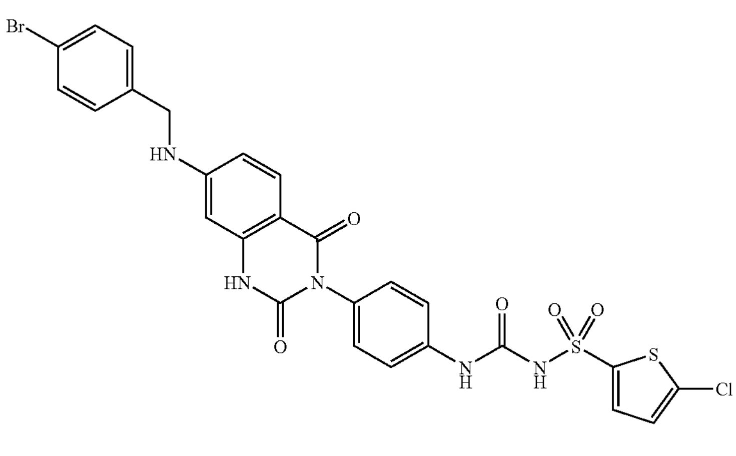 | 657 |

TABLE 1-continued

| Example | Structure | ES-MS(M − H)+ = |
|---|---|---|
| 28 | 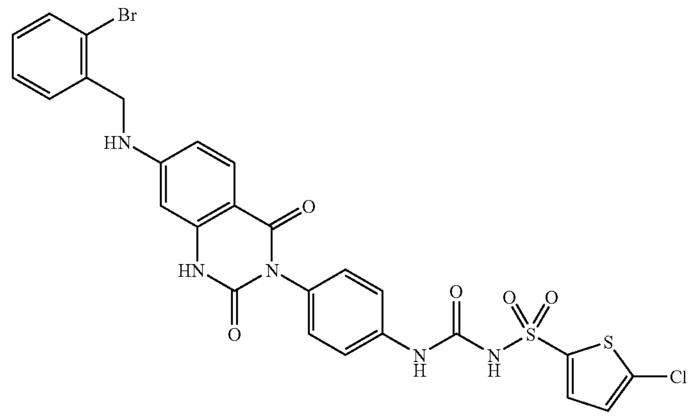 | 657 |
| 29 | 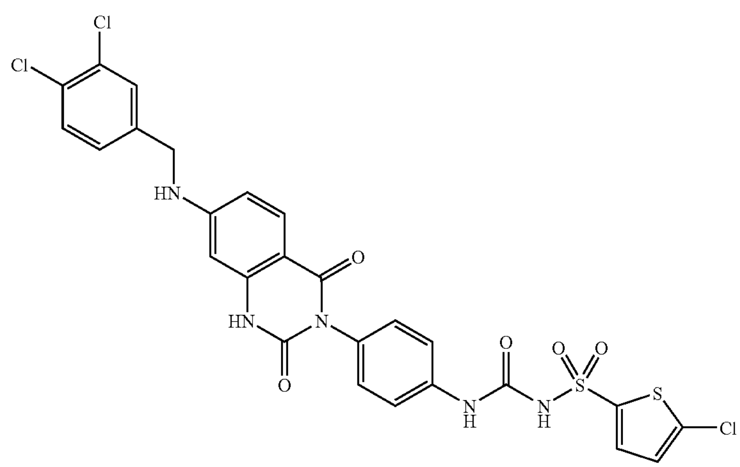 | 647 |
| 30 | 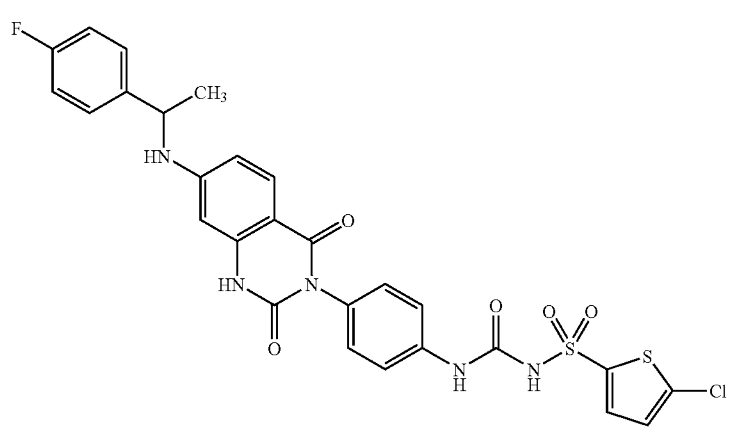 | 612 |

TABLE 1-continued

| Example | Structure | ES-MS(M − H)+ = |
|---|---|---|
| 31 | 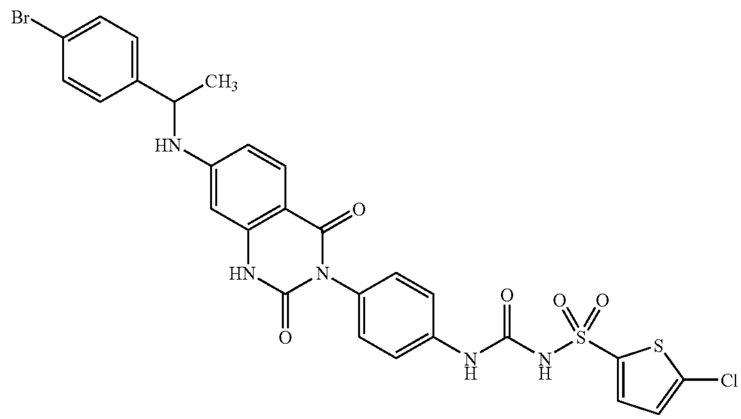 | 671 |
| 32 | 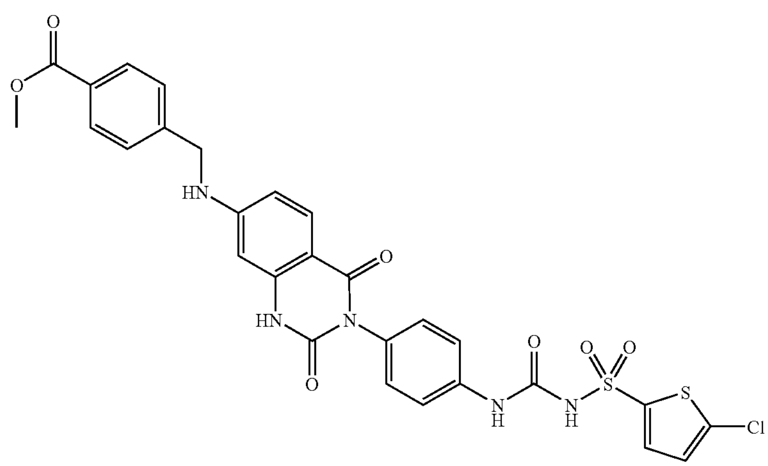 | 638 |
| 33 | 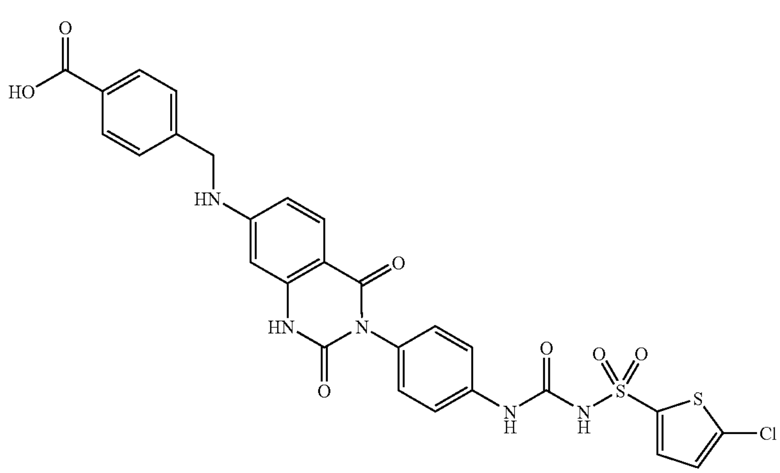 | 624 |

TABLE 1-continued

| Example | Structure | ES-MS(M − H)+ = |
|---|---|---|
| 34 | 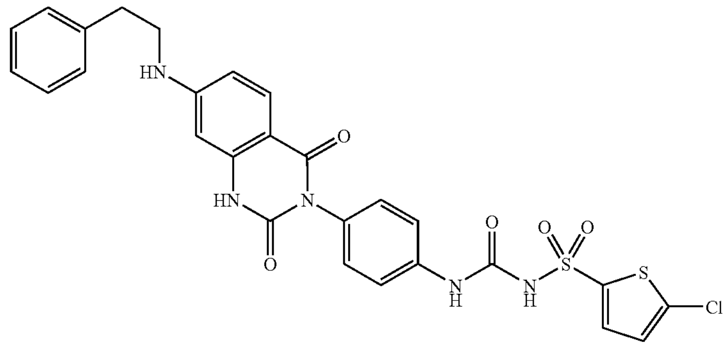 | 594 |
| 35 | 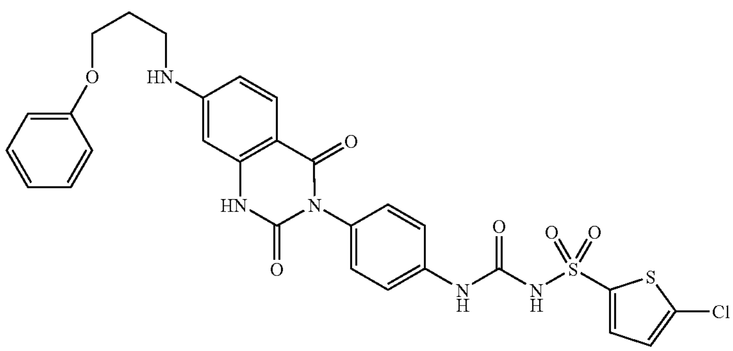 | 624 |
| 36 | 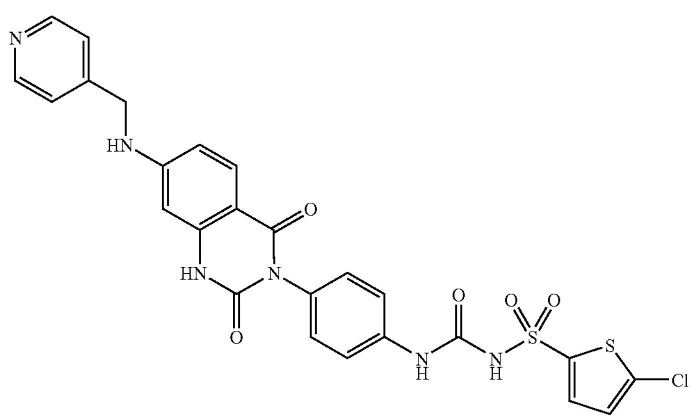 | 581 |
| 37 | 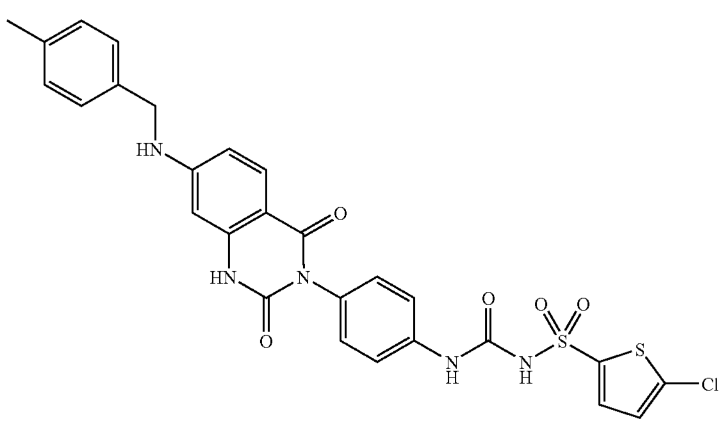 | 594 |

TABLE 1-continued

| Example | Structure | ES-MS(M − H)+ = |
|---|---|---|
| 38 | 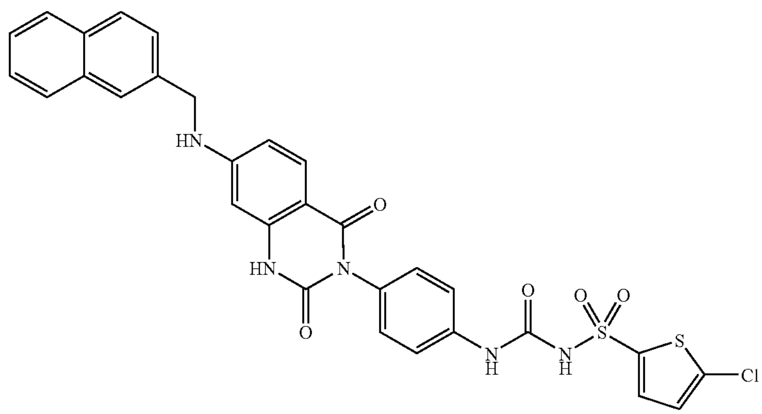 | 630 |
| 39 | 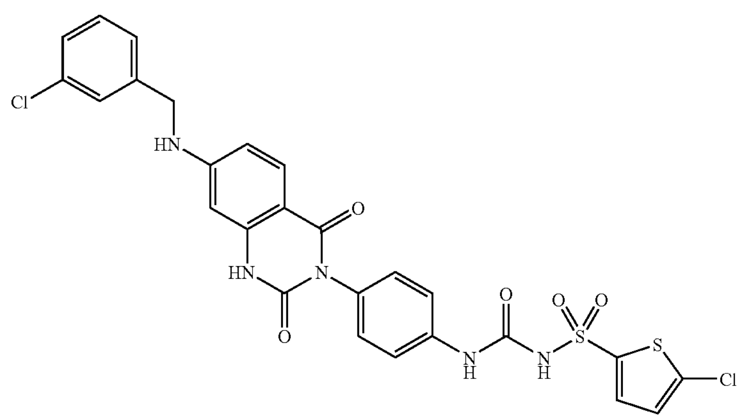 | 614 |
| 40 | 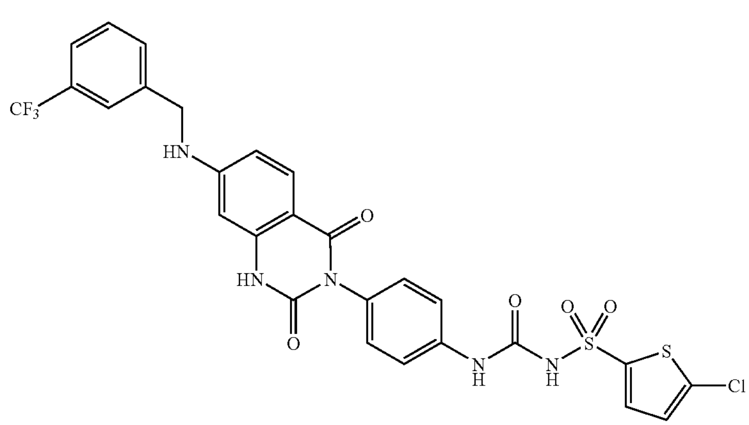 | 648 |

TABLE 1-continued

| Example | Structure | ES-MS(M − H)⁺ = |
|---|---|---|
| 41 | 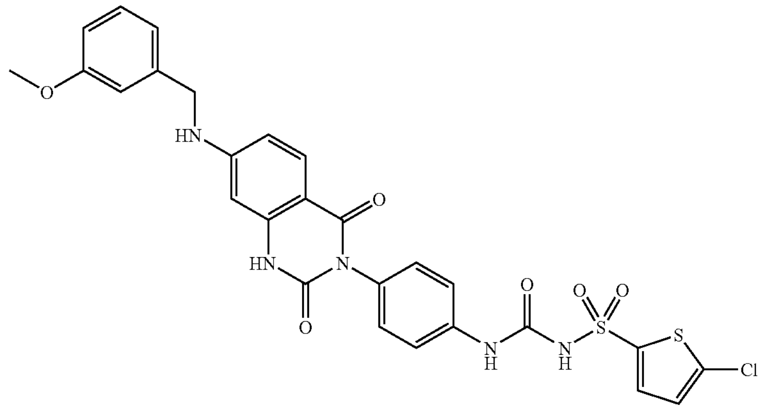 | 610 |
| 42 | 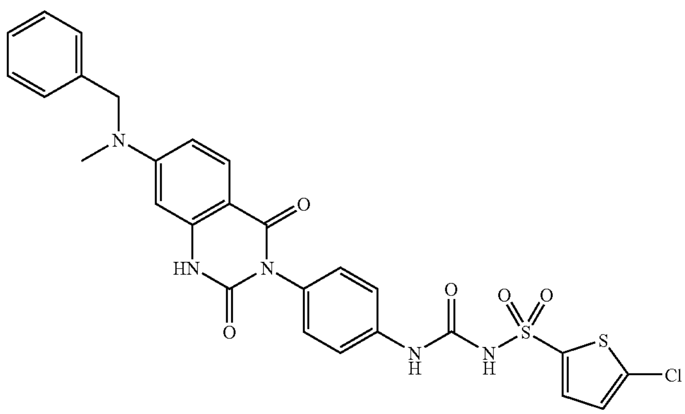 | 594 |
| 43 | 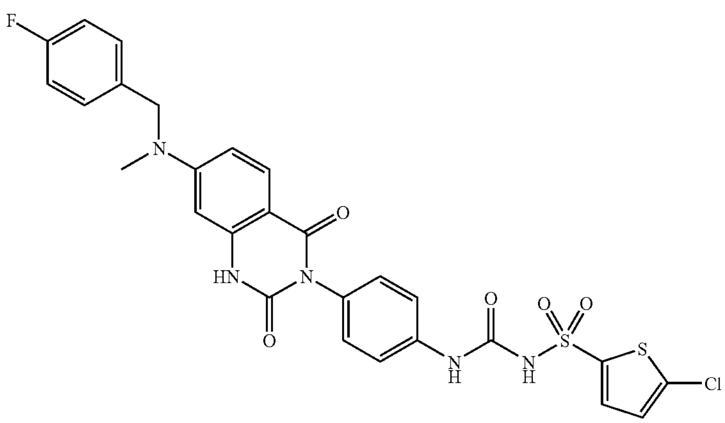 | 612 |

TABLE 1-continued

| Example | Structure | ES-MS(M − H)+ = |
|---|---|---|
| 44 | 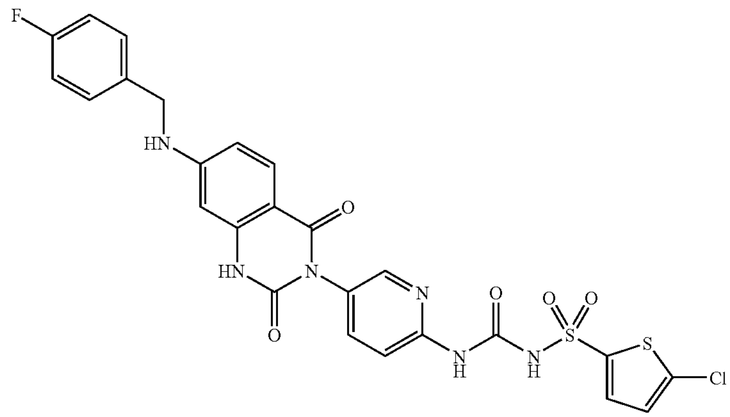 | 599 |

Example 45

2-Amino-4-(tert-butoxycarbonylamino)-benzoic acid methyl ester

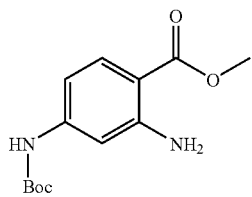

To a solution of 4-(tert-butoxycarbonylamino)-2-nitrobenzoic acid methyl ester (7.0 g, 23.6 mmoles) in 400 mL ethyl acetate was added 1.0 g 10% Pd/C. The reaction mixture was subjected to hydrogenation using a balloon for 24–36 hrs or until the reaction was complete as monitored by HPLC. The mixture was filtered through a celite bed, and the solid cake was thoroughly washed by ethyl acetate. The filtrate was concentrated in vacuo to dryness to afford the title compound (6.3 g, 99%). ES+ MS showed 267 m/z, the correct mass for the product.

Example 46 tert-Butyl 3-(4-aminophenyl)-1,2,3,4-tetrahydro-2,4-dioxoquinazolin-7-ylcarbamate

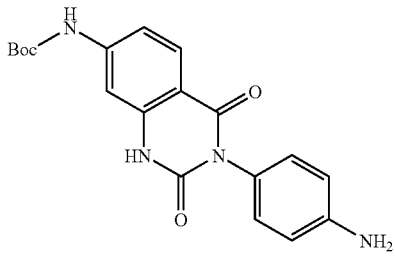

A solution of 2-amino-4-(tert-butoxycarbonylamino)-benzoic acid methyl ester (6.3 g, 23.6 mmol) and 4-nitrophenyl isocyanate (7.8 g, 47.4 mmoles) in 100 mL dry dimethylformamide was stirred at room temperature for 20 hrs. To it was then added diisopropylamine (8.2 mL, 47.4 mmol), and the reaction mixture was heated in 80° C. bath for 2 hrs. It was cooled to room temperature and the solid precipitates were filtered off. The dimethylformamide filtrate was concentrated in vacuo to evaporate the solvent. To the residue was added 400 mL dichloromethane. After stirred and swirled, the solid was isolated by filtration. This solid was then dissolved in 100 mL dimethylformamide and 200 mL methanol. To it was added 1.0 g 10% Pd/C, and the mixture was subjected to standard hydrogenation using a balloon for 20 hrs. It was filtered through a celite bed. The filtrate was concentrated in vacuo and purified using flash column to afford the title compound (4.1 g, 44%). ES+ MS showed 397 m/z, the correct mass for the product.

Example 47

5-Chloro-N-[(4-(7-amino-2,4-dioxo-1,4-dihydro-2H-quinazolin-3-yl)-phenylamino)carbonyl]thiophene-2-sulfonamide

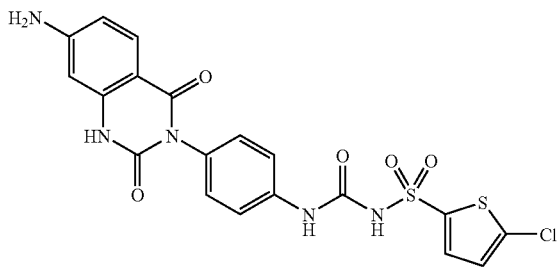

A mixture of tert-Butyl 3-(4-aminophenyl)-1,2,3,4-tetrahydro-2,4-dioxoquinazolin-7-ylcarbamate (4.0 g, 10 mmol) and 5-chlorothiophene-2-sulfonamide ethylcarbonate (3.0 g, 11 mmol) in 200 mL toluene was refluxed for 16 hrs. It was concentrated in vacuo. At room temperature, to this residue was added commercial 4N HCl dioxane (20 mL). The mixture was stirred for 1 h and concentrated in vacuo. The solid was triturated with dichloromethane. The solid was isolated by filtration and dried in vacuo. It was the title compound (2.6 g, 53%). ES+ MS showed 492 m/z and ES− MS 490 m/z, the correct mass for the product.

Example 48

5-Chloro-N-[(4-(7-(thiophen-2-yl)-amino-2,4-dioxo-1,4-dihydro-2H-quinazolin-3-yl)-phenylamino)carbonyl]thiophene-2-sulfonamide

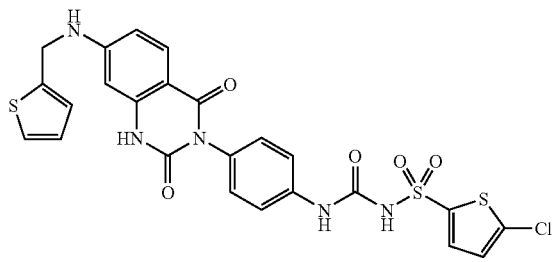

Compound 5-Chloro-N-[(4-(7-amino-2,4-dioxo-1,4-dihydro-2H-quinazolin-3-yl)-phenylamino)carbonyl]thiophene-2-sulfonamide (40 mg, 0.08 mmol) was dissolved in methyl sulfoxide (0.5 mL). To it was added acetic acid (1.0 mL) and thiophene-2-carbaldehyde (18 mg, 0.16 mmol). The mixture was stirred for 15 minutes at room temperature. To it was then added sodium cyanoborohydride (21 mg, 0.32 mmol). The mixture was stirred for 30 minutes and quenched with water (2 mL). The reaction mixture was then directly subjected to preparative HPLC purification to yield the title compound (26 mg, 55%). ES$^+$ MS showed 588 m/z and ES$^-$ MS 586 m/z, the correct mass for the product.

Similarly, following the procedure described in Examples 28–31, but replacing thiophene-2-carbaldehyde with other appropriate carbaldehydes, and utilizing the modifications known to those skilled in the art, the additional compounds of the general Formula I were prepared (see Table 2).

TABLE 2

| Example | Structure | ES-MS(M − H)$^-$ = |
|---|---|---|
| 49 | 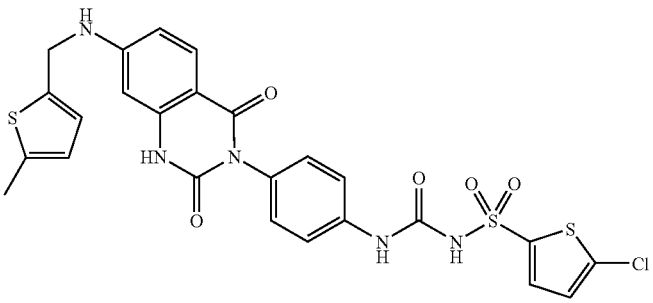 | 600 |
| 50 | 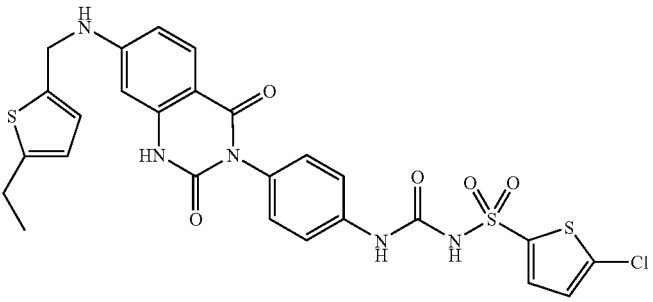 | 614 |
| 51 | 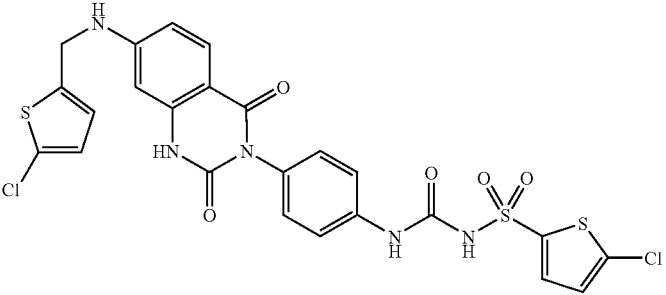 | 620 |

TABLE 2-continued

| Example | Structure | ES-MS(M − H)⁻ = |
|---------|-----------|------------------|
| 52 | 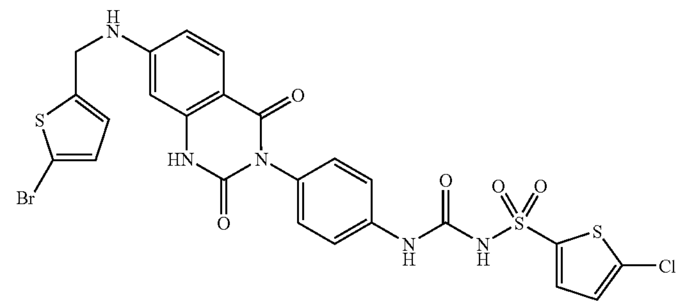 | 664 |
| 53 | 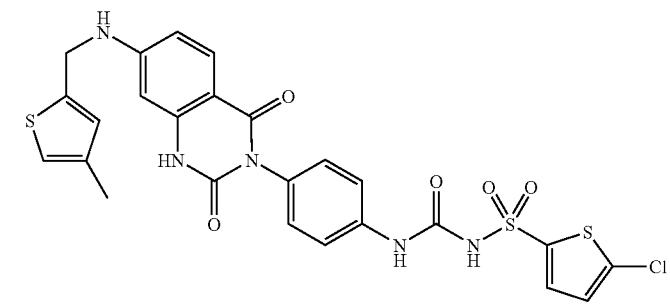 | 600 |
| 54 | 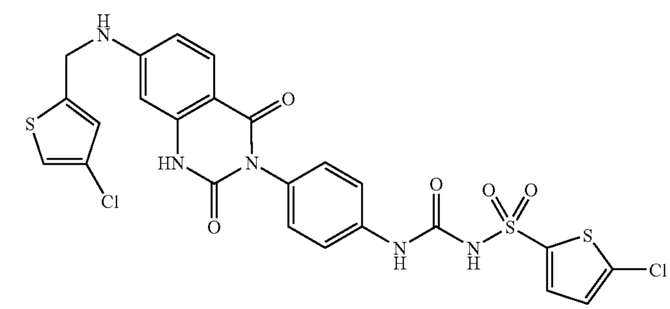 | 620 |
| 55 | 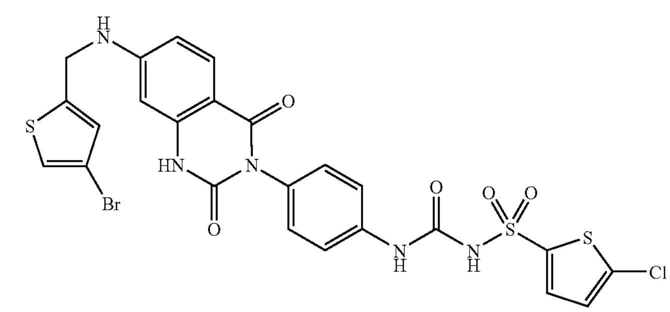 | 664 |
| 56 | 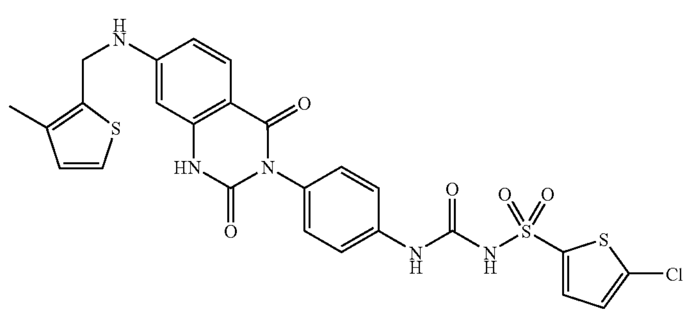 | 600 |

TABLE 2-continued

| Example | Structure | ES-MS(M − H)⁻ = |
|---|---|---|
| 57 | 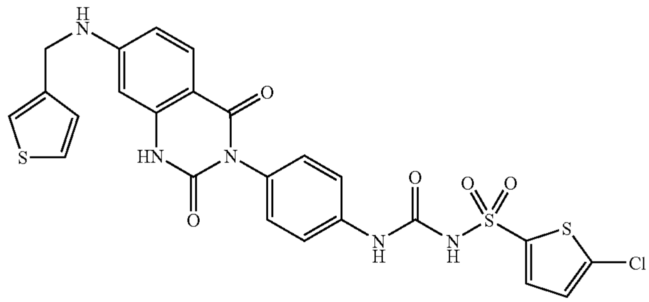 | 586 |
| 58 | 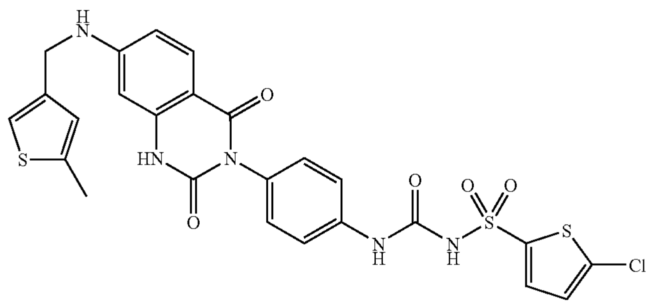 | 600 |
| 59 | 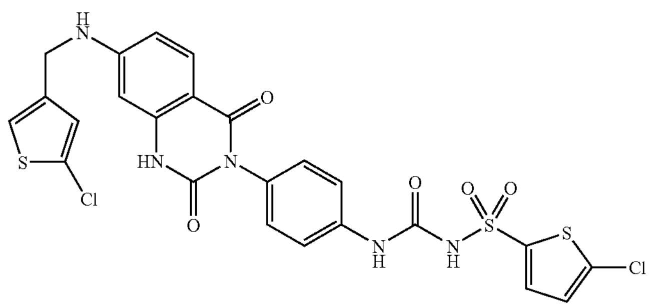 | 620 |
| 60 | 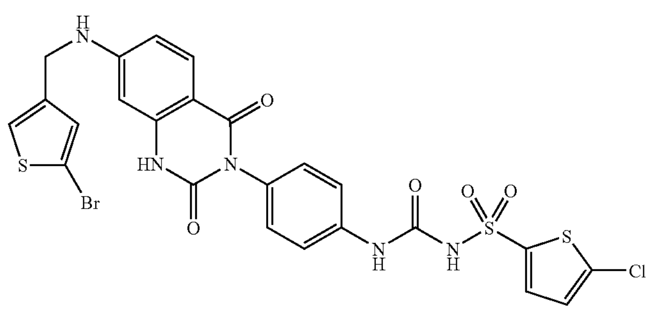 | 664 |
| 61 | 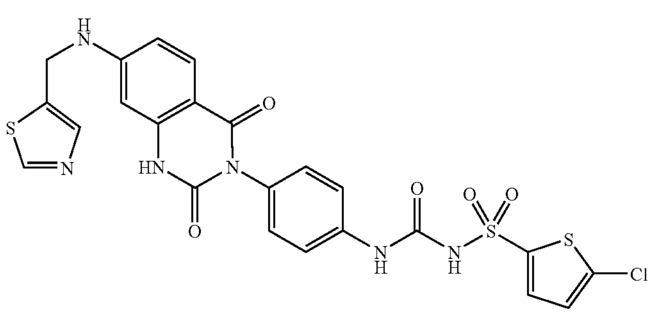 | 587 |

TABLE 2-continued

| Example | Structure | ES-MS(M − H)⁻ = |
|---|---|---|
| 62 | 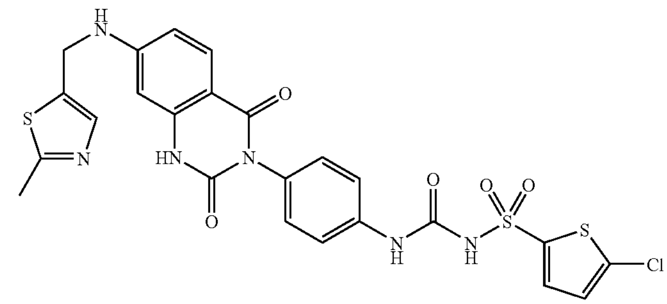 | 601 |
| 63 | 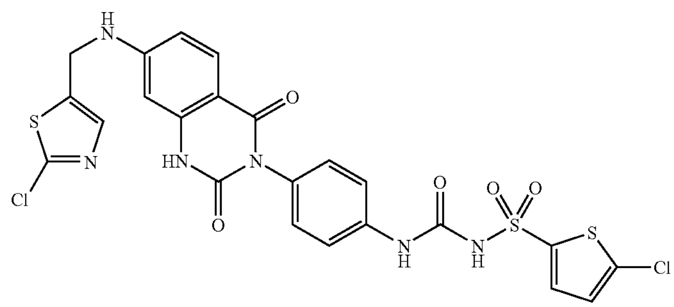 | 621 |
| 64 | 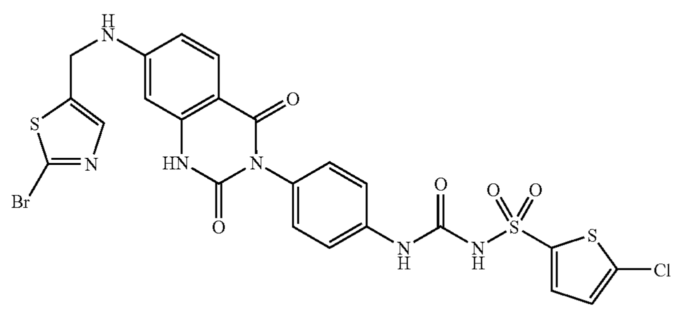 | 665 |
| 65 | 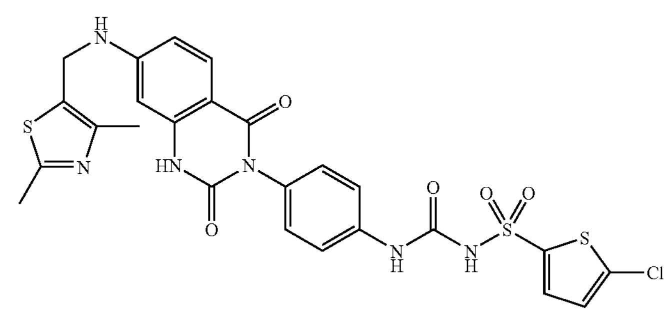 | 615 |
| 66 | 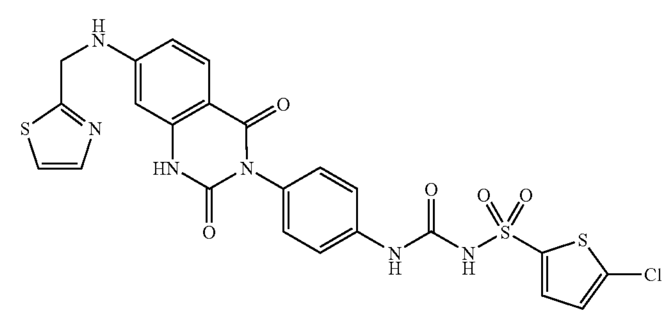 | 587 |

TABLE 2-continued

| Example | Structure | ES-MS(M − H)⁻ = |
|---|---|---|
| 67 | 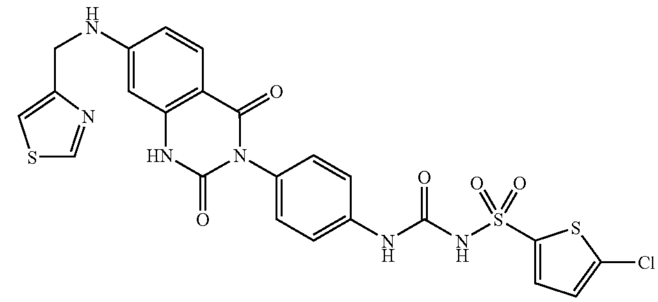 | 587 |
| 68 | 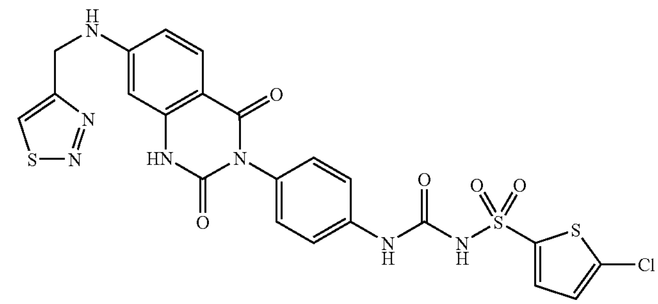 | 588 |
| 69 | 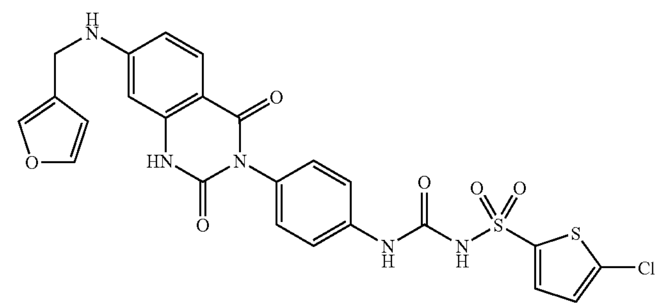 | 570 |
| 70 | 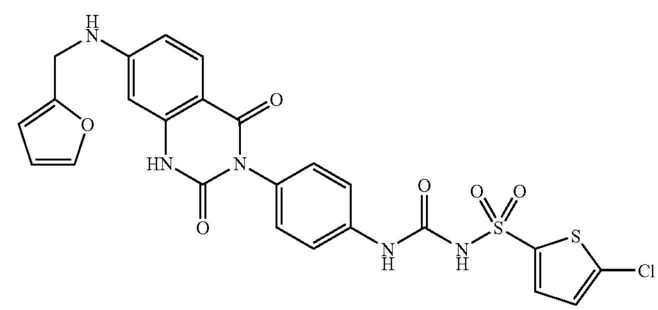 | 570 |
| 71 | 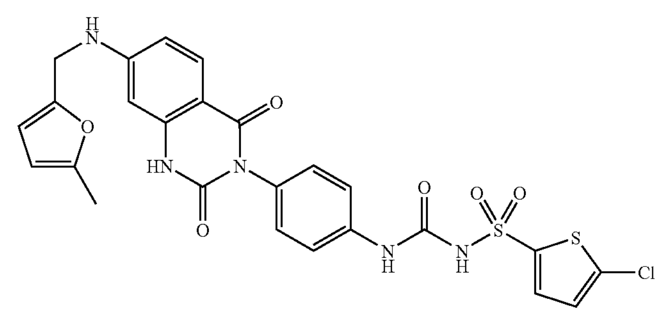 | 584 |

TABLE 2-continued

| Example | Structure | ES-MS(M − H)⁻ = |
|---|---|---|
| 72 | 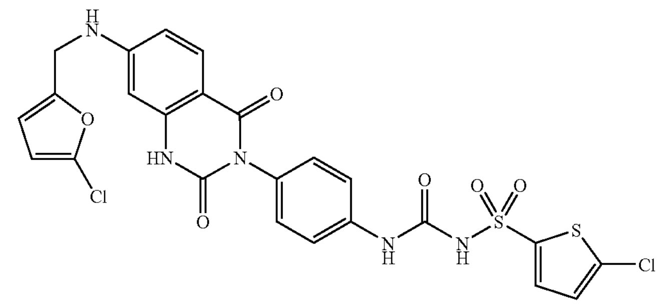 | 604 |
| 73 | 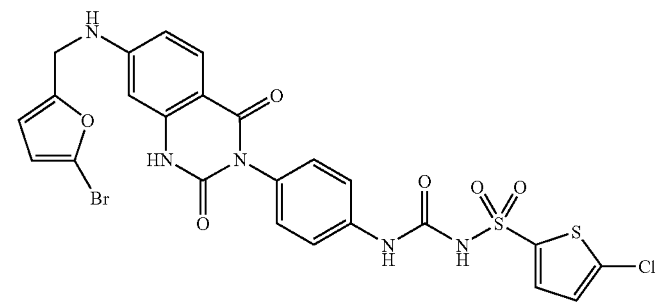 | 648 |
| 74 | 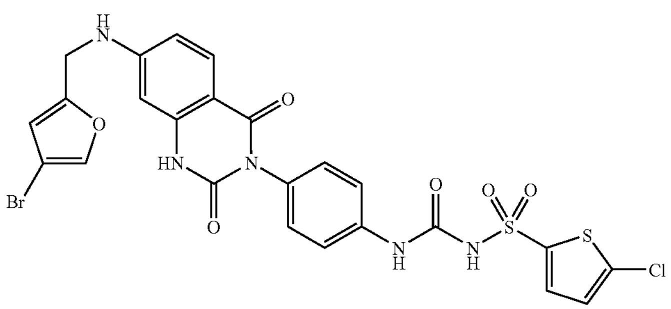 | 648 |
| 75 | 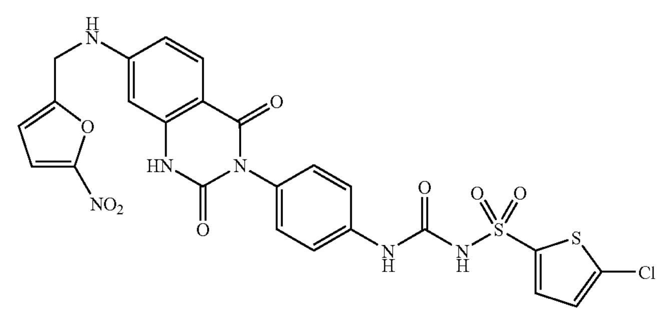 | 615 |
| 76 | 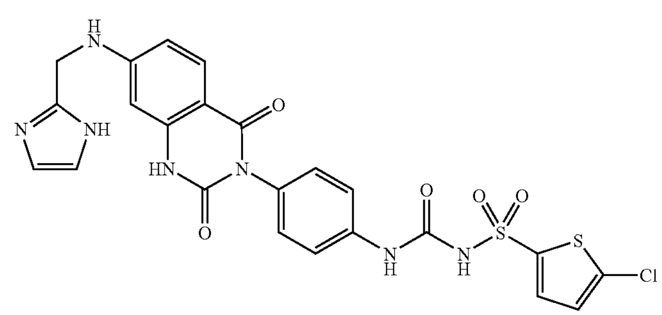 | 570 |

TABLE 2-continued
| Example | Structure | ES-MS(M − H)⁻ = |
|---|---|---|
| 77 | 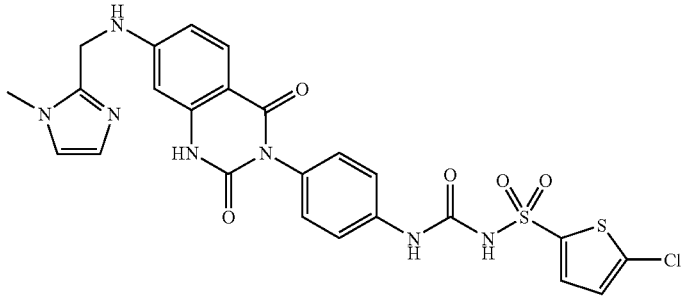 | 584 |
| 78 | 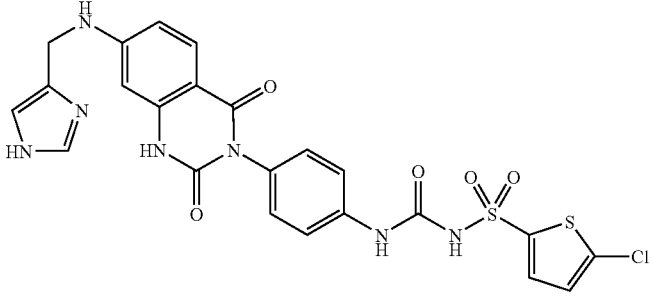 | 570 |
| 79 | 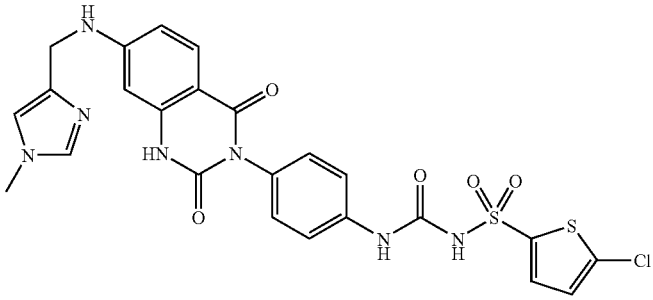 | 584 |
| 80 | 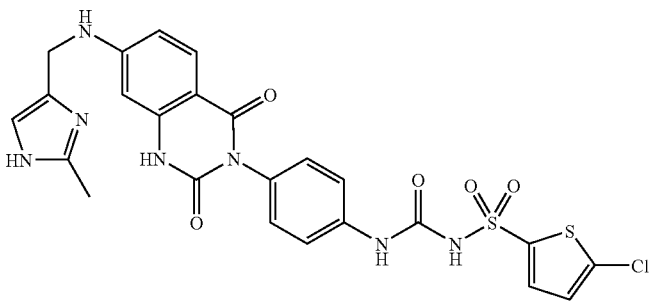 | 584 |
| 81 | 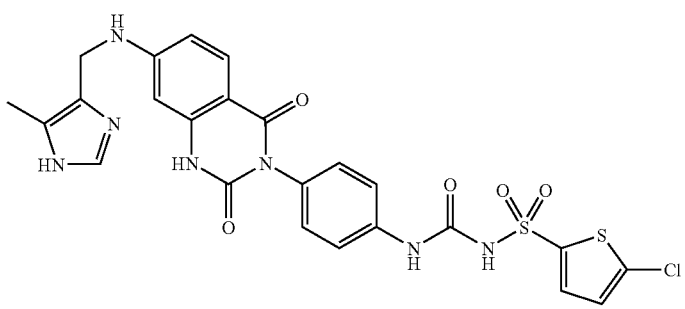 | 584 |

TABLE 2-continued

| Example | Structure | ES-MS(M − H)⁻ = |
|---|---|---|
| 82 | 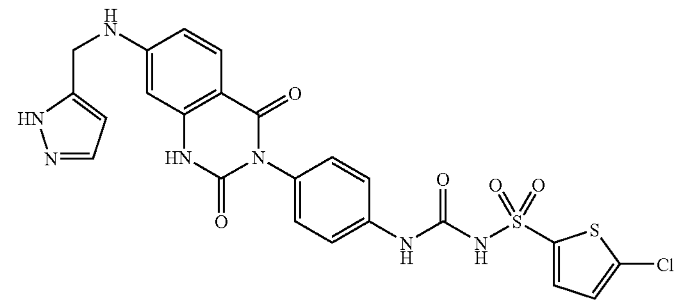 | 570 |
| 83 | 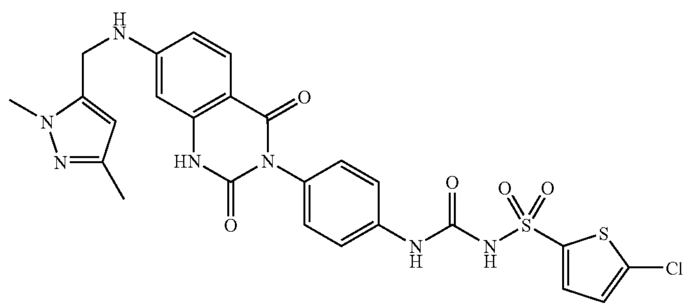 | 598 |
| 84 | 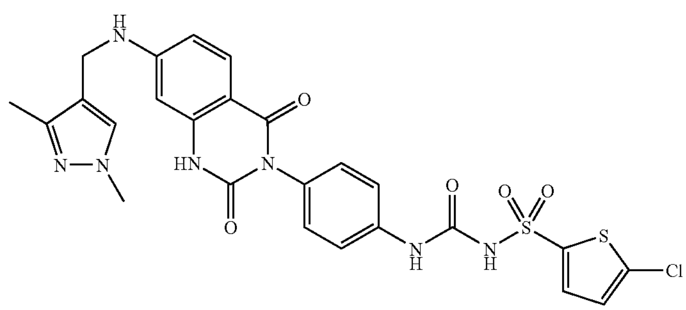 | 598 |
| 85 | 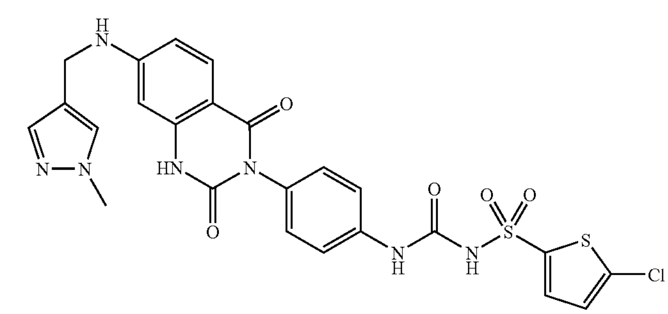 | 584 |
| 86 | 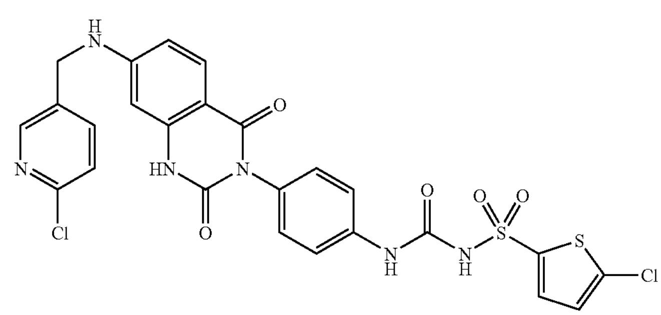 | 615 |

TABLE 2-continued

| Example | Structure | ES-MS(M − H)⁻ = |
|---|---|---|
| 87 | 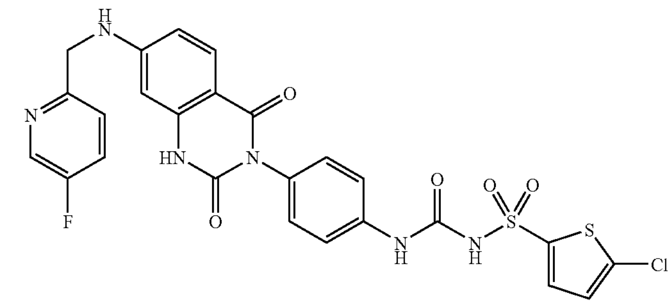 | 599 |
| 88 | 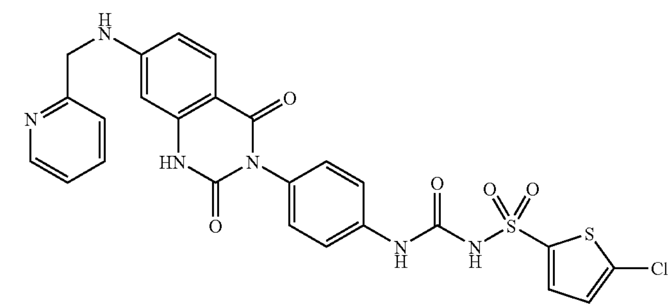 | 581 |
| 89 | 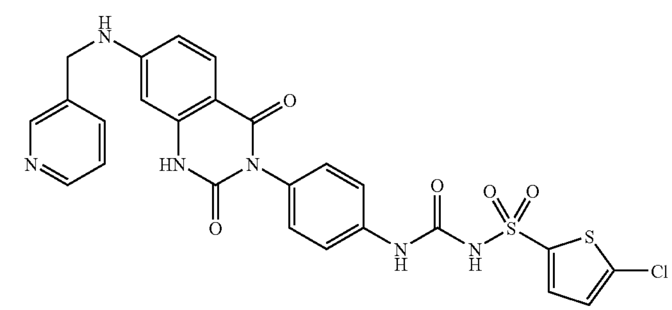 | 581 |
| 90 | 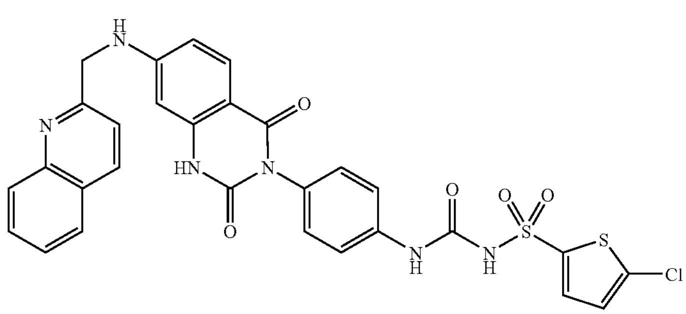 | 631 |
| 91 | 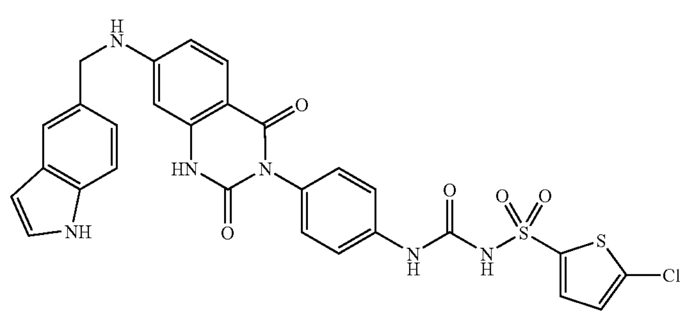 | 619 |

TABLE 2-continued

| Example | Structure | ES-MS(M − H)⁻ = |
|---------|-----------|-----------------|
| 92 | 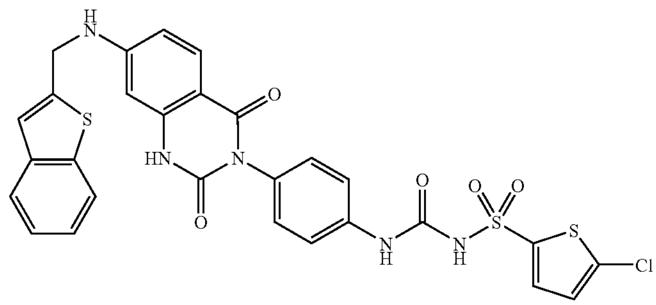 | 636 |
| 93 | 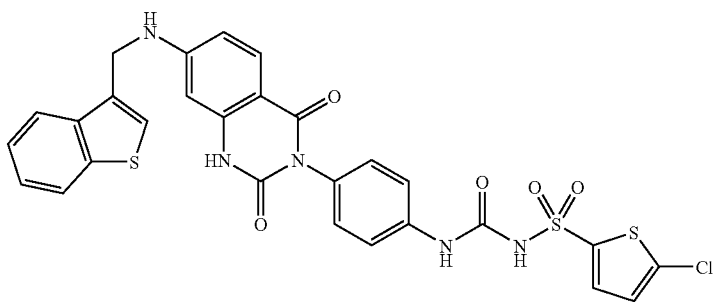 | 636 |
| 94 | 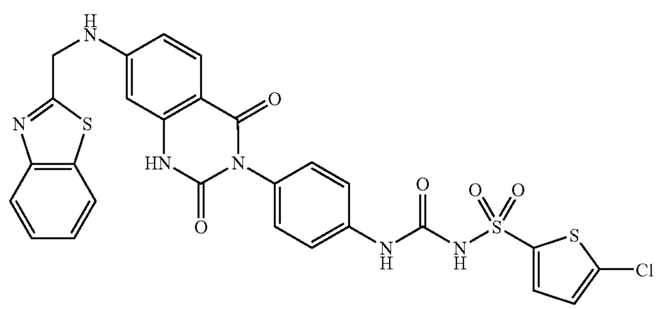 | 637 |
| 95 | 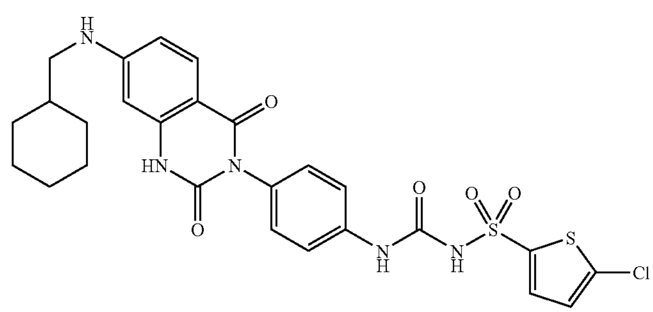 | 586 |
| 96 | 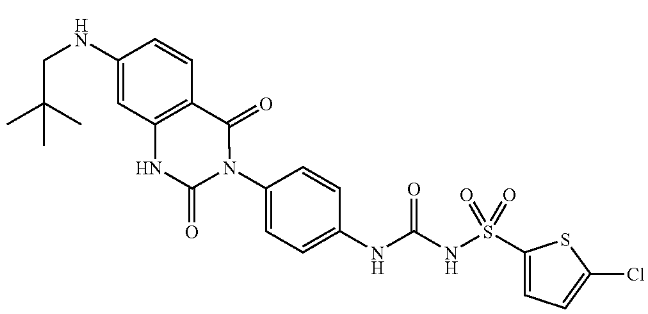 | 560 |

TABLE 2-continued

| Example | Structure | ES-MS(M − H)⁻ = |
|---|---|---|
| 97 | 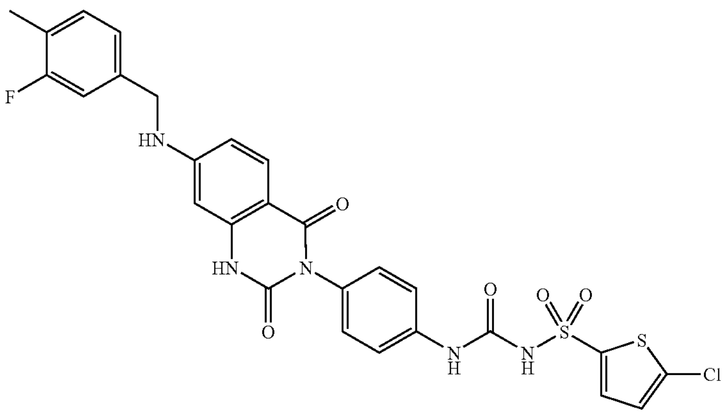 | 612 |
| 98 | 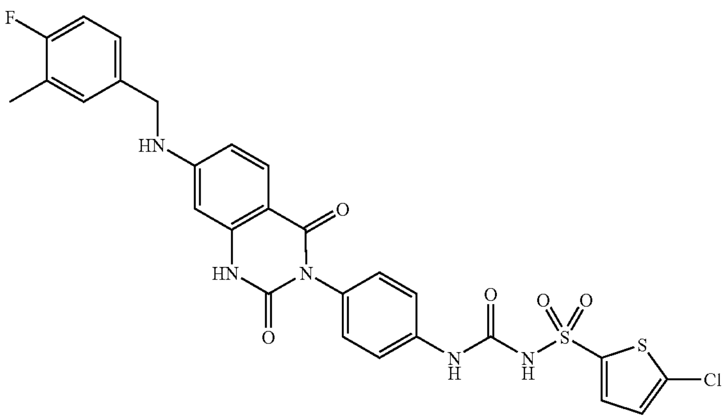 | 612 |
| 99 | 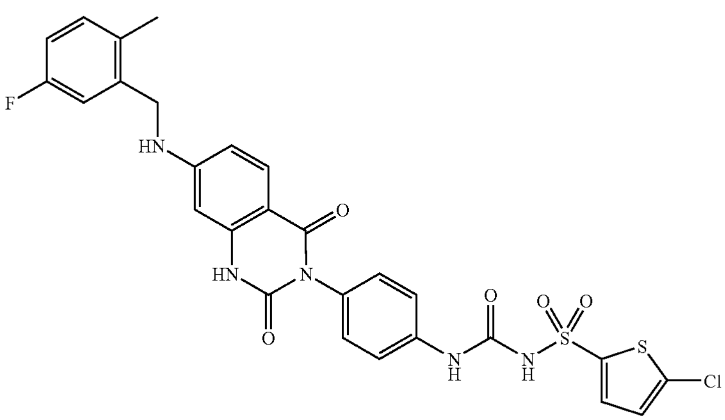 | 612 |

TABLE 2-continued

| Example | Structure | ES-MS(M − H)⁻ = |
|---|---|---|
| 100 | 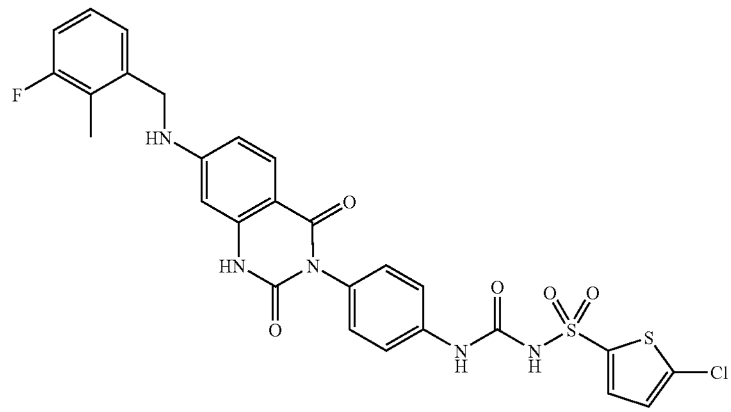 | 612 |
| 101 | 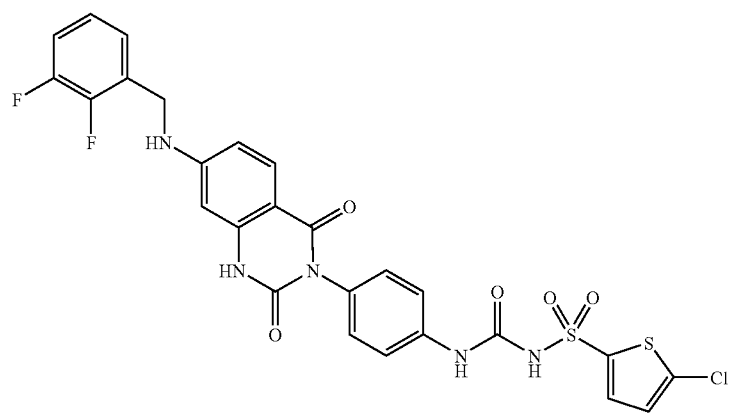 | 616 |
| 102 | 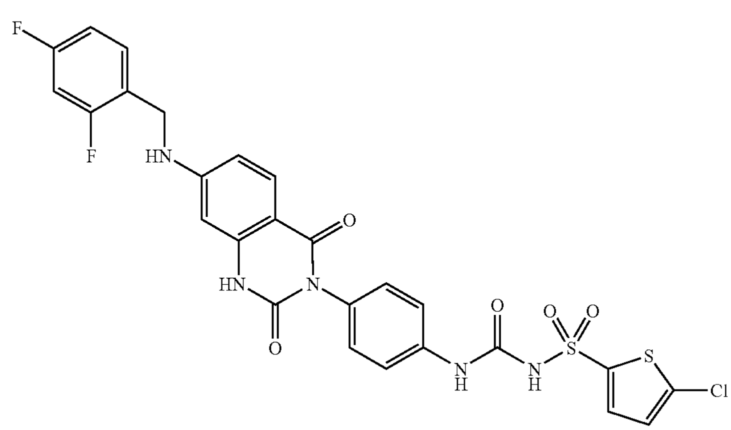 | 616 |

TABLE 2-continued

| Example | Structure | ES-MS(M − H)⁻ = |
|---|---|---|
| 103 | 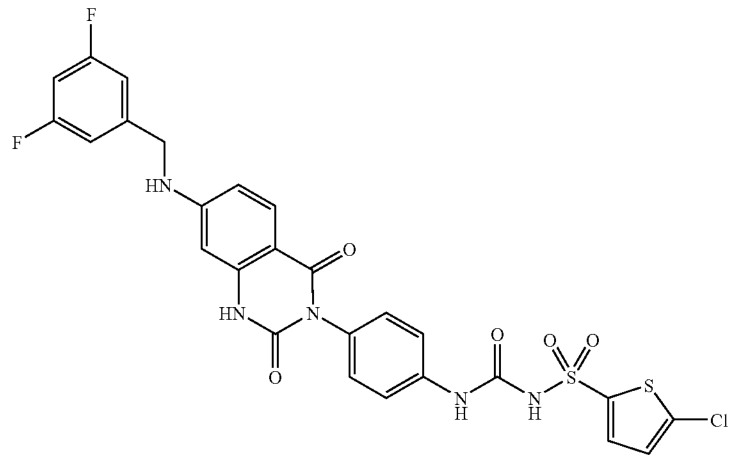 | 616 |
| 104 | 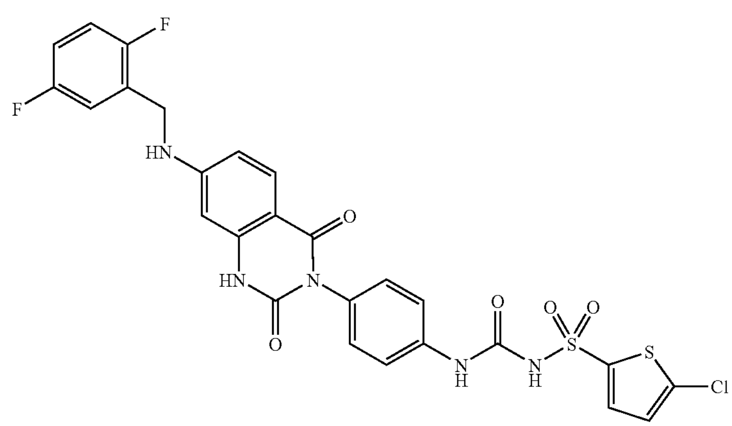 | 616 |

Example 105

4-(7-(tert-butoxycarbonyl)-2,4-dioxo-1,2-dihydro-quinazolin-3(4H)-yl)benzoic acid

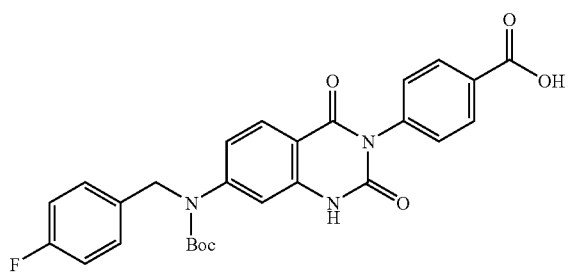

Step 1:

The aniline prepared from 4-fluorobenyl bromide using procedure described in example 1 (600 mg, 1.6 mmol) was diluted with DMF (6 mL) then treated with 4methyl 4-isocyanatobenzoate (430 mg, 2.4 mmol) and stirred at 90° C. overnight. Triethylamine (0.33 mL, 2.3 mmol) was added and the mixture heated for an additional 3 hrs at which time all material had cyclized to the desired product. The reaction was cooled, diluted with water and extracted twice with ethyl acetate and once with dichloromethane, the combined organic phases then dried over magnesium sulfate. After concentration the crude residue was purified by silica gel chromatography affording the desired producted (539 mg, 65%) contaminated with a small amount of the symmetrical urea derived from the isocyanate.

Step 2:

The mixture was then diluted with 5 mL of THF and treated with aq LiOH (1M, 2 mL, 2 mmol). Acetonitrile was added dropwise to the biphasic mixture until homogeneous. After stirring overnight the mixture was acidified with 1 M HCl to pH=3 then extrated with ethyl acetate. The organic phase was dried over magnesium sulfate, filtered, concentrated and purified by silica gel chromatography affording the carboxylic acid as an off-white solid (295 mg, 56%). ES⁻ MS showed 504 m/z, the correct mass for the product. ¹H NMR (400 MHz, DMSO-d₆) showed δ=1.44 (s, 9H), 4.89 (s, 2H), 6.97 t, 2H), 7.10 (m, 2H), 7.19 (m, 2H), 7.39 (m, 2H), 8.02 (d, 1H), 8.20 (d, 2H), 8.78 (br s, 1H), 10.58 (s, 1H).

Example 106

4-(7-(4-fluorobenzylamino)-2,4-dioxo-1,2-dihydro-quinazolin-3(4H)-yl)-N-(5-chlorothiophen-2-ylsulfonyl)benzamide

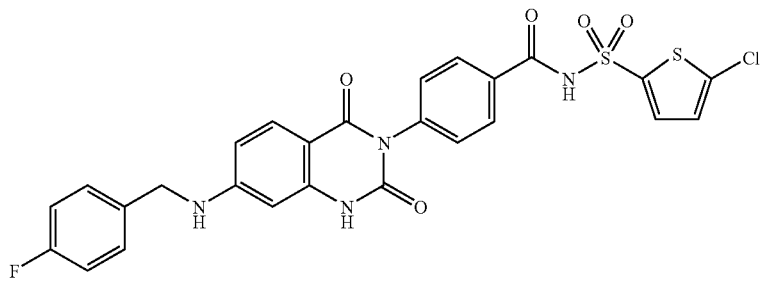

Step 1:

The carboxylic acid from example 105 (100 mg, 0.20 mmol) was dissolved in dichloromethane (3 mL), then treated with 5-chloro-2-thiophensulfonamide (27 mg, 0.22 mmol), DMAP (27 mg, 0.22 mmol) and EDC (42 mg, 0.22 mmol), then stirred at room temperature overnight. The following day the reaction was determined to be complete by analytical HPLC and the mixture diluted with water, separated, then extracted with ethyl acetate and the combined organic layers dried over magnesium sulfate.

Step 2:

After filtration the solvent was removed and the crude residue treated with HCl in dioxane (4M, 5 mL) and stirred one hour. The solvent was removed in vacuo and the residue purified by preparative HPLC affording the desired aniline as a white powder. ES⁻ MS showed 583 m/z, the correct mass for the product. $^1$H NMR (400 MHz, DMSO-$d_6$) showed δ=4.21 (s, 2H), 6.19 (s, 1H), 6.49 (d, 1H), 7.16 (t, 2H), 7.28 (d, 1H), 7.66 (m, 3H), 7.44 (s, 1H), 7.56 (d, 1H), 7.73 (d, 1H), 7.92 (d, 2H) 11.16 (s, 1H).

Example 107 methyl 4-amino-3-methoxybenzoate

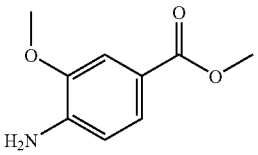

Step 1:

3-methoxy-4-nitrobenzoic acid (2.00 g, 10.2 mmol) was added to a solution of methanol (10 mL) which had been treated with thionyl chloride (1.46 mL, 20.4 mmol) at 0° C. The mixture was stirred at room temperature overnight, then concentrated, diluted with aqueous sodium bicarbonate and extracted with dichloromethane affording the desired methyl ester in quantitative yield.

Step 2:

The nitro group was then reduced by treatment with 10% Pd/C (Degussa, 200 mg) in ethyl acetate (20 mL) which was stirred under an atmosphere of hydrogen overnight. The following day the reaction mixture was filtered through celite and concentrated to give the aniline as a white solid (1.54 g, 83% for 2 steps). $^1$H NMR (400 MHz, DMSO-$d_6$) showed δ=3.73 (s, 3H), 3.78 (s, 3H), 5.59 (s, 2H), 6.60 (d, 1H), 7.28 (s, 1H), 7.35 (dd, 1H).

Example 108

4-(7-(4-fluorobenzylamino)-2,4-dioxo-1,2-dihydro-quinazolin-3(4H)-yl)-N-(5-chlorothiophen-2-ylsulfonyl)-3-methoxybenzamide

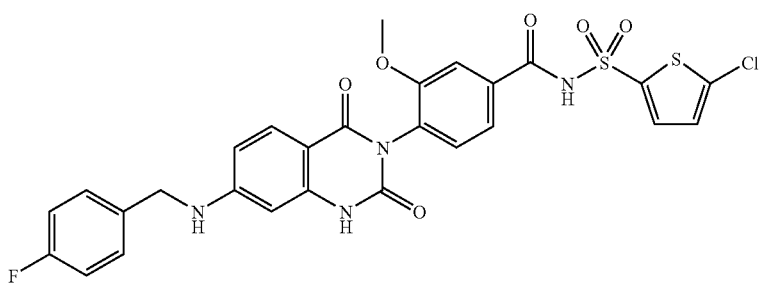

Step 1:

The aniline from example 107 (198 mg, 1.09 mmol) and TEA (0.303 mL, 2.18 mmol) in dichloromethane was added slowly to a solution of disuccinylcarbonate (280 mg, 1.09 mmol) in dichloromethane ((10 mL). The resulting solution was stirred 30 min, then treated with the aniline prepared from 4-fluorobenyl bromide using procedure described in example 1 (300 mg, 0.82 mmol) and stirred overnight at rt. The reaction mixture was concentrated, then diluted with 10 mL of DMF and stirred at 90° C. until all material had been cyclized to the desired product. At this time the reaction was worked up as described in example 33 and converted to the title compound as described in example 34. ES⁻ MS showed 613 m/z, the correct mass for the product. ¹H NMR (400 MHz, DMSO-d$_6$) showed δ=3.83 (s, 3H), 4.40 (s, 2H), 6.17 (s, 1H), 6.56 (dd, 1H), 7.06 (t, 2H), 7.13 (d, 1H), 7.32 (d, 1H), 7.36 (ddd, 2H), 7.52 (dd, 1H), 7.56 (s, 1H), 7.68 (d, 1H), 7.76 (d, 1H).

Example 109

4-(7-(4-fluorobenzylamino)-2,4-dioxo-1,2-dihydro-quinazolin-3(4H)-yl)-N-(5-chlorothiophen-2-ylsulfonyl)-3-fluorobenzamide

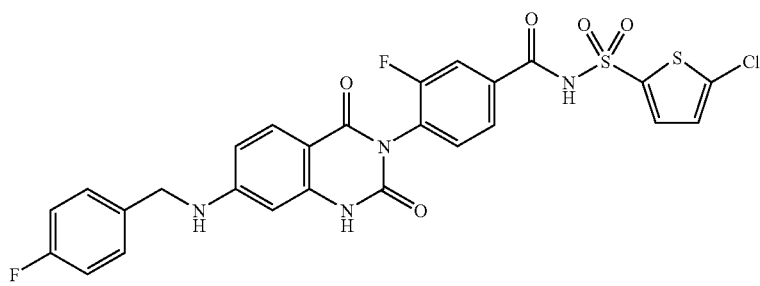

Step 1:

4-bromo-3-fluorobenzoic acid was converted to the methyl ester using the procedure described in example 107.

Step 2:

The resulting methyl 4-bromo-3-fluorobenzoate (2.00 g, 8.6 mmol) was dissolved in THF (30 mL) and treated with t-butylcarbamate (1.20 g, 10.3 mmol) and cesium carbonate (5.61 g, 17.2 mmol), then degassed with argon. The solution was then treated with 4,5-Bis(diphenylphosphino)-9,9-dimethylxanthene (0.37 g, 0.65 mmol) and Tris(dibenzylideneacetone)dipalladium (0.20 g, 0.22 mmol) and refluxed under argon overnight. The following day the reaction was cooled, diluted with water and extracted with ethyl acetate twice and the combined organic phases dried over magnesium sulfate. After filtration and concentration the crude product was purified by silica gel chromatography affording the desired product as a light yellow solid which was immediately deprotected with HCl/dioxane (4 M, 15 mL). After stirring 3 hrs the reaction was diluted with 5 mL of ether and the solid filtered affording the desired product as a light yellow solid (1.15 g, 70%). ¹H NMR (400 MHz, DMSO-d$_6$) showed δ=3.83 (s, 3H), 7.28 (t, 1H), 3.76 (m, 2H).

Step 3:

The above methyl 4-amino-3-fluorobenzoate hydrochloride (266 mg, 1.2 mmol) and triethylamine (0.80 mL, 5.6 mmol) in dichloromethane (10 mL) was added slowly to a stirring solution of phosgene (1.89 M in toluene, 1.27 mL, 2.4 mmol) in dichloromethane (10 mL). After the addition was complete the reaction mixture was stirred at rt for 1 hr, then concentrated and treated with the aniline prepared from 4-fluorobenyl bromide using procedure described in example 1 (300 mg, 0.80 mmol) in 20 mL dichloromethane and stirred overnight. The next day the reaction was concentrated, diluted with 10 mL of DMF and triethylamine (0.80 mL, 5.6 mmol) then stirred at 90° C. until all material had cyclized to the desired quinazolindione. The reaction mixture was cooled, diluted with water, then extracted twice with ethyl acetate. The combined organic phases were concentrated and purified by silica gel chromatography affording the desired quinazolinedione methyl ester contaminated with the symmetrical urea derived from the isocyanate.

This material was then converted to the title compound using the procedure described in example 34. ES⁻ MS showed 601 m/z, the correct mass for the product. ¹H NMR (400 MHz, DMSO-d$_6$) showed δ=4.33 (s, 2H), 6.19 (s, 1H), 6.51 (d, 1H), 7.15 (m, 3H), 7.34 (s, 2H), 7.50 (m, 2H), 7.61 (m, 2H), 7.81 (m, 2H), 11.29 (s, 1H).

Example 110

4-(7-(4-fluorobenzylamino)-2,4-dioxo-1,2-dihydro-quinazolin-3(4H)-yl)-N-(5-chlorothiophen-2-ylsulfonyl)-2-methylbenzamide

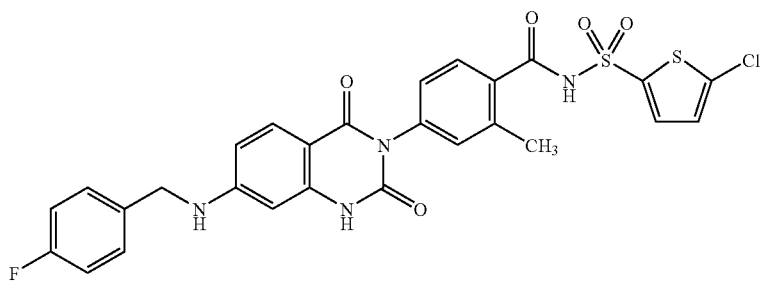

purified by silica gel chromatography affording the desired

Example 111

4-(7-(4-fluorobenzylamino)-2,4-dioxo-1,2-dihydro-quinazolin-3(4H)-yl)-N-(5-chlorothiophen-2-ylsulfonyl)-2-methoxybenzamide

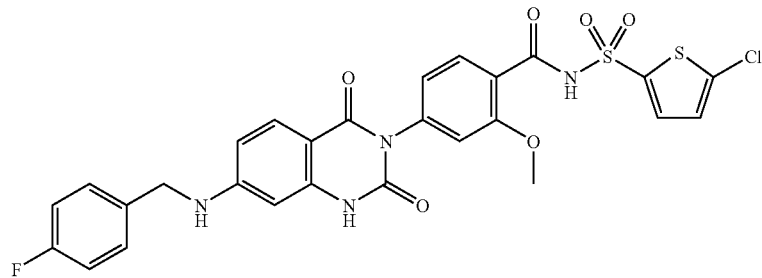

The title compound was prepared from methyl 4-amino-2-methoxybenzoate using the procedure described for example 108. ES⁻ MS showed 613 m/z, the correct mass for the product. $^1$H NMR (400 MHz, DMSO-$d_6$) showed δ=3.90 (s, 3H), 4.39 (s, 2H), 6.18 (s, 1H), 6.57 (d, 1H), 6.93 (d, 1H), 7.11 (m, 4H), 7.37 (dd, 2H), 7.70 (s, 1H), 7.73 (m, 2H).

The title compound was prepared from 4-bromo-2-methylbenzoic acid using the procedure described for example 109. ES⁻ MS showed 597 m/z, the correct mass for the product.

Example 112

4-(7-(4-fluorobenzylamino)-2,4-dioxo-1,2-dihydro-quinazoln-3(4H)-yl)-2-chloro-N-(5-chlorothiophen-2-ylsulfonyl)benzamide

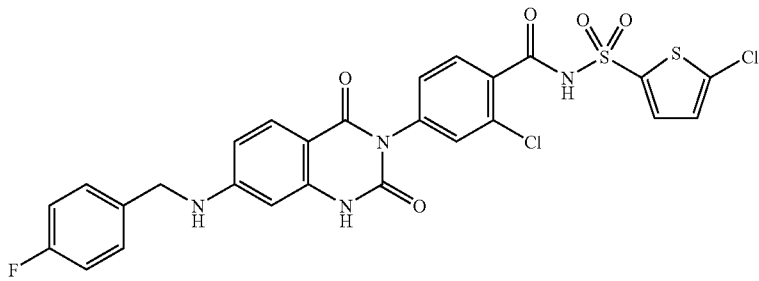

The title compound was prepared from 4-bromo-2-chlorobenzoic acid using the procedure described for example 109. ES⁻ MS showed 617 m/z, the correct mass for the product. $^1$H NMR (400 MHz, DMSO-$d_6$) showed δ=4.31 (s, 2H), 6.18 (s, 1H), 6.50 (d, 1H), 7.14 (t, 2H), 7.31 (m, 2H), 7.42 (m, 2H), 7.60 (m, 2H), 7.79 (m, 2H), 11.14 (s, 1H).

Example 113

4-(7-(4-fluorobenzylamino)-2,4-dioxo-1,2-dihydro-quinazolin-3(4H)-yl)-N-(5-chlorothiophen-2-ylsulfonyl)-2-fluorobenzamide

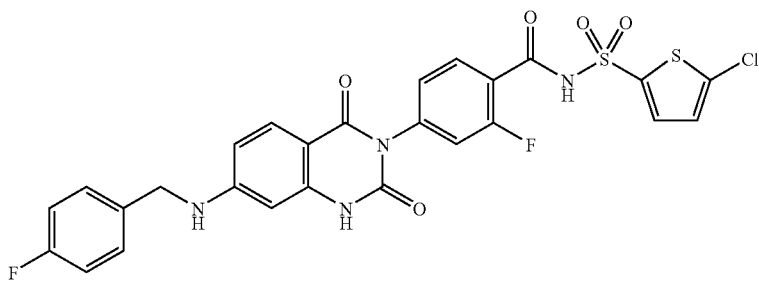

The title compound was prepared from 4-bromo-2-fluorobenzoic acid using the procedure described for example 109. ES⁻ MS showed 601 m/z, the correct mass for the product. ¹H NMR (400 MHz, DMSO-d$_6$) showed δ=4.31 (s, 2H), 6.19 (s, 1H), 6.49 (d, 1H), 7.19 (m, 3H), 7.30 (d, 1H), 7.36 (m, 2H), 7.45 (s, 1H), 7.57 (d, 1H), 7.67 (t, 1H), 7.73 (d, 1H), 11.14 (s, 1H).

Example 114

3-(7-(4-fluorobenzylamino)-2,4-dioxo-1,2-dihydroquinazolin-3(4H)-yl)-N-(5-chlorothiophen-2-ylsulfonyl)benzamide

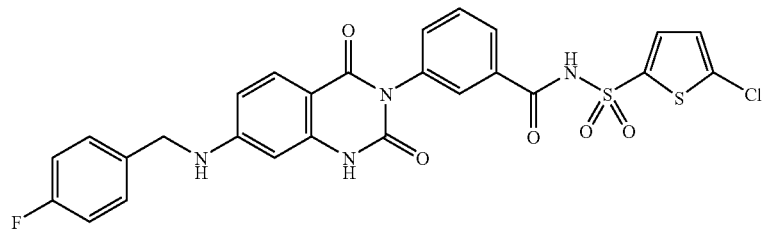

The title compound was prepared from methyl 3-aminobenzoate using the procedure described for example 108. ES⁻ MS showed 583 m/z, the correct mass for the product. ¹H NMR (400 MHz, DMSO-d$_6$) showed δ=4.30 (s, 2H), 6.19 (s, 1H), 6.49 (d, 1H), 7.14 (t, 2H), 7.24 (s, 1H), 7.38 (m, 2H), 7.43 (m, 1H), 7.53 (m, 3H), 7.70 (s, 1H), 7.79 (s, 1H), 7.90 (d, 1H), 11.18 (s, 1H).

Example 115

2-(4-(7-(4-fluorobenzylamino)-2,4-dioxo-1,2-dihydroquinazolin-3(4H)-yl)phenyl)-N-(5-chlorothiophen-2-ylsulfonyl)acetamide

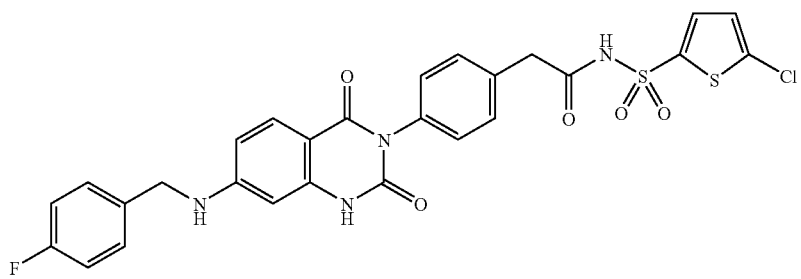

The title compound was prepared from ethyl 4-aminophenylacetate using the procedure described for example 108. ES⁻ MS showed 597 m/z, the correct mass for the product. ¹H NMR (400 MHz, DMSO-d$_6$) showed δ=3.65 (s, 2H), 4.30 (d, 2H), 6.18 (s, 1H), 6.49 (d, 1H), 7.14 (m, 3H), 7.22 (m, 3H), 7.37 (m, 2H), 7.41 (m, 1H), 7.57 (d, 1H), 7.64 (d, 1H), 11.09 (s, 1H).

Example 116

4-((7-(4-fluorobenzylamino)-2,4-dioxo-1,2-dihydroquinazolin-3(4H)-yl)methyl)-N-(5-chlorothiophen-2-ylsulfonyl)benzamide

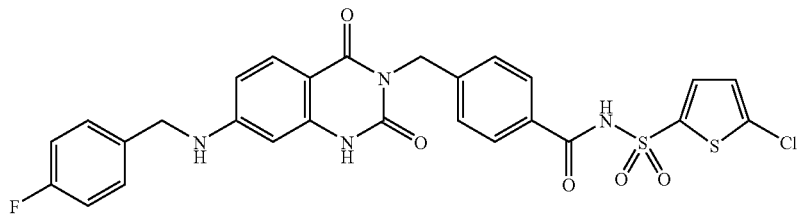

The title compound was prepared from 4-aminomethyl-benzoic acid using the procedure described for example 107 step 1, followed by the procedures for example 108. $^1$H NMR (400 MHz, DMSO-$d_6$) showed δ=4.28 (s, 2H), 5.04 (s, 2H), 6.17 (s, 1H), 6.48 (d, 1H), 7.17 (t, 2H), 7.25 (s, 1H), 7.31 (m, 4H), 7.58 (d, 1H), 7.70 (d, 1H), 7.81 (d, 2H), 11.09 (s, 1H).

Example 117

4-(7-amino-2,4-dioxo-1,2-dihydroquinazolin-3(4H)-yl)-N-(5-chlorothiophen-2-ylsulfonyl)benzamide

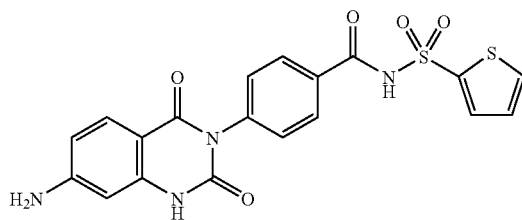

The title compound was synthesized from methyl 2-amino-4-(tert-butoxycarbonyl)benzoate using a procedure similar to example 106. $^1$H NMR (400 MHz, DMSO-$d_6$) showed δ=6.21 (s, 1H), 6.40 (d, 1H), 7.25 (d, 1H), 7.38 (d, 2H), 7.54 (d, 1H), 7.71 (s, 1H), 7.93 (d, 2H), 11.18 (s, 1H).

Example 118

4-(7-(benzylamino)-2,4-dioxo-1,2-dihydroquinazoln-3(4H)-yl)-N-(5-chlorothiophen-2-ylsulfonyl)benzamide

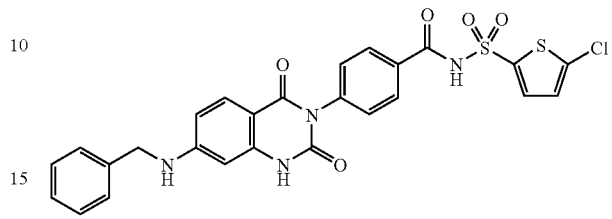

The aniline from example 117 (20 mg, 0.042 mmol) and benzaldehyde (7 μL, 0.063 mmol) were dissolved in 10% acetic acid/methanol (2 mL) and stirred for 30 min. Then, sodium cyanoborohydride (6 mg, 0.84 mmol) was added and the reaction stirred at rt overnight. The next day the reaction mixture was concentrated and purified by preparative HPLC affording the desired product as a white solid after lyophilization. $^1$H NMR (400 MHz, DMSO-$d_6$) showed δ=4.32 (s, 2H), 6.20 (s, 1H), 6.49 (d, 1H), 7.26 (s, 2H), 7.33 (m, 5H), 7.45 (s, 1H), 7.57 (d, 1H), 7.70 (s, 1H), 7.92 (d, 2H), 11.16 (s, 1H).

Similarly, following the procedure described in Example 118, but replacing benzaldehyde with other suitable aldehydes and ketones, and utilizing the modifications known to those skilled in the art, Examples 119–140 were synthesized:

TABLE 3

| Example | Structure | ES-MS |
| --- | --- | --- |
| 119 | 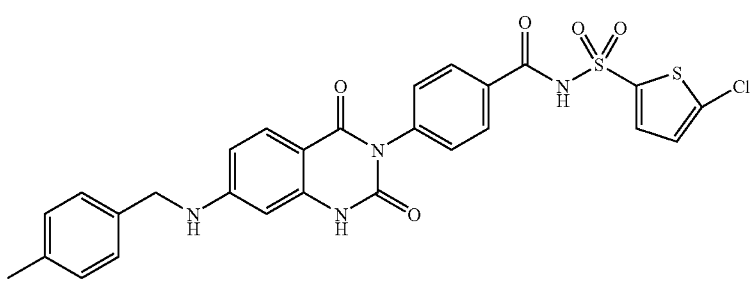 | (M − H)$^-$ = 579 |
| 120 | 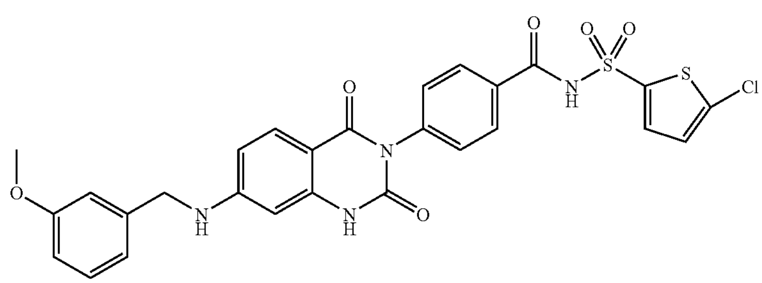 | (M − H)$^-$ = 595 |

TABLE 3-continued
| Example | Structure | ES-MS |
|---|---|---|
| 121 | 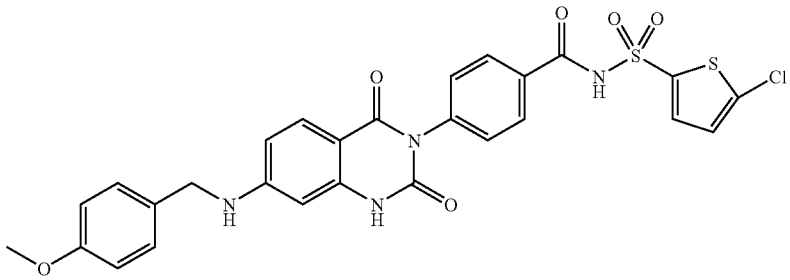 | (M − H)⁻ = 595 |
| 122 | 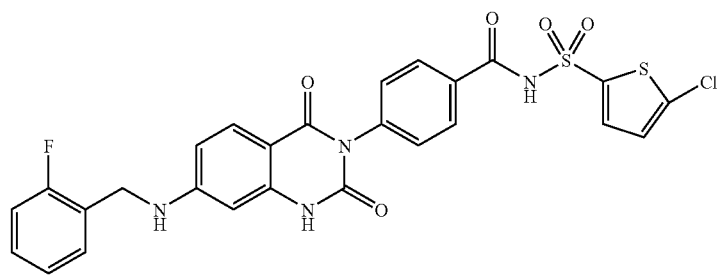 | (M − H)⁻ = 583 |
| 123 | 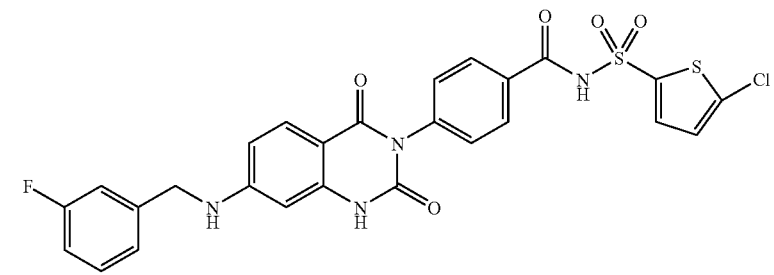 | (M − H)⁻ = 583 |
| 124 | 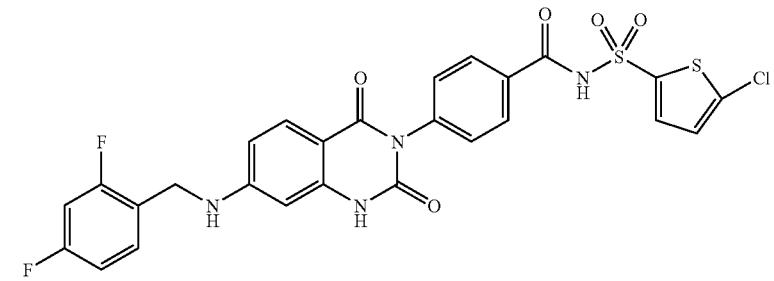 | (M − H)⁻ = 601 |
| 125 | 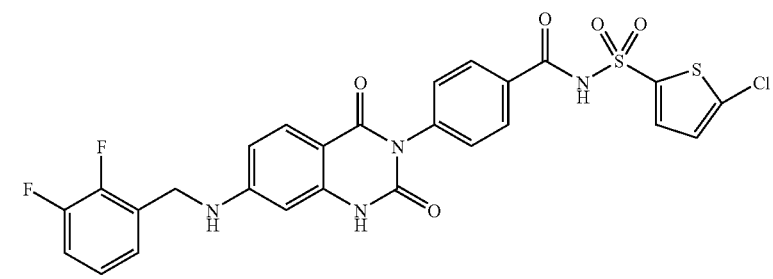 | (M − H)⁻ = 601 |

TABLE 3-continued

| Example | Structure | ES-MS |
|---------|-----------|-------|
| 126 | 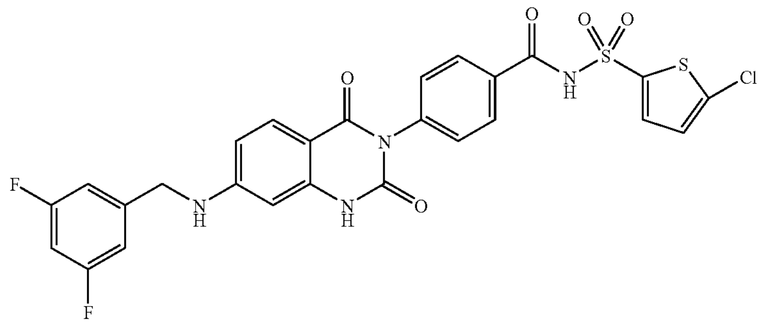 | (M − H)⁻ = 601 |
| 127 | 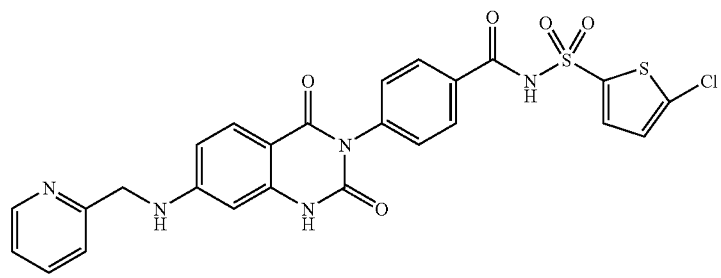 | (M − H)⁻ = 566 |
| 128 | 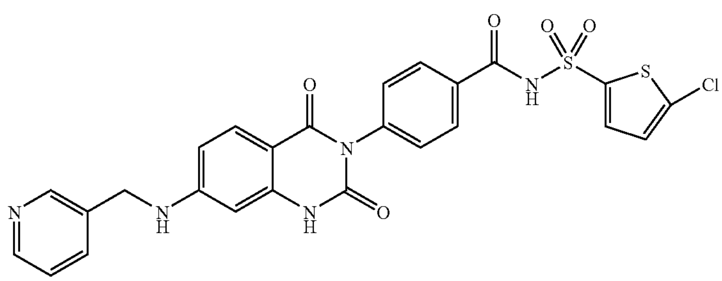 | (M − H)⁻ = 566 |
| 129 | 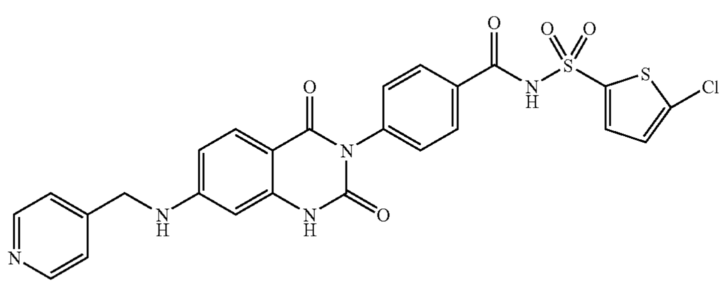 | (M − H)⁻ = 566 |
| 130 | 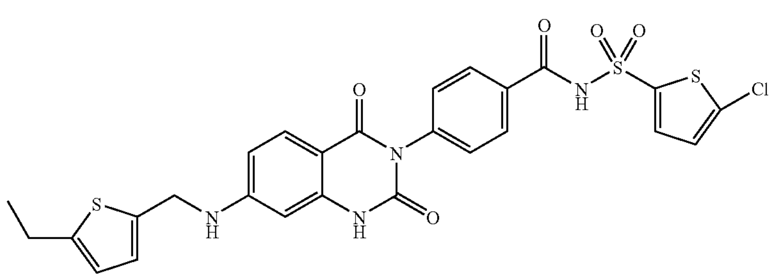 | (M − H)⁻ = 599 |

TABLE 3-continued

| Example | Structure | ES-MS |
|---|---|---|
| 131 | 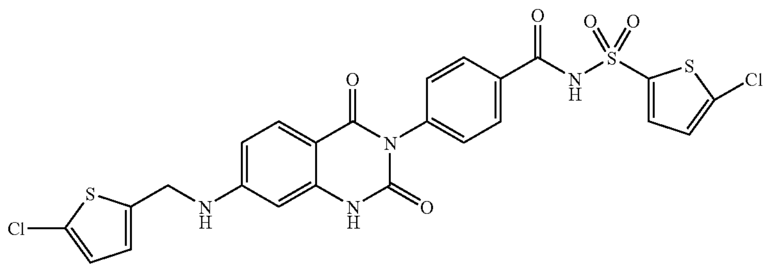 | (M − H)⁻ = 605 |
| 132 | 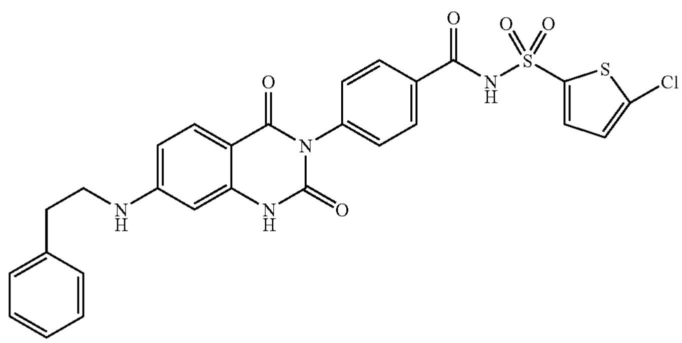 | (M − H)⁻ = 579 |
| 133 | 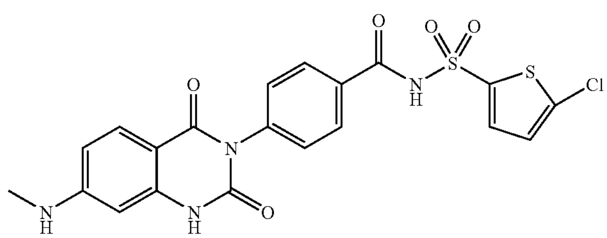 | (M + H)⁺ = 491 |
| 134 | 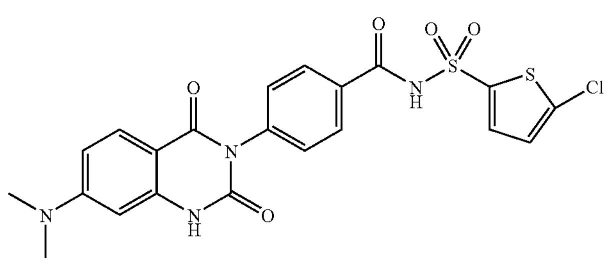 | (M + H)⁺ = 505 |
| 135 | 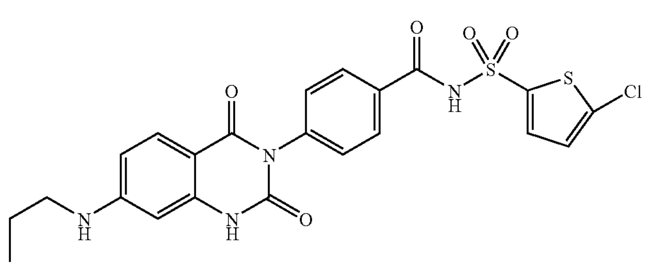 | (M − H)⁻ = 517 |

TABLE 3-continued

| Example | Structure | ES-MS |
|---|---|---|
| 136 | 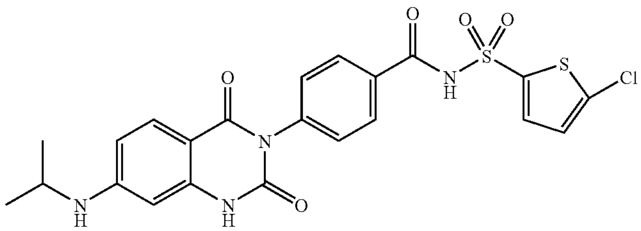 | (M − H)⁻ = 517 |
| 137 | 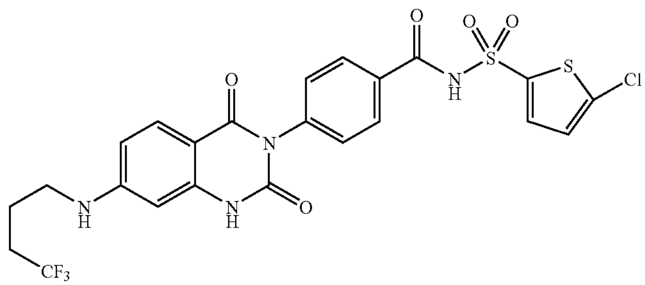 | (M − H)⁻ = 585 |
| 138 | 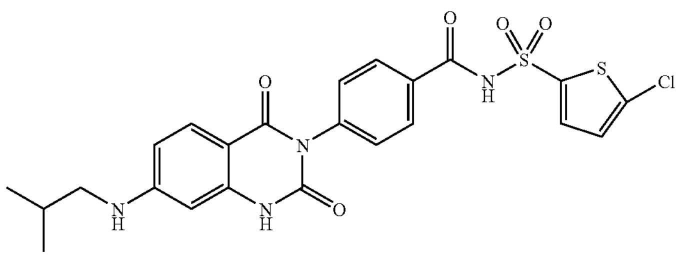 | (M − H)⁻ = 531 |
| 139 | 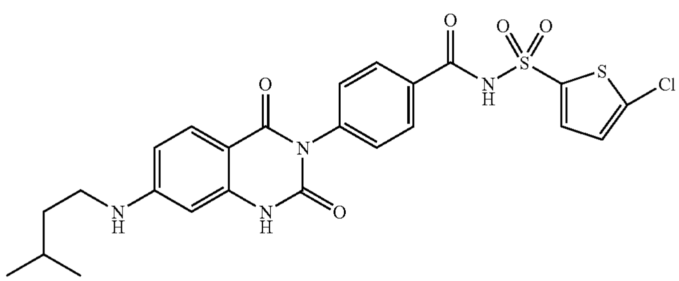 | (M − H)⁻ = 545 |
| 140 | 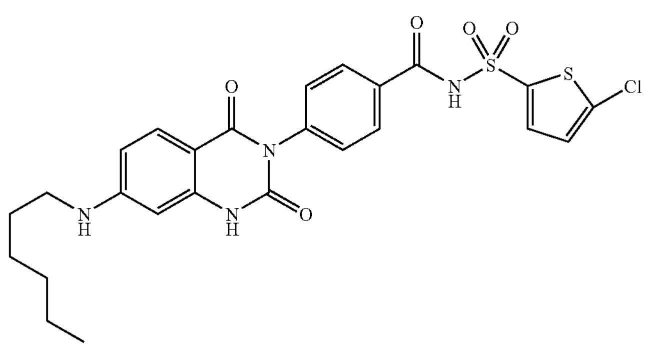 | (M − H)⁻ = 559 |

Example 141

Pharmacological Assays

The pharmacological activity of each of the compounds according to the invention is determined by the following in vitro assays:

I. Inhibition of ADP-Mediated Platelet Aggregation In Vitro

The effect of testing the compound according to the invention on ADP-induced human platelet aggregation is preferably assessed in 96-well microtiter assay (see generally the procedures in Jantzen, H. M. et al. (1999) Thromb. Hemost. 81:111–117). Human venous blood is collected from healthy, drug-free volunteers into ACD (85 mM sodium citrate, 111 mM glucose, 71.4 mM citric acid) containing $PGI_2$ (1.25 ml ACD containing 1.6 µM $PGI_2$/10 ml blood; $PGI_2$ was from Sigma, St. Louis, Mo.). Platelet-rich plasma (PRP) is prepared by centrifugation at 160×g for 20 minutes at room temperature. Washed platelets are prepared by centrifuging PRP for 10 minutes at 730×g and resuspending the platelet pellet in CGS (13 mM sodium citrate, 30 mM glucose, 120 mM NaCl; 2 ml CGS/10 ml original blood volume) containing 1U/ml apyrase (grade V, Sigma, St. Louis, Mo.). After incubation at 37° C. for 15 minutes, the platelets are collected by centrifugation at 730×g for 10 minutes and resuspended at a concentration of $3\times10^8$ platelets/ml in Hepes-Tyrode's buffer (10 mM Hepes, 138 mM NaCl, 5.5 mM glucose, 2.9 mM KCl, 12 mM $NaHCO_3$, pH 7.4) containing 0.1% bovine serum albumin, 1 mM $CaCl_2$ and 1 mM $MgCl_2$. This platelet suspension is kept >45 minutes at 37° C. before use in aggregation assays.

Inhibition of ADP-dependent aggregation is preferably determined in 96-well flat-bottom microtiter plates using a microtiter plate shaker and plate reader similar to the procedure described by Frantantoni et al., Am. J. Clin. Pathol. 94, 613 (1990). All steps are performed at room temperature. The total reaction volume of 0.2 ml/well includes in Hepes-Tyrodes buffer/0.1% BSA: $4.5\times10^7$ apyrase-washed platelets, 0.5 mg/ml human fibrinogen (American Diagnostica, Inc., Greenwich, Conn.), serial dilutions of test compounds (buffer for control wells) in 0.6% DMSO. After about 5 minutes preincubation at room temperature, ADP is added to a final concentration of 2 µM which induces submaximal aggregation. Buffer is added instead of ADP to one set of control wells ($ADP^-$ control). The OD of the samples is then determined at 490 nm using a microtiter plate reader (Softmax, Molecular Devices, Menlo Park, Calif.) resulting in the 0 minute reading. The plates are then agitated for 5 min on a microtiter plate shaker and the 5 minute reading is obtained in the plate reader. Aggregation is calculated from the decrease of OD at 490 nm at t=5 minutes compared to t=0 minutes and is expressed as % of the decrease in the ADP control samples after correcting for changes in the unaggregated control samples.

II. Inhibition of [$^3$H]2-MeS-ADP Binding to Platelets

Having first determined that the compounds according to the invention inhibit ADP-dependent platelet aggregation with the above assay, a second assay is used to determine whether such inhibition is mediated by interaction with platelet ADP receptors. Utilizing the second assay the potency of inhibition of such compounds with respect to [$^3$H]2-MeS-ADP binding to whole platelets is determined. [$^3$H]2-MeS-ADP binding experiments are routinely performed with outdated human platelets collected by standard procedures at hospital blood banks. Apyrase-washed outdated platelets are prepared as follows (all steps at room temperature, if not indicated otherwise):

Outdated platelet suspensions are diluted with 1 volume of CGS and platelets pelleted by centrifugation at 1900×g for 45 minutes. Platelet pellets are resuspended at $3-6\times10^9$ platelets/ml in CGS containing 1 U/ml apyrase (grade V, Sigma, St. Louis, Mo.) and incubated for 15 minutes at 37° C. After centrifugation at 730×g for 20 minutes, pellets are resuspended in Hepes-Tyrode's buffer containing 0.1% BSA (Sigma, St. Louis, Mo.) at a concentration of $6.66\times10^8$ platelets/ml. Binding experiments are performed after >45 minutes resting of the platelets.

Alternatively, binding experiments are performed with fresh human platelets prepared as described in I. (Inhibition of ADP-Mediated Platelet Aggregation in vitro), except that platelets are resuspended in Hepes-Tyrode's buffer containing 0.1% BSA (Sigma, St. Louis, Mo.) at a concentration of $6.66\times10^8$ platelets/ml. Very similar results are obtained with fresh and outdated platelets.

A platelet ADP receptor binding assay using the tritiated potent agonist ligand [$^3$H]2-MeS-ADP (Jantzen, H. M. et al. (1999) Thromb. Hemost. 81:111–117) has been adapted to the 96-well microtiter format. In an assay volume of 0.2 ml Hepes-Tyrode's buffer with 0.1% BSA and 0.6% DMSO, $1\times10^8$ apyrase-washed platelets are preincubated in 96-well flat bottom microtiter plates for 5 minutes with serial dilutions of test compounds before addition of 1 nM [$^3$H]2-MeS-ADP ([$^3$H]2-methylthioadenosine-5'-diphosphate, ammonium salt; specific activity 48–49 Ci/mmole, obtained by custom synthesis from Amersham Life Science, Inc., Arlington Heights, Ill., or NEN Life Science Products, Boston, Mass.). Total binding is determined in the absence of test compounds. Samples for nonspecific binding may contain $10^{-5}$ M unlabelled 2-MeS-ADP (RBI, Natick, Mass.). After incubation for 15 minutes at room temperature, unbound radioligand is separated by rapid filtration and two washes with cold (4–8° C.) Binding Wash Buffer (10 mM Hepes pH 7.4, 138 mM NaCl) using a 96-well cell harvester (Minidisc 96, Skatron Instruments, Sterling, Va.) and 8×12 GF/C glassfiber filtermats (Printed Filtermat A, for 1450 Microbeta, Wallac Inc., Gaithersburg, Md.). The platelet-bound radioactivity on the filtermats is determined in a scintillation counter (Microbeta 1450, Wallac Inc., Gaithersburg, Md.). Specific binding is determined by subtraction of non-specific binding from total binding, and specific binding in the presence of test compounds is expressed as % of specific binding in the absence of test compounds dilutions.

The table below provides activity for selected compounds of the invention, evaluated as described above. In the table below, activity in the PRP assay is provided as follows: +++, $IC_{50}<10$ µM; ++, 10 µM<$IC_{50}$<30 µM; and +, $IC_{50}>30$ µM.

| Example No. | Activity |
| --- | --- |
| Example 3 | +++ |
| Example 5 | +++ |
| Example 12 | +++ |
| Example 16 | +++ |
| Example 21 | +++ |
| Example 41 | ++ |
| Example 51 | +++ |
| Example 53 | ++ |
| Example 57 | +++ |
| Example 61 | ++ |
| Example 65 | + |
| Example 72 | ++ |
| Example 77 | + |
| Example 94 | + |

-continued

| Example No. | Activity |
|---|---|
| Example 100 | +++ |
| Example 102 | + |
| Example 106 | +++ |
| Example 113 | +++ |

It should be understood that the foregoing discussion, embodiments and examples merely present a detailed description of certain preferred embodiments. It will be apparent to those of ordinary skill in the art that various modifications and equivalents can be made without departing from the spirit and scope of the invention. All the patents, journal articles and other documents discussed or cited above are herein incorporated by reference.

What is claimed is:

1. A compound having the formula:

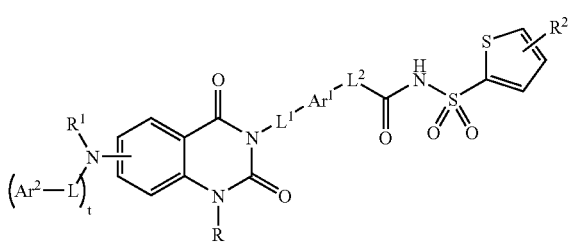

wherein

R is a member selected from the group consisting of H and $C_{1-6}$ alkyl;

$R^1$ is a member selected from the group consisting of H, $C_{1-6}$ alkyl, $C_{1-6}$ haloalkyl, $C_{3-5}$ cycloalkyl and $C_{3-5}$ cycloalkyl-alkyl;

$R^2$ is a member selected from the group consisting of H, halogen, $C_{1-6}$ alkyl, $C_{2-6}$ alkenyl, $C_{2-6}$ alkynyl, $C_{1-6}$ haloalkyl, $C_{1-6}$ alkoxy, cyano and —C(O)$R^{2a}$, wherein $R^{2a}$ is a member selected from the group consisting of $C_{1-6}$ alkoxy and ($C_{1-6}$ alkyl)$_{0-2}$ amino;

L is a 1 to 3 carbon linking group selected from the group consisting of —CH$_2$—, —CH(CH$_3$)—, —CH$_2$CH$_2$—, —CH$_2$CH(CH$_3$)— and —CH$_2$CH$_2$CH$_2$—;

$L^1$ is a linking group selected from the group consisting of a bond and —CH$_2$—;

$L^2$ is a linking group selected from the group consisting of a bond, —NH— and —CH$_2$—;

Ar$^1$ is an aromatic ring selected from the group consisting of benzene, pyridine and pyrimidine, each of which is optionally substituted with from 1–2 $R^3$ substituents,
wherein each $R^3$ is independently selected from the group consisting of halogen, cyano, hydroxy, $C_{1-6}$ alkyl, $C_{2-6}$ alkenyl, $C_{2-6}$ alkynyl, $C_{1-6}$ alkoxy, $C_{1-6}$ haloalkyl, $C_{1-6}$ haloalkoxy, $C_{3-5}$ cycloalkyl, $C_{3-5}$ cycloalkyl-alkyl, $C_{3-5}$ cycloalkyl-alkoxy, ($C_{1-6}$ alkyl)$_{0-2}$ amino, —C(O)$R^{3a}$, —O(CH$_2$)$_m$OR$^{3b}$, —(CH$_2$)$_m$OR$^{3b}$, —O(CH$_2$)$_m$N(R$^{3b}$)$_2$ and —(CH$_2$)$_m$N(R$^{3b}$)$_2$,
wherein the subscript m is an integer of from 1 to 3, each $R^{3a}$ is a member independently selected from the group consisting of H, hydroxy, $C_{1-6}$ alkyl, $C_{1-6}$ alkoxy, ($C_{1-6}$ alkyl)$_{0-2}$ amino, and each $R^{3b}$ is a member independently selected from the group consisting of H, $C_{1-4}$ alkyl and $C_{1-4}$ alkanoyl, and optionally, two $R^{3b}$ groups attached to nitrogen are combined with the nitrogen atom to form an azetidine, pyrrolidine or piperidine ring;

AR$^2$ is a 5–6 membered monocyclic or 9–10 membered fused-bicyclic aromatic ring system, optionally having from 1 to 3 heteroatoms selected from N, O and S as ring vertices, said ring system being optionally substituted with from 1 to 3 $R^4$ substituents
wherein each of said $R^4$ substituents is independently selected from the group consisting of halogen, cyano, hydroxy, $C_{1-6}$ alkyl, $C_{2-6}$ alkenyl, $C_{2-6}$ alkynyl, $C_{1-6}$ alkoxy, $C_{1-6}$ haloalkyl, $C_{1-6}$ haloalkoxy, $C_{3-5}$ cycloalkyl, $C_{3-5}$ cycloalkyl-alkyl, $C_{3-5}$ cycloalkyl-alkoxy, ($C_{1-6}$ alkyl)$_{0-2}$ amino and —C(O)$R^{4a}$,
wherein each $R^{4a}$ is a member independently selected from the group consisting of H, hydroxy, $C_{1-6}$ alkyl, $C_{1-6}$ alkoxy and ($C_{1-6}$ alkyl)$_{0-2}$ amino;

the subscript t is 0 or 1 when $L^2$ is a bond, and is 1 when $L^2$ is selected from —NH— and —CH$_2$— and when t is 0, then the moiety (AR2-L)$_0$ is H;

or a pharmaceutically acceptable salt thereof.

2. A compound of claim 1, wherein $R^1$ is H or $C_{1-4}$ alkyl; L is selected from the group consisting of —CH$_2$—, —CH(CH$_3$)— and —CH$_2$CH$_2$—; $L^1$ is a bond and $R^2$ is selected from the group consisting of halogen, $C_{1-4}$ alkyl, $C_{1-4}$ alkoxy, $C_{1-4}$ haloalkyl, —CN, —C≡CH and —CONH$_2$.

3. A compound of claim 1, wherein AR$^1$ is a benzene ring, optionally substituted with 1–2 $R^3$ substituents.

4. A compound of claim 1, wherein Ar$^1$ is a pyridine ring, optionally substituted with 1–2 $R^3$ substituents.

5. A compound of claim 1, wherein Ar$^1$ is a pyrimidine ring, optionally substituted with 1–2 $R^3$ substituents.

6. A compound of claim 3, wherein AR$^2$ is benzene or naphthalene, each of which is optionally substituted with from 1 to 3 $R^4$ substituents.

7. A compound of claim 3, wherein AR$^2$ is selected from the group consisting of furan, thiophene, thiazole, oxazole, thiadiazole, imidazole, pyrazole, pyridine, pyrimidine, benzothiophene, indole, quinoline, isoquinoline, benzofuran, benzimidazole, benzoxazole and benzothiazole, each of which is optionally substituted with from 1 to 3 $R^4$ substituents.

8. A compound of claim 7, wherein $R^1$ is H or $C_{1-4}$ alkyl; L is selected from the group consisting of —CH$_2$—, —CH(CH$_3$)— and —CH$_2$CH$_2$—; $L^1$ is a bond and $R^2$ is selected from the group consisting of halogen, $C_{1-4}$ alkyl, $C_{1-4}$ alkoxy, $C_{1-4}$ haloalkyl, —CN, —C≡CH and —CONH$_2$.

9. A compound of claim 6, wherein $R^1$ is H or $C_{1-4}$ alkyl; L is selected from the group consisting of —CH$_2$—, —CH(CH$_3$)— and —CH$_2$CH$_2$—; $L^1$ is a bond and $R^2$ is selected from the group consisting of halogen, $C_{1-4}$ alkyl, $C_{1-4}$ alkoxy, $C_{1-4}$ haloalkyl, —CN, —C≡CH and —CONH$_2$.

10. A compound of claim 1, having the formula:

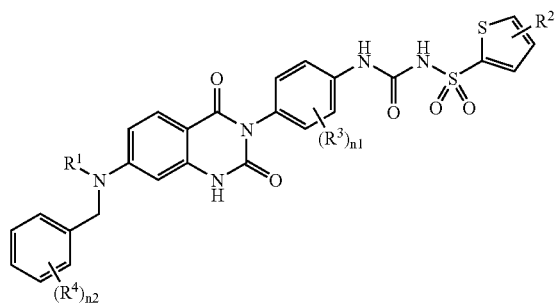

wherein the subscripts n1 and n2 each independently represent an integer of from 0 to 2.

11. A compound of claim 10, wherein $R^1$ is H; $R^2$ is selected from the group consisting of halogen, $C_{1-4}$ alkyl, $C_{1-4}$ alkoxy, $C_{1-4}$ haloalkyl, —CN, —C≡CH and —CONH$_2$; each $R^3$, when present is independently selected from the group consisting of $C_{1-4}$ alkyl, $C_{1-4}$ alkoxy, $C_{3-5}$ cycloalkyl-alkoxy, —O(CH$_2$)$_m$OR$^{3b}$ and —O(CH$_2$)$_m$N(R$^{3b}$)$_2$ wherein the subscript m is 1 or 2 and each $R^{3b}$ is independently selected from the group consisting of H, $C_{1-4}$ alkyl and $C_{1-4}$ alkanoyl; and each $R^4$, when present is independently selected from the group consisting of halogen, cyano, hydroxy, $C_{16}$ alkyl, $C_{2-6}$ alkenyl, $C_{2-6}$ alkynyl, $C_{1-6}$ alkoxy, $C_{1-6}$ haloalkyl, $C_{3-5}$ cycloalkyl, $C_{3-5}$ cycloalkyl-alkyl, $C_{3-5}$ cycloalkyl-alkoxy and (C$_{1-6}$ alkyl)$_{0-2}$ amino.

12. A compound of claim 11, wherein $R^2$ is halogen and is attached to the 5-position of the thienyl ring; and each $R^4$ when present is independently selected from the group consisting of halogen, cyano and $C_{1-6}$ alkyl.

13. A compound of claim 1, selected from the group consisting of:

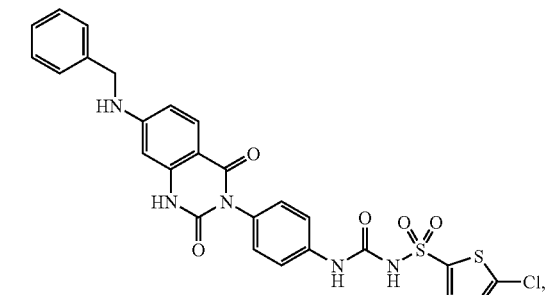

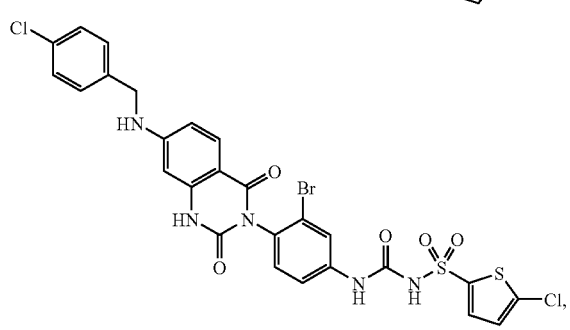

-continued

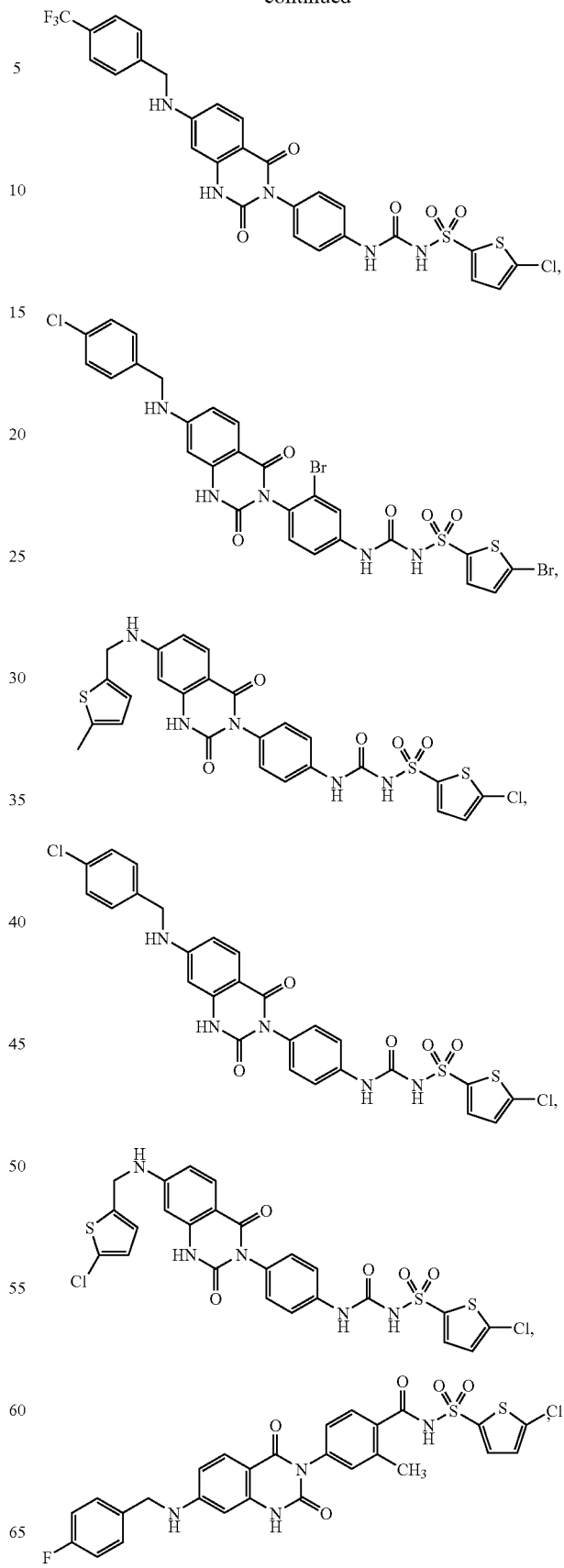

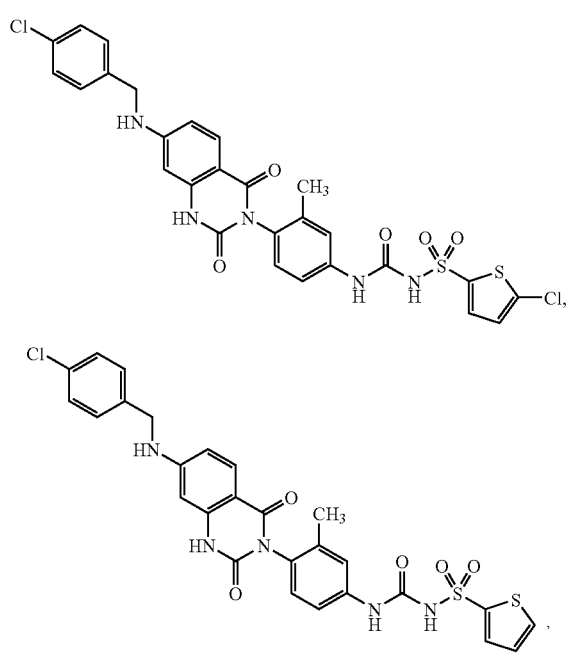
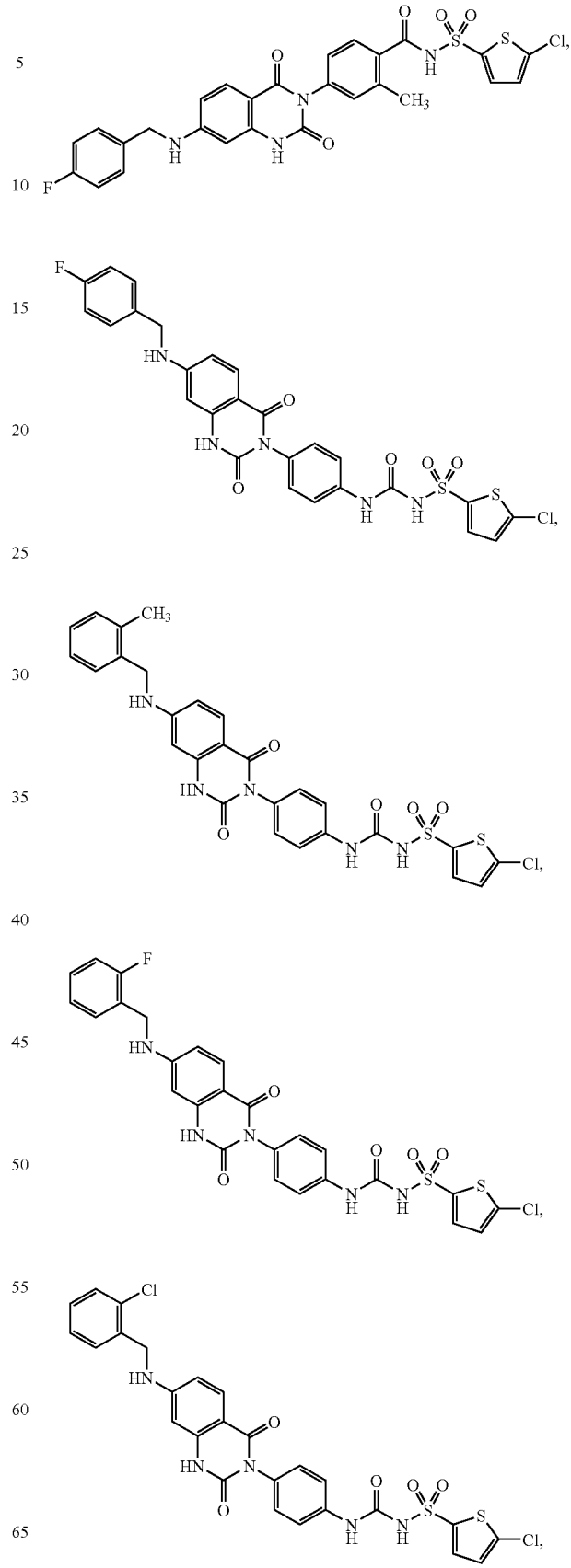

-continued

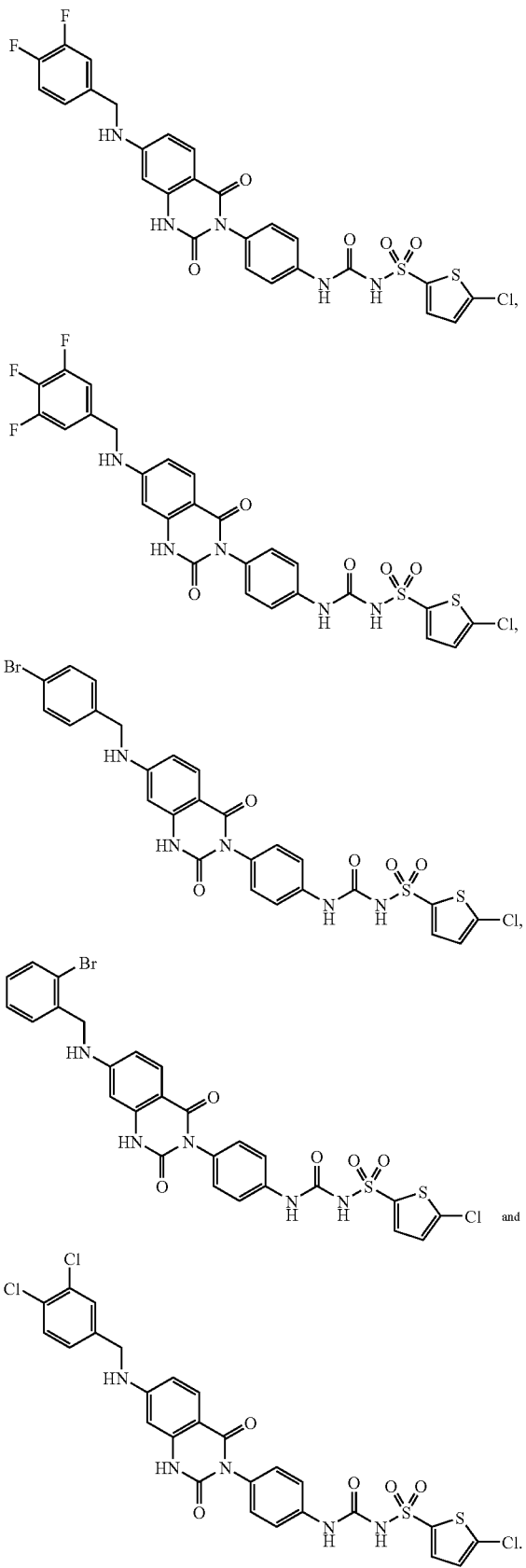

14. A compound of claim 3, wherein $AR^2$ is selected from the group consisting of furan, thiophene, thiazole, oxazole, thiadiazole, imidazole, pyrazole, pyridine and pyrimidine, each of which is optionally substituted with from 1 to 2 $R^4$ substituents.

15. A compound of claim 14, wherein $R^1$ is H or $C_{1-4}$ alkyl; L is selected from the group consisting of —$CH_2$—, —$CH(CH_3)$— and —$CH_2CH_2$—; and $R^2$ is selected from the group consisting of halogen, $C_{1-4}$ alkyl, $C_{1-4}$ alkoxy, $C_{1-4}$ haloalkyl, —CN, —C≡CH and —$CONH_2$.

16. A compound of claim 3, wherein $AR^2$ is selected from the group consisting of benzothiophene, indole, quinoline, isoquinoline, benzofuran, benzimidazole, benzoxazole and benzothiazole, each of which is optionally substituted with from 1 to 2 $R^4$ substituents.

17. A compound of claim 16, wherein $R^1$ is H or $C_{1-4}$ alkyl; L is selected from the group consisting of —$CH_2$—, —$CH(CH_3)$— and —$CH_2CH_2$—; and $R^2$ is selected from the group consisting of halogen, $C_{1-4}$ alkyl, $C_{1-4}$ alkoxy, $C_{1-4}$ haloalkyl, —CN, —C≡CH and —$CONH_2$.

18. A compound of claim 1, having the formula:

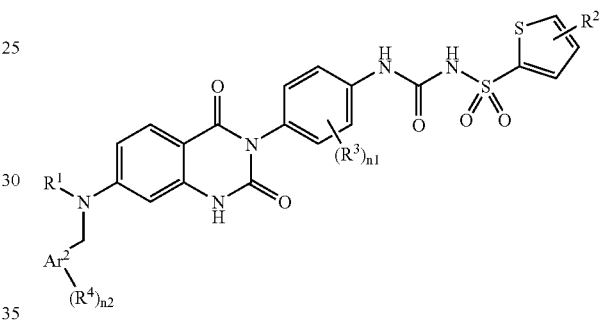

wherein the subscripts n1 and n2 each independently represent an integer of from 0 to 2.

19. A compound of claim 18, wherein $AR^2$ is selected from the group consisting of furan, thiophene, thiazole, oxazole, thiadiazole, imidazole, pyrazole, pyridine and pyrimidine, each of which is optionally substituted with from 1 to 2 $R^4$ substituents.

20. A compound of claim 19, wherein $R^1$ is H; $R^2$ is selected from the group consisting of halogen, $C_{1-4}$ alkyl, $C_{1-4}$ alkoxy, $C_{1-4}$ haloalkyl, —CN, —C≡CH and —$CONH_2$; each $R^3$, when present is independently selected from the group consisting of $C_{1-4}$ alkyl, $C_{1-4}$ alkoxy, $C_{3-5}$ cycloalkyl-alkoxy, —$O(CH_2)_mOR^{3b}$ and —$O(CH_2)_mN(R^{3b})_2$ wherein the subscript m is 1 or 2 and each $R^{3b}$ is independently selected from the group consisting of H, $C_{1-4}$ alkyl and $C_{1-4}$ alkanoyl; and each $R^4$, when present is independently selected from the group consisting of halogen, cyano, hydroxy, $C_{1-6}$ alkyl, $C_{2-6}$ alkenyl, $C_{2-6}$ alkynyl, $C_{1-6}$ alkoxy, $C_{1-6}$ haloalkyl, $C_{3-5}$ cycloalkyl, $C_{3-5}$ cycloalkyl-alkyl, $C_{3-5}$ cycloalkyl-alkoxy and $(C_{1-6}$ alkyl$)_{0-2}$ amino.

21. A compound of claim 20, wherein $R^2$ is halogen and is attached to the 5-position of the thienyl ring; and each $R^4$ when present is independently selected from the group consisting of halogen, cyano and $C_{1-6}$ alkyl.

22. A compound of claim 18, wherein $AR^2$ is selected from the group consisting of benzothiophene, indole, quinoline, isoquinoline, benzofuran, benzimidazole, benzoxazole and benzothiazole, each of which is optionally substituted with from 1 to 2 $R^4$ substituents.

23. A compound of claim 22, wherein $R^1$ is H; $R^2$ is selected from the group consisting of halogen, $C_{1-4}$ alkyl, $C_{1-4}$ alkoxy, $C_{1-4}$ haloalkyl, —CN, —C≡CH and —CONH$_2$; each R$^3$, when present is independently selected from the group consisting of $C_{1-4}$ alkyl, $C_{1-4}$ alkoxy, $C_{3-5}$ cycloalkyl-alkoxy, —O(CH$_2$)$_m$OR$^{3b}$ and —O(CH$_2$)$_m$N(R$^{3b}$)$_2$ wherein the subscript m is 1 or 2 and each R$^{3b}$ is independently selected from the group consisting of H, $C_{1-4}$ alkyl and $C_{1-4}$ alkanoyl; and each R$^4$, when present is independently selected from the group consisting of halogen, cyano, hydroxy, $C_{1-6}$ alkyl, $C_{2-6}$ alkenyl, $C_{2-6}$ alkynyl, $C_{1-6}$ alkoxy, $C_{1-6}$ haloalkyl, $C_{3-5}$ cycloalkyl, $C_{3-5}$ cycloalkyl-alkyl, $C_{3-5}$ cycloalkyl-alkoxy and ($C_{1-6}$ alkyl)$_{0-2}$ amino.

24. A compound of claim 23, wherein R$^2$ is halogen and is attached to the 5-position of the thienyl ring; and R$^4$ when present is selected from the group consisting of halogen, cyano and $C_{1-6}$ alkyl.

25. A compound of claim 1, having the formula:

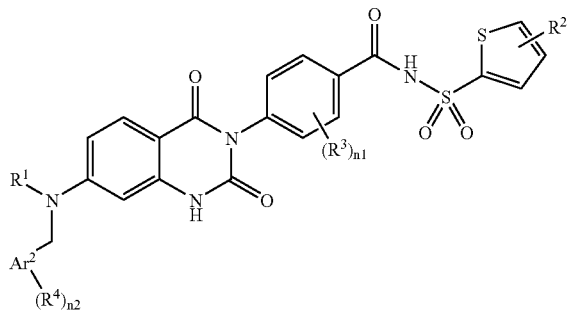

wherein the subscripts n1 and n2 each independently represent an integer of from 0 to 2.

26. A compound of claim 25, wherein AR$^2$ is selected from the group consisting of furan, thiophene, thiazole, oxazole, thiadiazole, imidazole, pyrazole, pyridine and pyrimidine, each of which is optionally substituted with from 1 to 2 R$^4$ substituents.

27. A compound of claim 26, wherein R$^1$ is H; R$^2$ is selected from the group consisting of halogen, $C_{1-4}$ alkyl, $C_{1-4}$ alkoxy, $C_{1-4}$ haloalkyl, —CN, —C≡CH and —CONH$_2$; each R$^3$, when present is independently selected from the group consisting of $C_{1-4}$ alkyl, $C_{1-4}$ alkoxy, $C_{3-5}$ cycloalkyl-alkoxy, —O(CH$_2$)$_m$OR$^{3b}$ and —O(CH$_2$)$_m$N(R$^{3b}$)$_2$ wherein the subscript m is 1 or 2 and each R$^{3b}$ is independently selected from the group consisting of H, $C_{1-4}$ alkyl and $C_{1-4}$ alkanoyl; and each R$^4$, when present is independently selected from the group consisting of halogen, cyano, hydroxy, $C_{1-6}$ alkyl, $C_{2-6}$ alkenyl, $C_{2-6}$ alkynyl, $C_{1-6}$ alkoxy, $C_{1-6}$ haloalkyl, $C_{3-5}$ cycloalkyl, $C_{3-5}$ cycloalkyl-alkyl, $C_{3-5}$ cycloalkyl-alkoxy and ($C_{1-6}$ alkyl)$_{0-2}$ amino.

28. A compound of claim 27, wherein R$^2$ is halogen and is attached to the 5-position of the thienyl ring; and each R$^4$ when present is independently selected from the group consisting of halogen, cyano and $C_{1-6}$ alkyl.

29. A compound of claim 25, wherein Ar$^2$ is selected from the group consisting of benzothiophene, indole, quinoline, isoquinoline, benzofuran, benzimidazole, benzoxazole and benzothiazole, each of which is optionally substituted with from 1 to 2 R$^4$ substituents.

30. A compound of claim 29, wherein R$^1$ is H; R$^2$ is selected from the group consisting of halogen, $C_{1-4}$ alkyl, $C_{1-4}$ alkoxy, $C_{1-4}$ haloalkyl, —CN, —C≡CH and —CONH$_2$; each R$^3$, when present is independently selected from the group consisting of $C_{1-4}$ alkyl, $C_{1-4}$ alkoxy, $C_{3-5}$ cycloalkyl-alkoxy, —O(CH$_2$)$_m$OR$^{3b}$ and —O(CH$_2$)$_m$N(R$^{3b}$)$_2$ wherein the subscript m is 1 or 2 and each R$^{3b}$ is independently selected from the group consisting of H, $C_{1-4}$ alkyl and $C_{1-4}$ alkanoyl; and each R$^4$, when present is independently selected from the group consisting of halogen, cyano, hydroxy, $C_{1-6}$ alkyl, $C_{2-6}$ alkenyl, $C_{2-6}$ alkynyl, $C_{1-6}$ alkoxy, $C_{1-6}$ haloalkyl, $C_{3-5}$ cycloalkyl, $C_{3-5}$ cycloalkyl-alkyl, $C_{3-5}$ cycloalkyl-alkoxy and ($C_{1-6}$ alkyl)$_{0-2}$ amino.

31. A compound of claim 30, wherein R$^2$ is halogen and is attached to the 5-position of the thienyl ring; and each R$^4$ when present is independently selected from the group consisting of halogen, cyano and $C_{1-6}$ alkyl.

32. A compound of claim 1, having the formula:

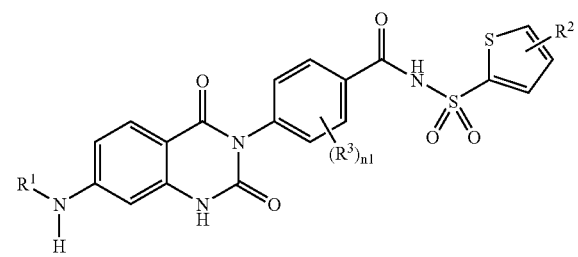

wherein the subscript n1 represents an integer of from 0 to 2, and R$^1$ is a member selected from the group consisting of $C_{1-6}$ alkyl, $C_{1-6}$ haloalkyl, $C_{3-5}$ cycloalkyl and $C_{3-5}$ cycloalkyl-alkyl.

33. A compound of claim 32, wherein R$^2$ is selected from the group consisting of halogen, $C_{1-4}$ alkyl, $C_{1-4}$ alkoxy, $C_{1-4}$ haloalkyl, —CN, —C≡CH and —CONH$_2$; and each R$^3$, when present is independently selected from the group consisting of $C_{1-4}$ alkyl, $C_{1-4}$ alkoxy, $C_{3-5}$ cycloalkyl-alkoxy, —O(CH$_2$)$_m$OR$^{3b}$ and —O(CH$_2$)$_m$N(R$^{3b}$)$_2$ wherein the subscript m is 1 or 2 and each R$^{3b}$ is independently selected from the group consisting of H, $C_{1-4}$ alkyl and $C_{1-4}$ alkanoyl.

34. A compound of claim 33, wherein R$^2$ is halogen and is attached to the 5-position of the thienyl ring.

35. A pharmaceutical composition comprising a pharmaceutically acceptable carrier and a compound of any of claims 1 to 34.

36. A pharmaceutical composition comprising a pharmaceutically acceptable carrier and a compound having the formula:

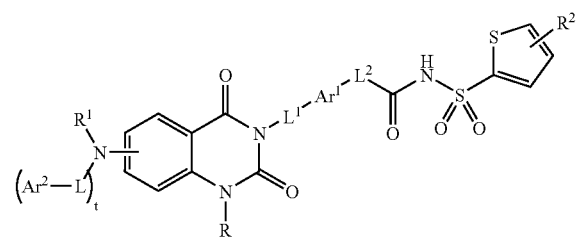

wherein

R is a member selected from the group consisting of H and $C_{1-6}$ alkyl;

R$^1$ is a member selected from the group consisting of H, $C_{1-6}$ alkyl, $C_{1-6}$ haloalkyl, $C_{3-5}$ cycloalkyl and $C_{3-5}$ cycloalkyl-alkyl;

R$^2$ is a member selected from the group consisting of H, halogen, $C_{1-6}$ alkyl, $C_{2-6}$ alkenyl, $C_{2-6}$ alkynyl, $C_{1-6}$ haloalkyl, $C_{1-6}$ alkoxy, cyano and —C(O)R$^{2a}$, wherein $R^{2a}$ is a member selected from the group consisting of $C_{1-6}$ alkoxy and $(C_{1-6}$ alkyl$)_{0-2}$ amino;

L is a 1 to 3 carbon linking group selected from the group consisting of —$CH_2$—, —$CH(CH_3)$—, —$CH_2CH_2$—, —$CH_2CH(CH_3)$— and —$CH_2CH_2CH_2$—;

$L^1$ is a linking group selected from the group consisting of a bond and —$CH_2$—;

$L^2$ is a linking group selected from the group consisting of a bond, —NH— and —$CH_2$—;

$Ar^1$ is an aromatic ring selected from the group consisting of beuzene, pyridine and pyrimidine, each of which is optionally substituted with from 1–2 $R^3$ substituents, wherein each $R^3$ is independently selected from the group consisting of halogen, cyano, hydroxy, $C_{1-6}$ alkyl, $C_{2-6}$ alkenyl, $C_{2-6}$ alkynyl, $C_{1-6}$ alkoxy, $C_{1-6}$ haloalkyl, $C_{1-6}$ haloalkoxy, $C_{3-5}$ cycloalkyl, $C_{3-5}$ cycloalkyl-alkyl, $C_{3-5}$ cycloalkyl-alkoxy, $(C_{1-6}$ alkyl$)_{0-2}$ amino, —$C(O)R^{3a}$, —$O(CH_2)_mOR^{3b}$, —$(CH_2)_mOR^{3b}$, —$O(CH_2)_mN(R^{3b})_2$ and —$(CH_2)_mN(R^{3b})_2$, wherein the subscript m is an integer of from 1 to 3, each $R^{3a}$ is a member independently selected from the group consisting of H, hydroxy, $C_{1-6}$ alkyl, $C_{1-6}$ alkoxy, $(CH_{1-6}$ alkyl$)_{0-2}$ amino, and each $R^{3b}$ is a member independently selected from the group consisting of H, $C_{1-4}$ alkyl and $C_{1-4}$ alkanoyl, and optionally, two $R^{3b}$ groups attached to nitrogen are combined with the nitrogen atom to form an azetidine, pyrrolidine or piperidine ring;

$Ar^2$ is a 5–6 membered monocyclic or 9–10 membered fused-bicyclic aromatic ring system, optionally having from 1 to 3 heteroatoms selected from N, O and S as ring vertices, said ring system being optionally substituted with from 1 to 3 $R^4$ substituents wherein each of said $R^4$ substituents is independently selected from the group consisting of halogen, cyano, hydroxy, $C_{1-6}$ alkyl, $C_{2-6}$ alkenyl, $C_{2-6}$ alkynyl, $C_{1-6}$ alkoxy, $C_{1-6}$ haloalkyl, $C_{1-6}$ haloalkoxy, $C_{3-5}$ cycloalkyl, $C_{3-5}$ cycloalkyl-alkyl, $C_{3-5}$ cycloalkyl-alkoxy, $(C_{1-6}$ alkyl$)_{0-2}$ amino and —$C(O)R^{4a}$, wherein each $R^{4a}$ is a member independently selected from the group consisting of H, hydroxy, $C_{1-6}$ alkyl, $C_{1-6}$ alkoxy and $(C_{1-6}$ alkyl$)_{0-2}$ amino;

the subscript t is 0 or 1 when $L^2$ is a bond, and is 1 when $L^2$ is selected from —NH— and —$CH_2$—;

or a pharmaceutically acceptable salt thereof.

37. A pharmaceutical composition of claim 36, said compound having the formula:

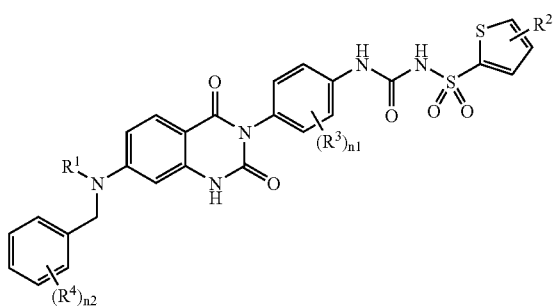

wherein the subscripts n1 and n2 each independently represent an integer of from 0 to 2.

38. A pharmaceutical composition of claim 37, wherein R is H; $R^2$ is selected from the group consisting of halogen, $C_{1-4}$ alkyl, $C_{1-4}$ alkoxy, $C_{1-4}$ haloalkyl, —CN, —C≡CH and —$CONH_2$; each $R^3$, when present is independently selected from the group consisting of $C_{1-4}$ alkyl, $C_{1-4}$ alkoxy, $C_{3-5}$ cycloalkyl-alkoxy, —$O(CH_2)_mOR^{3b}$ and —$O(CH_2)_mN(R^{3b})_2$ wherein the subscript m is 1 or 2 and each $R^{3b}$ is independently selected from the group consisting of H, $C_{1-4}$ alkyl and $C_{1-4}$ alkanoyl; and each $R^4$, when present is independently selected from the group consisting of halogen, cyano, hydroxy, $C_{1-6}$ alkyl, $C_{2-6}$ alkenyl, $C_{2-6}$ alkynyl, $C_{1-6}$ alkoxy, $C_{1-6}$ haloalkyl, $C_{3-5}$ cycloalkyl, $C_{3-5}$ cycloalkyl-alkyl, $C_{3-5}$ cycloalkyl-alkoxy and $(C_{1-6}$ alkyl$)_{0-2}$ amino.

39. A method of treating thrombosis in a subject comprising administering to a subject in need thereof, a therapeutically effective amount of a compound of any of claims 1 to 34.

40. A method of treating thrombosis in a subject comprising administering to a subject in need thereof, a therapeutically effective amount of a compound having the formula:

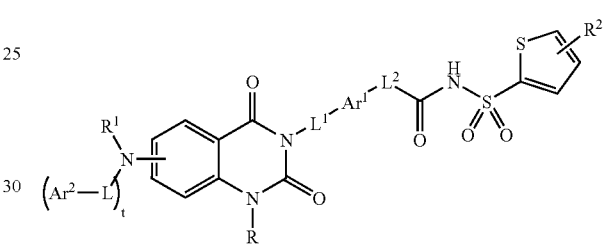

wherein

R is a member selected from the group consisting of H and $C_{1-6}$ alkyl;

$R^1$ is a member selected from the group consisting of H, $C_{1-6}$ alkyl, $C_{1-6}$ haloatkyl, $C_{3-5}$ cycloalkyl and $C_{3-5}$ cycloalkyl-alkyl;

$R^2$ is a member selected from the group consisting of H, halogen, $C_{1-6}$ alkyl, $C_{2-6}$ alkenyl, $C_{2-6}$ alkynyl, $C_{1-6}$ haloalkyl, $C_{1-6}$ alkoxy, cyano and —$C(O)R^{2a}$, wherein $R^{2a}$ is a member selected from the group consisting of $C_{1-6}$ alkoxy and $(C_{1-6}$ alkyl$)_{0-2}$ amino;

L is a 1 to 3 carbon linking group selected from the group consisting of —$CH_2$—, —$CH(CH_3)$—, —$CH_2CH_2$—, —$CH_2CH(CH_3)$— and —$CH_2CH_2CH_2$—;

$L^1$ is a linking group selected from the group consisting of a bond and —$CH_2$—;

$L^2$ is a linking group selected from the group consisting of a bond, —NH— and —$CH_2$—;

$Ar^1$ is an aromatic ring selected from the group consisting of benzene, pyridine and pyrimidine, each of which is optionally substituted with from 1–2 $R^3$ substituents, wherein each $R^3$ is independently selected from the group consisting of halogen, cyano, hydroxy, $C_{1-6}$ alkyl, $C_{2-6}$ alkenyl, $C_{2-6}$ alkynyl, $C_{1-6}$ alkoxy, $C_{1-6}$ haloalkyl, $C_{1-6}$ haloalkoxy, $C_{3-5}$ cycloalkyl, $C_{3-5}$ cycloalkyl-alkyl, $C_{3-5}$ cycloalkyl-alkoxy, $(C_{1-6}$ alkyl$)_{0-2}$ amino, —$C(O)R^{3a}$, —$O(CH_2)_mOR^{3b}$, —$(CH_2)_mOR^{3b}$, —$O(CH_2)_mN(R^{3b})_2$ and —$(CH_2)_mN(R^{3b})_2$, wherein the subscript m is an integer of from 1 to 3, each $R^{3a}$ is a member independently selected from the group consisting of H, hydroxy, $C_{1-6}$ alkyl, $C_{1-6}$ alkoxy, $(C_{1-6}$ alkyl$)_{0-2}$ amino, and each $R^{3b}$ is a member independently selected from the group consisting of H, $C_{1-4}$ alkyl and $C_{1-4}$ alkanoyl, and optionally, two $R^{3b}$ groups attached to nitrogen are combined with the nitrogen atom to form an azetidine, pyrrolidine or piperidine ring;

$Ar^2$ is a 5–6 membered monocyclic or 9–10 membered fused-bicyclic aromatic ring system, optionally having from 1 to 3 heteroatoms selected from N, O and S as ring vertices, said ring system being optionally substituted with from 1 to 3 1 $R^4$ substituents wherein each of said $R^4$ substituents is independently selected from the group consisting of halogen, cyano, hydroxy, $C_{1-6}$ alkyl, $C_{2-6}$ alkenyl, $C_{2-6}$ alkynyl, $C_{1-6}$ alkoxy, $C_{1-6}$ haloalkyl, $C_{1-6}$ haloalkoxy, $C_{3-5}$ cycloalkyl, $C_{3-5}$ cycloalkyl-alkyl, $C_{3-5}$ cycloalkyl-alkoxy, $(C_{1-6}$ alkyl$)_{0-2}$ amino and —C(O)$R^{4a}$, wherein each $R^{4a}$ is a member independently selected from the group consisting of H, hydroxy, $C_{1-6}$ alkyl, $C_{1-6}$ alkoxy and $(C_{1-6}$ alkyl$)_{0-2}$ amino;

the subscript t is 0 or 1 when $L^2$ is a bond, and is 1 when $L^2$ is selected from —NH— and —CH$_2$—;

or a pharmaceutically acceptable salt thereof.

41. A method in accordance with claim 40, wherein said compound is administered in combination with a second therapeutic agent selected from the group consisting of antiplatelet compounds, anticoagulants, fibrinolytics, anti-inflammatory compounds, cholesterol-lowering agents, blood pressure-lowering agents and serotonin blockers.

42. A method in accordance with claim 41, wherein said second therapeutic agent is an antiplatelet compound selected from the group consisting of GPIIB–IIIa antagonists, aspirin, phosphodiesterase III inhibitors and thromboxane A2 receptor antoagonists.

43. A method in accordance with claim 41, wherein said second therapeutic agent is an anticoagulant selected from the group consisting of thrombin inhibitors, coumadin, heparin and Lovenox®.

44. A method in accordance with claim 41, wherein said second therapeutic agent is an anti-inflammatory compound selected from the group consisting of non-steroidal anti-inflammatory agents, cyclooxygenase-2 inhibitors and rheumatoid arthritis agents.

45. A method in accordance with claim 41, wherein said compound is administered orally.

46. A method in accordance with claim 40, wherein said compound has the formula:

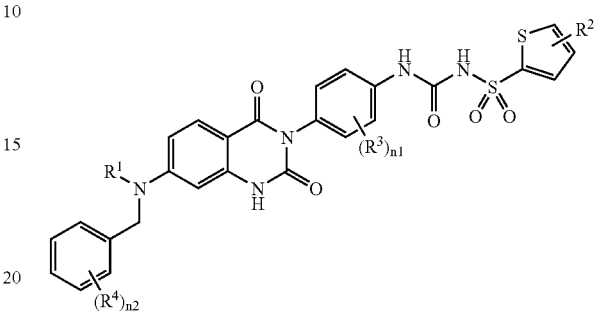

wherein the subscripts n1 and n2 each independently represent an integer of from 0 to 2; $R^{is\ H}$;

$R^2$ is selected from the group consisting of halogen, $C_{1-4}$ alkyl, $C_{1-4}$ alkoxy, $C_{1-4}$ haloalkyl, —CN, —C≡CH and —CONH$_2$; each $R^3$, when present is independently selected from the group consisting of $C_{1-4}$ alkyl, $C_{1-4}$ alkoxy, $C_{3-5}$ cycloalkyl-alkoxy, —O(CH$_2$)$_m$OR$^{3b}$ and —O(CH$_2$)$_m$N(R$^{3b}$)$_2$ wherein the subscript m is 1 or 2 and each $R^{3b}$ is independently selected from the group consisting of H, $C_{1-4}$ alkyl and $C_{1-4}$ alkanoyl; and each $R^4$, when present is independently selected from the group consisting of halogen, cyano, hydroxy, $C_{1-6}$ alkyl, $C_{2-6}$ alkenyl, $C_{2-6}$ alkynyl, $C_{1-6}$ alkoxy, $C_{1-6}$ haloalkyl, $C_{3-5}$ cycloalkyl, $C_{3-5}$ cycloalkyl-alkyl, $C_{3-5}$ cycloalkyl-alkoxy and $(C_{1-6}$ alkyl$)_{0-2}$ amino.

\* \* \* \* \*